United States Patent
Hunter et al.

(10) Patent No.: US 12,428,484 B2
(45) Date of Patent: Sep. 30, 2025

(54) ANTI-ALK2 ANTIBODIES AND USES THEREOF

(71) Applicant: Alexion Pharmaceuticals, Inc., Boston, MA (US)

(72) Inventors: Jeffrey William Hunter, Wallingford, CT (US); Julian Chandler, Old Lyme, CT (US); Keith Bouchard, Unionville, CT (US); Andre Marozsan, Killingworth, CT (US); Patricia Bento, Plantsville, CT (US); Anjli Kukreja, Fairfield, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 1128 days.

(21) Appl. No.: 17/297,847

(22) PCT Filed: Dec. 5, 2019

(86) PCT No.: PCT/US2019/064613
§ 371 (c)(1),
(2) Date: May 27, 2021

(87) PCT Pub. No.: WO2020/118011
PCT Pub. Date: Jun. 11, 2020

(65) Prior Publication Data
US 2022/0098310 A1    Mar. 31, 2022

Related U.S. Application Data

(60) Provisional application No. 62/776,280, filed on Dec. 6, 2018.

(51) Int. Cl.
| | |
|---|---|
| *C07K 16/28* | (2006.01) |
| *A61K 31/59* | (2006.01) |
| *A61K 33/06* | (2006.01) |
| *A61K 39/00* | (2006.01) |
| *A61K 39/395* | (2006.01) |
| *A61P 19/10* | (2006.01) |
| *G01N 33/573* | (2006.01) |

(52) U.S. Cl.
CPC .......... *C07K 16/2863* (2013.01); *A61K 31/59* (2013.01); *A61K 33/06* (2013.01); *A61K 39/3955* (2013.01); *A61P 19/10* (2018.01); *G01N 33/573* (2013.01); *A61K 2039/505* (2013.01); *C07K 2317/24* (2013.01); *C07K 2317/92* (2013.01); *G01N 2333/912* (2013.01)

(58) Field of Classification Search
None
See application file for complete search history.

(56) References Cited

FOREIGN PATENT DOCUMENTS

EP    3252074 A1    12/2017

OTHER PUBLICATIONS

Vajdos et al., Comprehensive Functional Maps of the Antigenbinding Site of an Anti-ErbB2 Antibody Obtained with Shotgun Scanning Mutagenesis. J. Mol. Biol. 320:415-428, 2002.*
International Search Report and Written Opinion, PCT/US2019/064613, dated Mar. 25, 2020, 14 pages.
Kamiya, N. et al., "Loss-of-function of ACUR1 in osteoblasts increases bone mass and activates canonical Wnt signaling through suppression of Wnt inhibitors SOST and DKK1," Biochemical and Biophyscial Research Communications, vol. 414(2):326-330 (2011).
Pang Jing et al., "ACUR1-Fc suppresses BMP signaling and chondroosseous differentiation in an in vitro model of Fibrodysplasia ossificans progressiva," Bone, Pergamon PRESS.vol. 92: 29-36 (2016).
Shi C., et al., "Bone morphogenetic protein signaling through ACUR1 and BMPR1A negatively regulates bone mass along with alterations in bone composition," Journal of Structural Biology, vol. 201 (3):237-246 (2017).

* cited by examiner

*Primary Examiner* — Ruixiang Li
(74) *Attorney, Agent, or Firm* — Nelson Mullins Riley & Scarborough LLP; Jane E. Remillard, Esq.; Jill Gorny Sloper, Esq.

(57) ABSTRACT

Provided herein are antibodies that bind to activin receptor-like kinase 2 (ALK2) and are useful for treating bone disorders, such as those involving reduced bone mineral density and bone mineralization defects, and promoting bone growth. Also provided are polynucleotides encoding the antibodies, vectors comprising the polynucleotides, and cells that produce the antibodies.

18 Claims, 28 Drawing Sheets
Specification includes a Sequence Listing.

ANTI-ALK2 ANTIBODIES AND USES THEREOF

CROSS-REFERENCE TO RELATED APPLICATIONS

This application is a 35 U.S.C. 371 national stage filing of International Application No. PCT/US2019/064613, filed on Dec. 5, 2019, which claims priority to and the benefit of U.S. Provisional Application Ser. No. 62/776,280, filed on Dec. 6, 2018. The entire contents of the aforementioned applications are incorporated herein by reference.

SEQUENCE LISTING

The instant application contains a Sequence Listing that has been submitted electronically in ASCII format and is hereby incorporated by reference in its entirety. Said ASCII copy, created on Dec. 6, 2021, is named AXJ-254US_Sequence_Listing.txt and is 133,233 bytes in size.

BACKGROUND

Bone homeostasis is achieved through a balance between bone resorption and formation, and abnormalities in either of these processes can lead to wide range of disorders, including osteoporosis. Osteoporosis is a bone disorder characterized by loss of bone mass and tissue, and affects more than 200 million people worldwide. Among the risk factors of osteoporosis are age, low bone density, family history of the disease, and taking certain medications. Current treatments include, for example, calcium, vitamin D, estrogen replacement therapy, bisphosphonates, statins, parathyroid hormone, and estrogen receptor modulators, some of which are associated with undesirable side effects. Thus, there exists a need for novel therapeutic agents that promote bone growth and can be used to treat bone disorders associated with bone loss (e.g., osteoporosis).

SUMMARY

Mutations in the gene encoding the ALK2 protein are responsible for fibrodysplasia ossificans progressiva (FOP), a rare genetic disorder characterized by heterotopic bone formation. ALK2 is a transmembrane kinase receptor that binds to bone morphogenic proteins (BMPs). Specifically, gain-of-function mutations in the ALK2 gene have been identified as being responsible for FOP, and thus inhibitors of aberrant BMP signaling caused by mutant ALK2 have been proposed to prevent FOP heterotopic bone formation. Inhibitors of aberrant ALK2 signaling caused by mutant forms of ALK2 include, for example, anti-activin A antibody, ACVR2A-Fc, and ACVR2B-Fc (Hatsell et al., *Sci Transl Med* 2015; 7:303ra137), LDN193189 (Yu et al., *Nat Med* 2008; 14:1363-9), LDN212854 (Mohedas et al., *ACS Chem Biol.* 2013; 8:1291-1302), and anti-sense oligonucleotides against ALK2 (*PLoS One* 2013; 8:e69096). U.S. Patent Appln. Pub. No, 2018/0118835 discloses anti-ALK2 antibodies which are useful for treating and/or preventing ectopic calcification and/or bone dysplasia, anemia, or diffuse intrinsic pontine glioma.

The present invention is based on the discovery that, contrary to wide-spread evidence in the literature that small molecule kinase inhibitors of the ALK2 signaling pathway prevent or reduce bone formation in mice that express gain-of-function mutants of ALK2, the antagonistic anti-ALK2 antibodies described herein surprisingly promote increased bone density and may promote bone growth and formation. Accordingly, the anti-ALK2 antibodies described herein are useful, e.g., for the treatment of various disorders that would benefit from increased bone density, growth, and formation.

In one aspect, provided herein is an antibody which binds to activin receptor-like kinase 2 (ALK2) and exhibits at least two (e.g., two, three, four, five, or six) of the following properties:
  a) binds to both mouse and human ALK2 (e.g., binds to human ALK2 with a KD of about 500 nM or less);
  b) binds to ALK2 expressed on at least one of osteoblasts, osteoclasts, and/or progenitor cells (i.e., fibro-adipogenic progenitors (FAP);
  c) stimulates bone mineralization;
  d) increases bone mineral density;
  e) inhibits stimulation of ALK2 by BMP ligands; and
  f) inhibits downstream Alk-2 mediated BMP signaling by SMAD proteins.

In another aspect, provided herein is an antibody which binds to ALK2 and comprises the three variable heavy chain CDRs and the three light chain CDRs that are in the variable heavy chain and variable light chain pairs selected from the group consisting of: (a) SEQ ID NOs: 16 and 17, respectively; (b) SEQ ID NOs: 26 and 27, respectively; (c) SEQ ID NOs: 36 and 37, respectively; and (d) SEQ ID NOs: 46 and 47, respectively.

In another aspect, provided herein is an antibody which binds to ALK2, comprising:
  (a) heavy chain CDR1, CDR2, and CDR3 sequences comprising SEQ ID NOs: 10, 11, and 12, respectively, and/or light chain CDR1, CDR2, and CDR3 sequences comprising SEQ ID NOs: 13, 14, and 15, respectively;
  (b) heavy chain CDR1, CDR2, and CDR3 sequences comprising SEQ ID NOs: 20, 21, and 22, respectively, and/or light chain CDR1, CDR2, and CDR3 sequences comprising SEQ ID NOs: 23, 24, and 25, respectively;
  (c) heavy chain CDR1, CDR2, and CDR3 sequences comprising SEQ ID NOs: 30, 31, and 32, respectively, and/or light chain CDR1, CDR2, and CDR3 sequences comprising SEQ ID NOs: 33, 34, and 35, respectively;
  (d) heavy chain CDR1, CDR2, and CDR3 sequences comprising SEQ ID NOs: 40, 41, and 42, respectively, and/or light chain CDR1, CDR2, and CDR3 sequences comprising SEQ ID NOs: 43, 44, and 45, respectively.

In another aspect, provided herein is an antibody which binds to ALK2 and comprises heavy and light chain variable regions, wherein the heavy chain variable region comprises an amino acid sequence which is at least 90% identical to the amino acid sequence selected from the group consisting of SEQ ID NOs: 16, 26, 36, and 46.

In another aspect, provided herein is an antibody which binds to ALK2 and comprises heavy and light chain variable regions, wherein the light chain variable region comprises an amino acid sequence which is at least 90% identical to the amino acid sequence selected from the group consisting of SEQ ID NOs: 17, 27, 37, and 47.

In another aspect, provided herein is an antibody which binds to ALK2 and comprises heavy and light chain variable region sequences at least 80%, 85%, 90%, 95%, 96%, 97%, 98%, 99%, or 100% identical to the amino acid sequences selected from the group consisting of: (a) SEQ ID NOs: 16 and 17, respectively; (b) SEQ ID NOs: 26 and 27, respectively; (c) SEQ ID NOs: 36 and 37, respectively; and (d) SEQ ID NOs: 46 and 47, respectively.

In another aspect, provided herein is an antibody which binds to ALK2 and comprises heavy chain and light chain sequences at least 80%, 85%, 90%, 95%, 96%, 97%, 98%, 99%, or 100% identical to the amino acid sequences selected from the group consisting of: (a) SEQ ID NOs: 18 and 19, respectively; (b) SEQ ID NOs: 28 and 29, respectively; (c) SEQ ID NOs: 38 and 39, respectively; and (d) SEQ ID NOs: 48 and 49, respectively.

In some embodiments, provided herein are antibodies which bind the same epitope on ALK2 as the anti-ALK2 antibodies described herein. In some embodiments, provided herein are antibodies which compete for binding to ALK2 with the anti-ALK2 antibodies described herein.

In some embodiments, the anti-ALK2 antibodies described herein stimulate bone mineralization in osteoblasts and/or increase bone mineral density.

In some embodiments, the anti-ALK2 antibodies described herein are IgG1, IgG2, IgG3, or IgG4 antibodies, or variants thereof. In some embodiments, the antibody comprises an effectorless Fc region, such as a IgG2/IgG4 hybrid Fc region.

In some embodiments, the anti-ALK2 antibodies are full length antibodies. In some embodiments, the anti-ALK2 antibodies are antigen-binding fragments. In some embodiments, the anti-ALK2 antibodies are chimeric, human, or humanized antibodies.

In some embodiments, the anti-ALK2 antibodies have a second binding specificity. In some embodiments, provided herein are immunoconjugates comprising the anti-ALK2 antibodies described herein.

Also provided are nucleic acids encoding the heavy and/or light chain variable region of the anti-ALK2 antibodies described herein (e.g., one nucleic acid encoding the heavy chain or variable region thereof, and another nucleic acid encoding the light chain or variable region thereof, or a nucleic acid encoding both the heavy chain and light chain, or variable regions thereof), expression vectors comprising the nucleic acids, cells transformed with the expression vectors.

Also provided herein are compositions (e.g., pharmaceutical compositions) comprising the anti-ALK2 antibodies and immunoconjugates described herein, and a carrier (e.g., a pharmaceutically acceptable carrier), as well as kits comprising the anti-ALK2 antibodies and immunoconjugates described herein and instructions for use.

In another aspect, provided herein is a method of preparing an anti-ALK2 antibody comprising expressing the antibody in a host cell that is transformed with the expression vector or nucleic acid described above, and isolating the antibody from the cell.

In another aspect, provided herein is a method of promoting bone growth or formation, increasing bone growth, increasing bone density, promoting skeletal bone mineralization, increasing cortical bone thickness, treating a bone disorder characterized by loss of bone density, treating a bone fracture, preventing bone loss, and/or preventing bone demineralization in a subject (e.g., a human subject) comprising administering an effective amount (e.g., a therapeutically effective amount) of an anti-ALK2 antibodies described herein to the subject. In some embodiments, the subject has at least one of osteoporosis, osteopenia, skeletal bone mineralization defects, bone mineral density loss, diabetes mellitus, systemic lupus erythematosus, rheumatoid arthritis, multiple sclerosis, hyperthyroidism, celiac disease, Crohn's disease, smoking, and cortical steroid use.

In some embodiments, the anti-ALK2 antibodies described herein are administered with one or more additional therapeutics, e.g., vitamin D or calcium.

In another aspect, provided herein is a method of detecting the presence of ALK2 in a sample (e.g., a biological sample) comprising contacting the sample with an anti-ALK2 antibody described herein under conditions that allow for formation of a complex between the antibody and ALK2, and detecting the formation of a complex.

Figure 20:
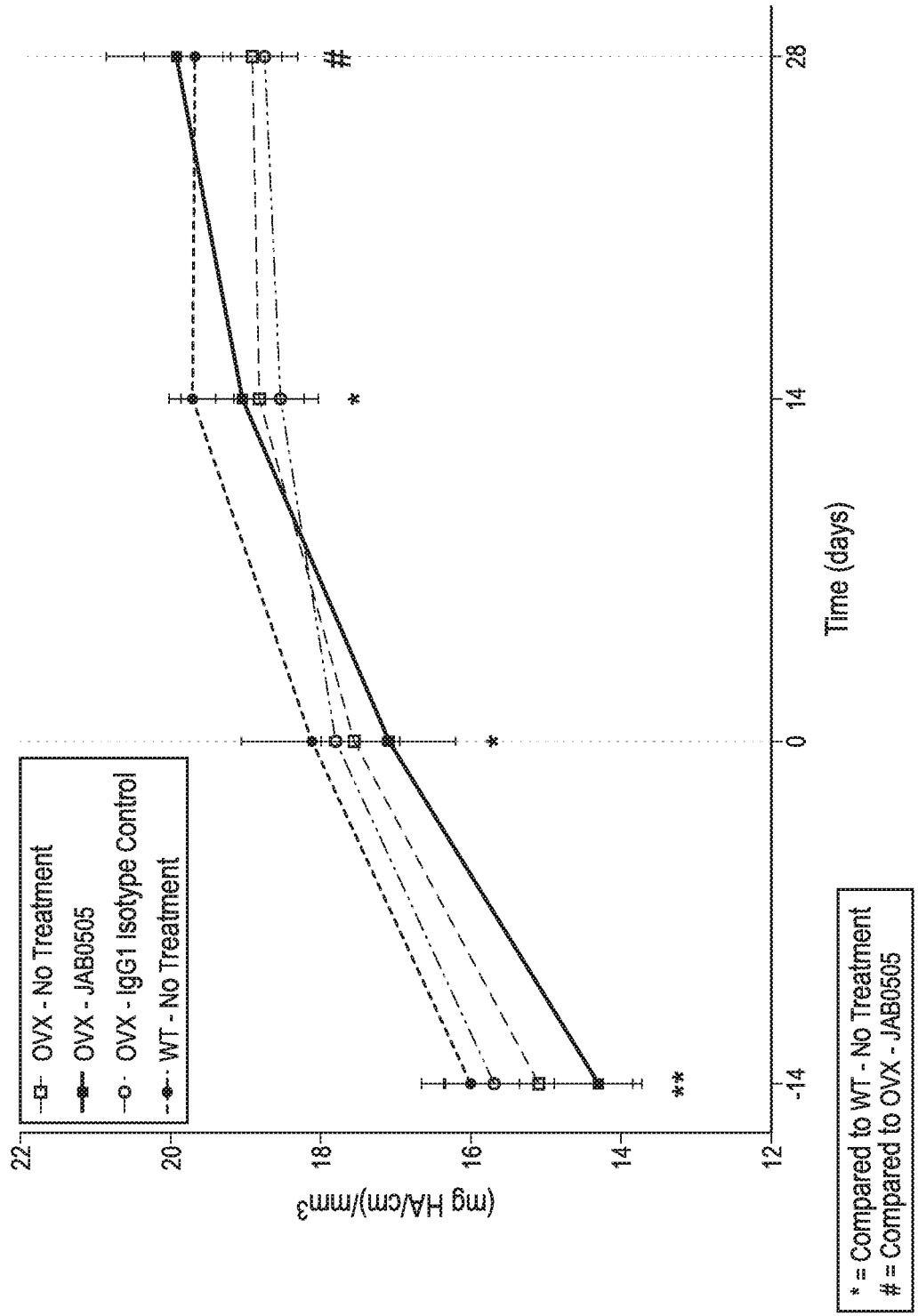

FIG. 20 shows the change in bone mineral density normalized to total bone volume in OVX mice treated with antibody JAB0505 (* or # corresponds to <0.05;  or ## correspond to <0.01; * or ### correspond to <0.001, and **** or #### correspond to <0.0001; * indicates comparison to untreated WT mice and # indicates comparison to OVX treated with JAB0505).

Figure 21:
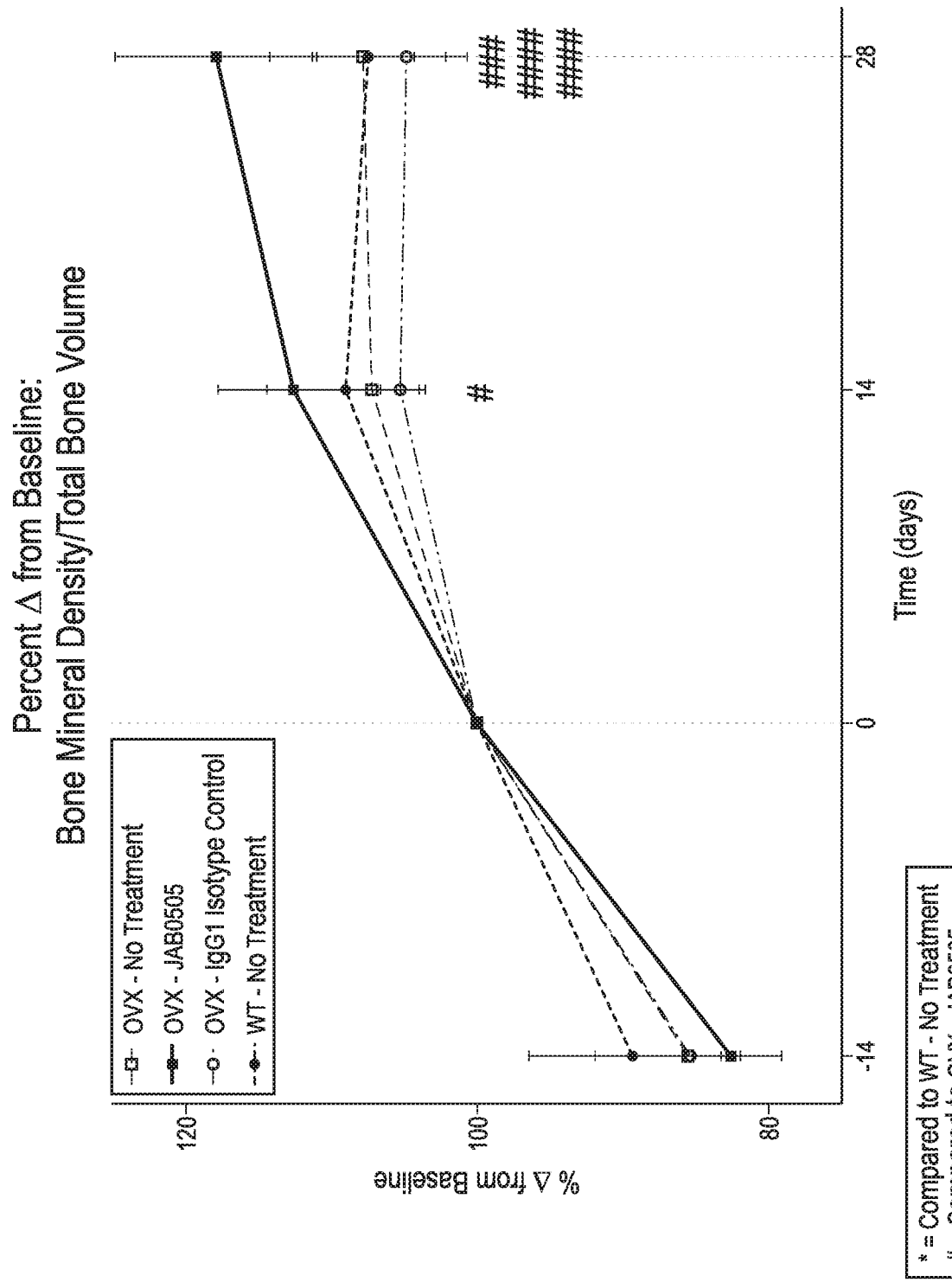

FIG. 21 shows the percent change from baseline in bone mineral density normalized to total bone volume in OVX mice treated with antibody JAB0505 (* or # corresponds to <0.05;  or ## correspond to <0.01; * or ### correspond to <0.001, and **** or #### correspond to <0.0001; * indicates comparison to untreated WT mice and # indicates comparison to OVX treated with JAB0505).

Figure 22:
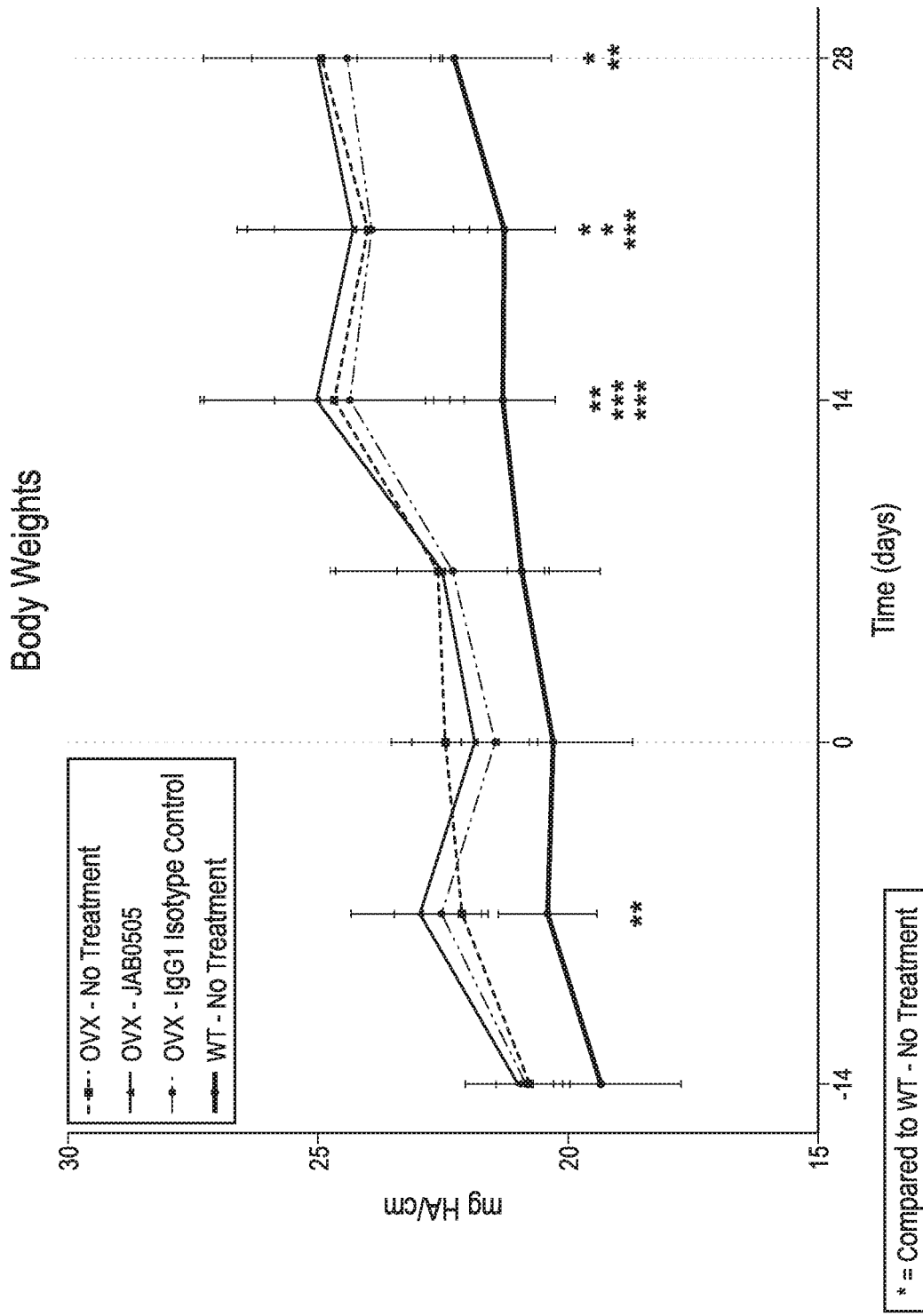

FIG. 22 shows the body weights of OVX mice treated with JAB0505. (* corresponds to <0.05;  corresponds to <0.01; * corresponds to <0.001, and **** corresponds to <0.0001; * indicates comparison to untreated WT mice). Standard deviation bars for n=3 shown.

Figure 23:
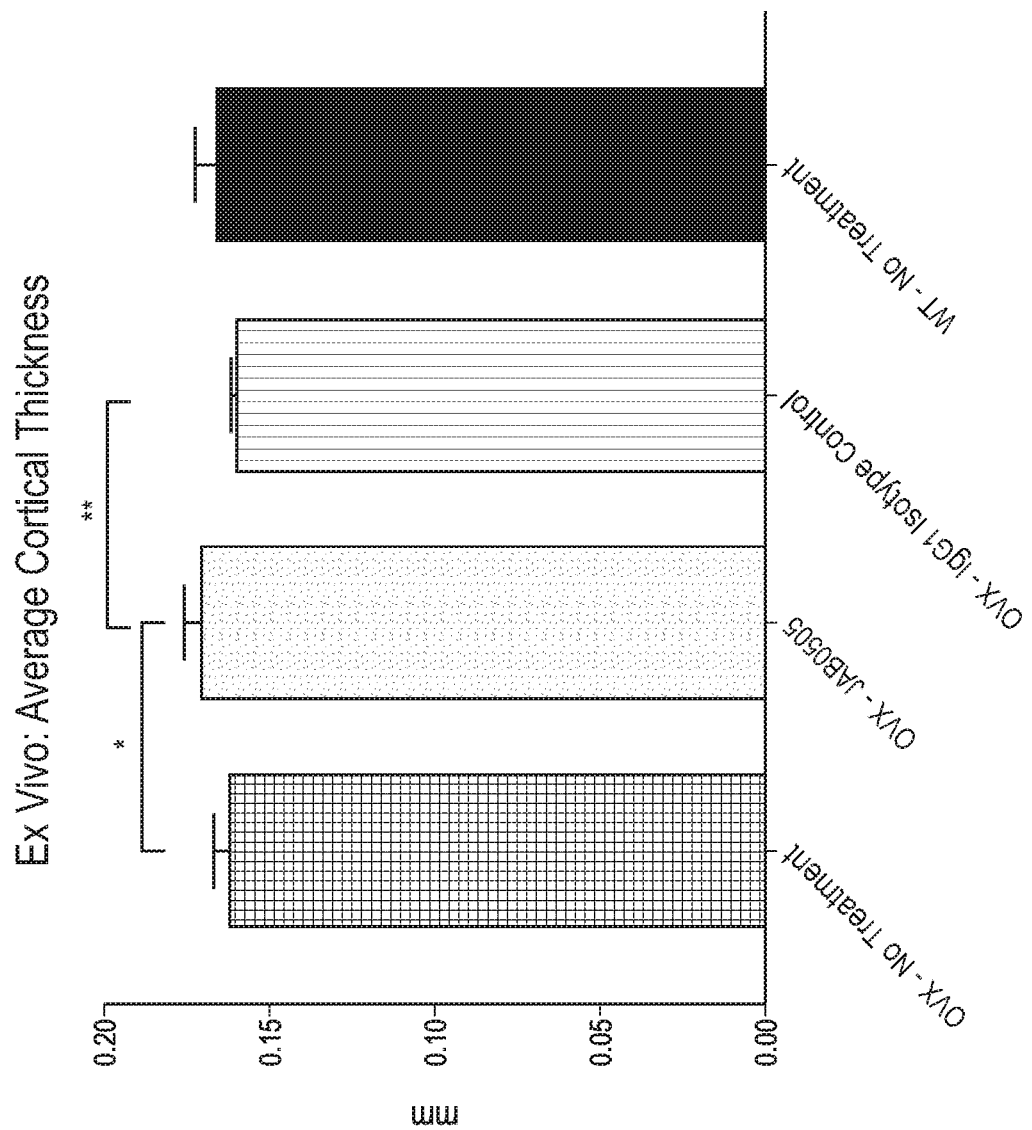
Figures 24A, 24B:
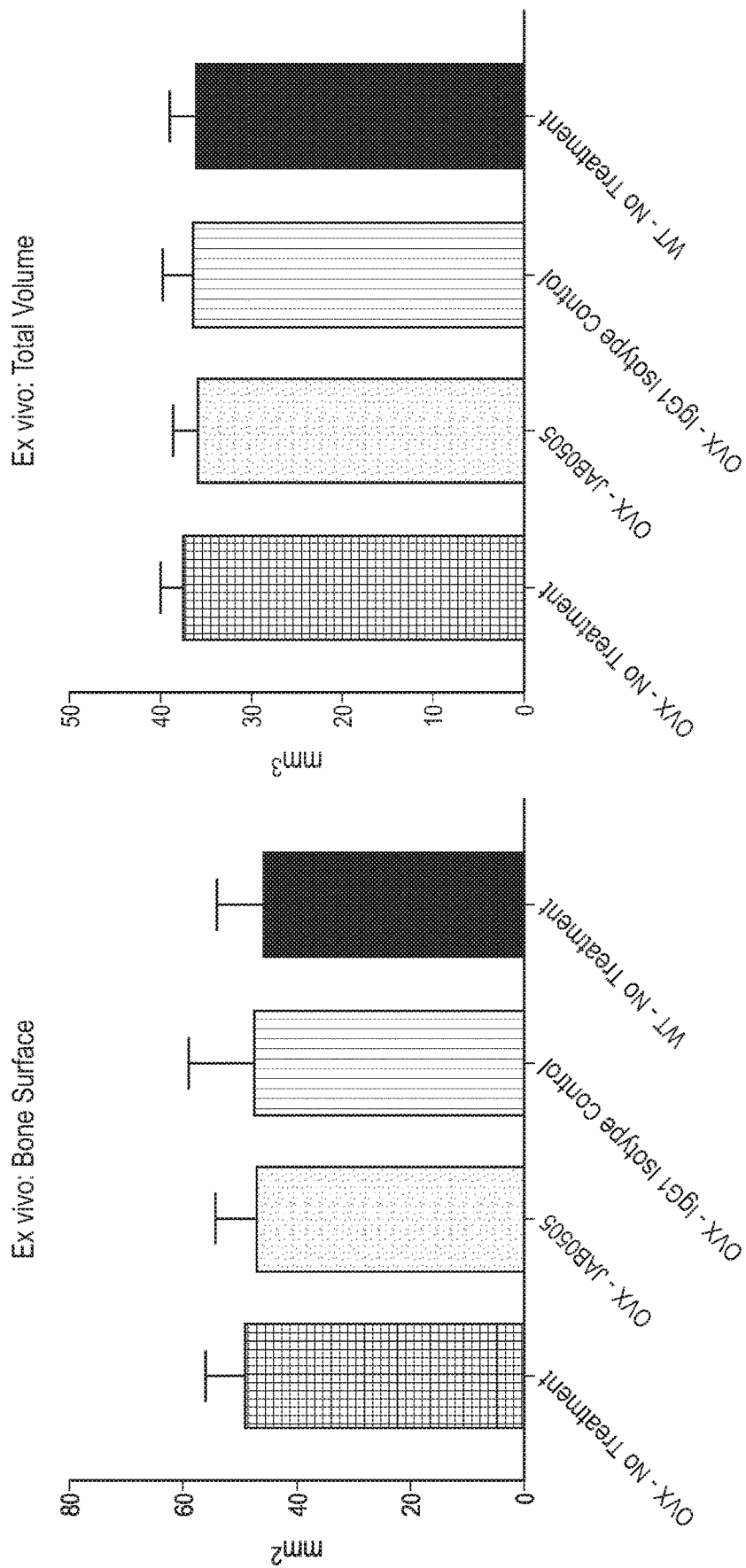
Figure 24D:
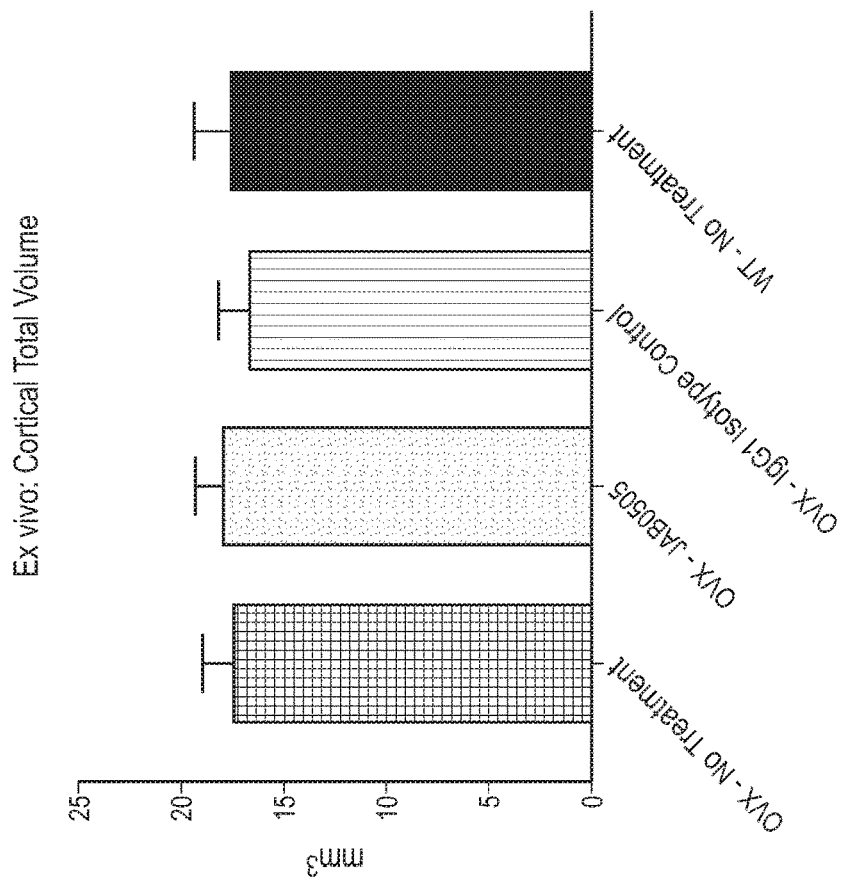
Figure 24C:
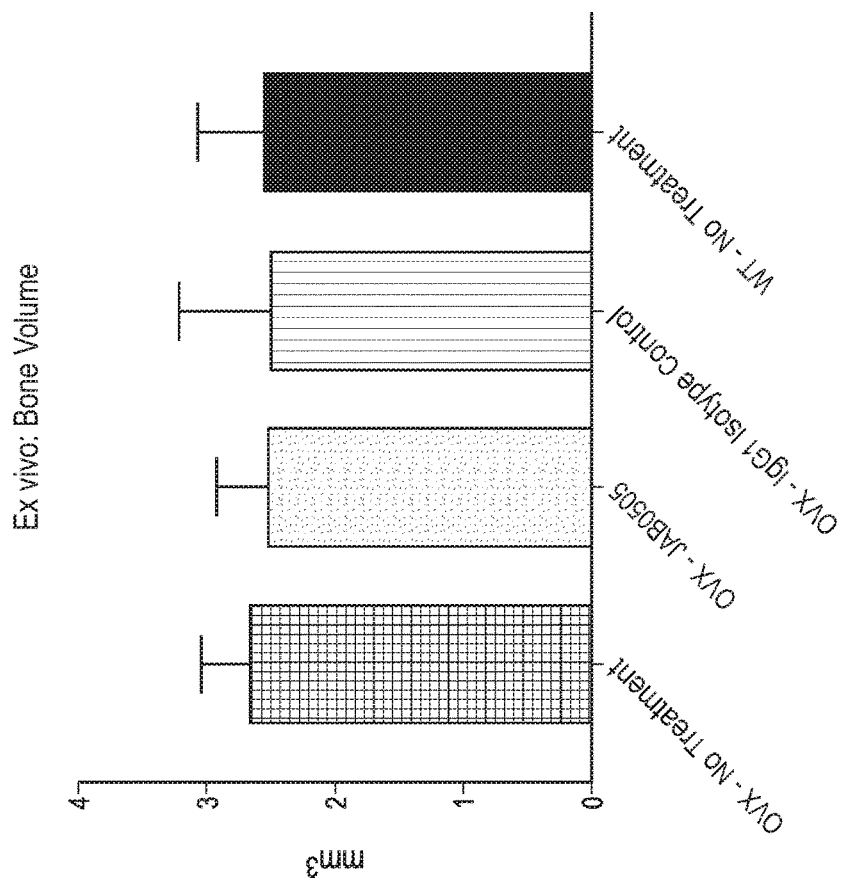
Figure 24F:
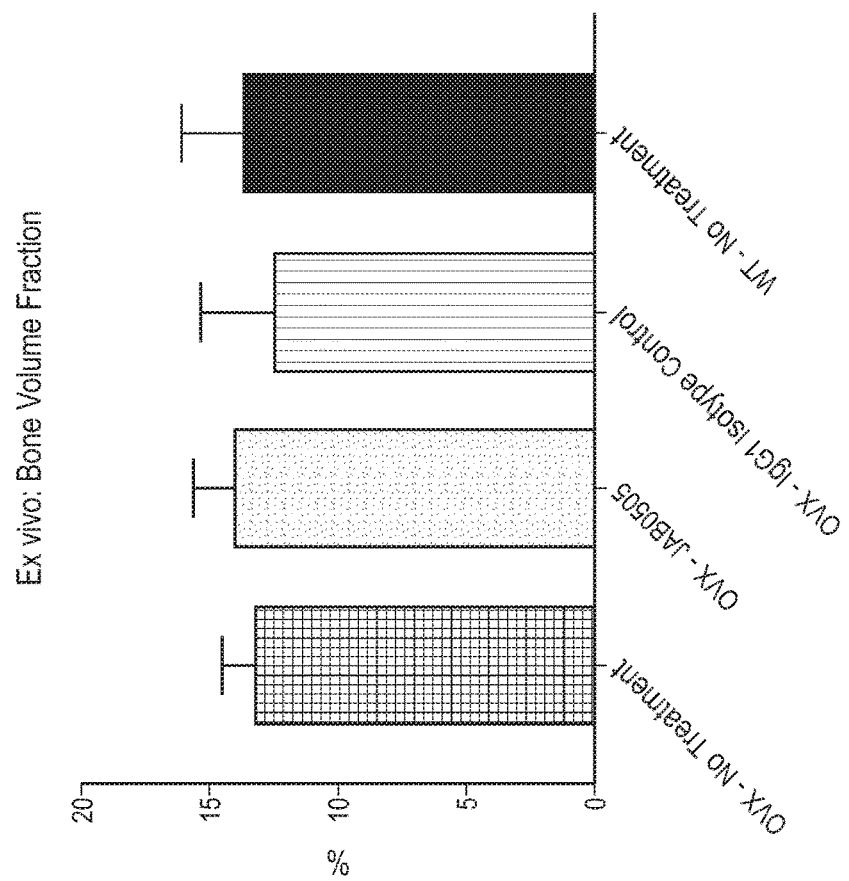
Figure 24E:
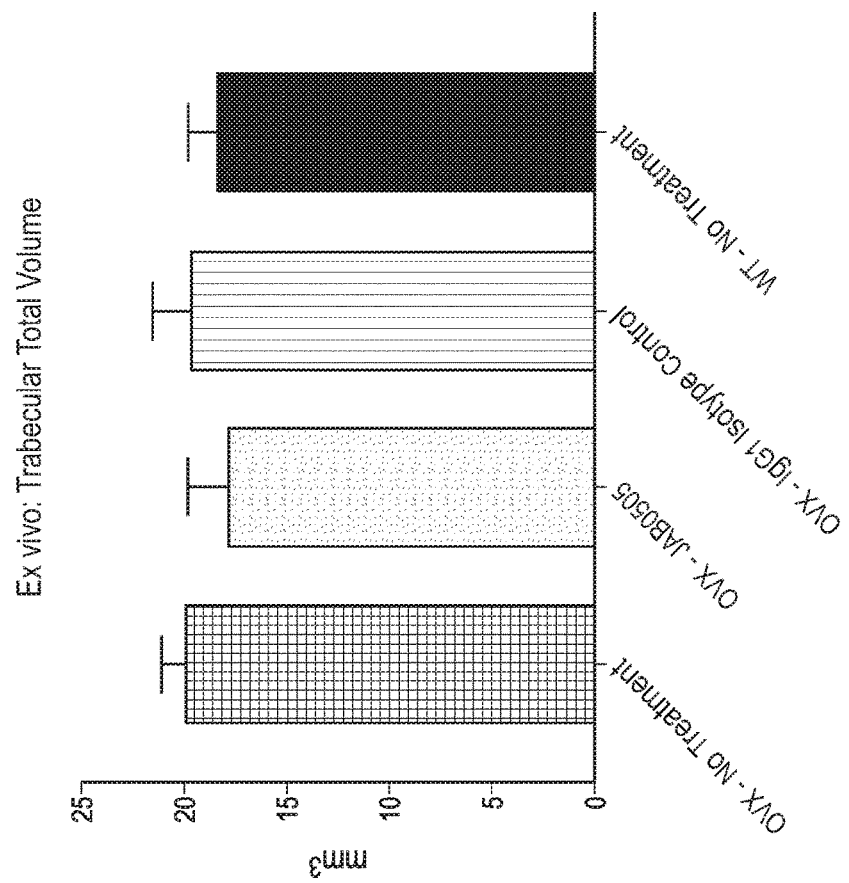
Figures 24G, 24H:
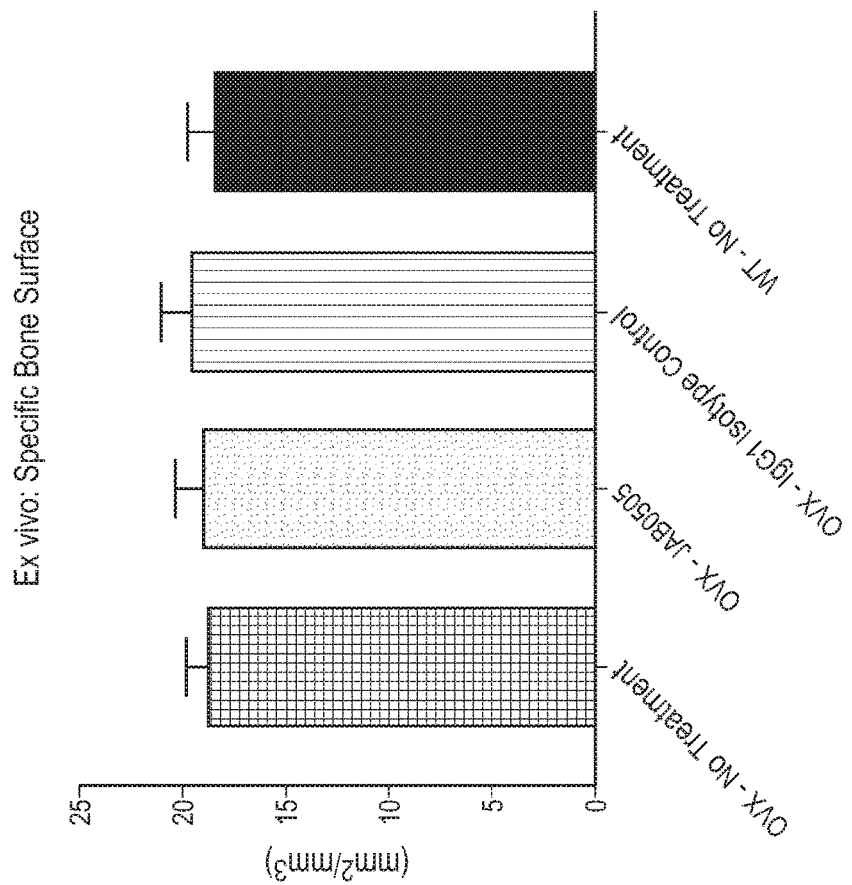
Figure 24I:
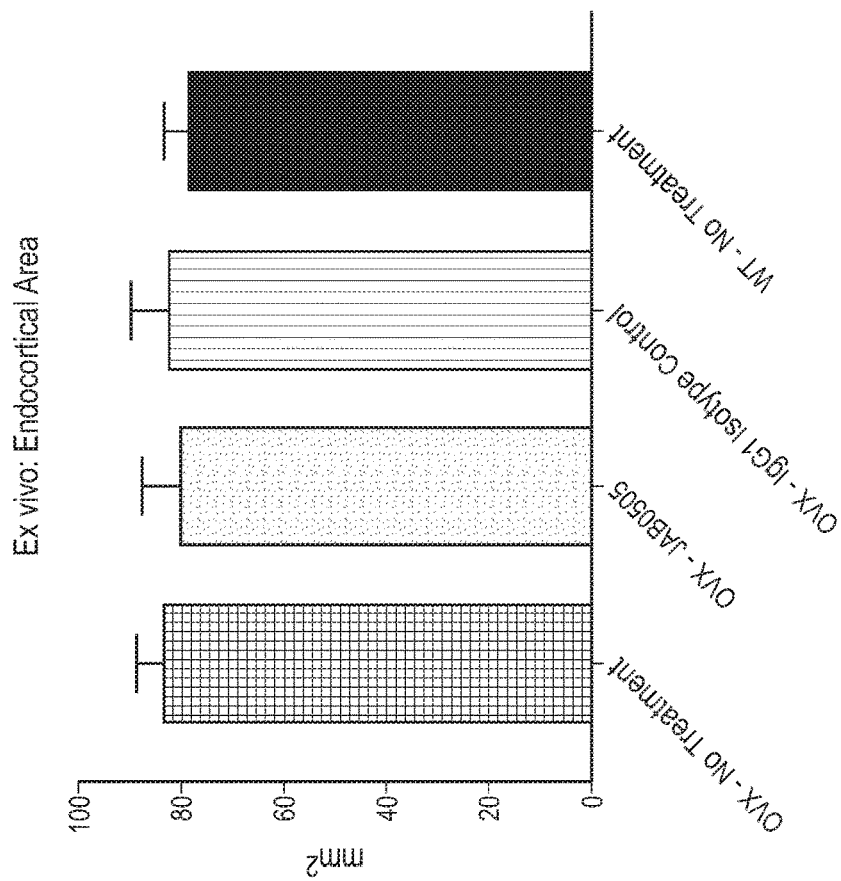
Figure 24J:
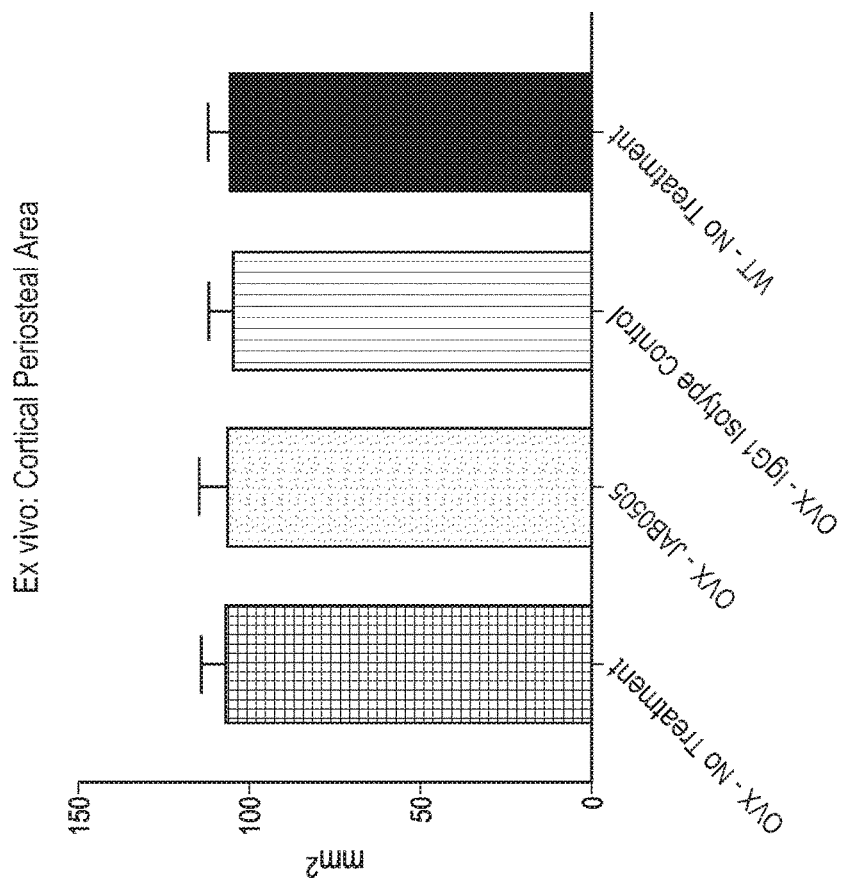

FIG. 23 shows the average cortical thickness in OXA mice treated with antibody JAB0505. Standard deviation bars for n=3 shown.

FIGS. 24A to 24J show bone morphology and growth measurements in OXA mice treated with antibody JAB0505. Standard deviation bars for n=3 shown.

DETAILED DESCRIPTION

In order that the present description may be more readily understood, certain terms are first defined. Additional definitions are set forth throughout the detailed description. Unless defined otherwise, all technical and scientific terms used herein have the same meaning as commonly understood by one of ordinary skill in the art.

As used herein, the singular forms "a", "an" and "the" include plural referents unless the context clearly dictates otherwise. The use of "or" or "and" means "and/or" unless stated otherwise.

The term "about" as used herein when referring to a measurable value such as an amount, a temporal duration and the like, is encompasses variations of up to ±10% from the specified value. Unless otherwise indicated, all numbers expressing quantities of ingredients, properties such as molecular weight, reaction conditions, etc., used herein are to be understood as being modified by the term "about".

The terms "activin receptor-like kinase 2," "ALK2," and "Alk2" are used interchangeably herein and refer to a transmembrane serine-threonine kinase receptor which activates downstream cell signaling upon binding to bone morphogenic proteins (BMPs). The term "ALK2" refers to any functional variants or isoforms of ALK2 which are naturally expressed by cells. The amino acid sequences of murine ALK2, human ALK2, and the extracellular domain of human ALK2 are set forth below. The ACVR1 gene encodes the protein ALK2.

Murine ALK2: (signal peptide is underlined)
(SEQ ID NO: 1)
MVDGVMILPVLMMMAFPSPSVEDEKPKVNQKLYMCVCEGLSCGNEDHCEG

QQCFSSLSINDGFHVYQKGCFQVYEQGKMTCKTPPSPGQAVECCQGDWCN

RNITAQLPTKGKSFPGTQNFHLEVGLIILSVVFAVCLLACILGVALRKFK

RRNQERLNPRDVEYGTIEGLITTNVGDSTLAELLDHSCTSGSGSGLPFLV

QRTVARQITLLECVGKGRYGEVWRGSWQGENVAVKIFSSRDEKSWFRETE

LYNTVMLRHENILGFIASDMTSRHSSTQLWLITHYHEMGSLYDYLQLTTL

DTVSCLRIVLSIASGLAHLHIEIFGTQGKSAIAHRDLKSKNILVKKNGQC

CIADLGLAVMHSQSTNQLDVGNNPRVGTKRYMAPEVLDETIQVDCFDSYK

RVDIWAFGLVLWEVARRMVSNGIVEDYKPPFYDVVPNDPSFEDMRKVVCV

DQQRPNIPNRWFSDPTLTSLAKLMKECWYQNPSARLTALRIKKTLTKIDN

SLDKLKTDC

Human ALK2 (signal peptide is underlined):
(SEQ ID NO: 2)
MVDGVMILPVLIMIALPSPSMEDEKPKVNPKLYMCVCEGLSCGNEDHCEG

QQCFSSLSINDGFHVYQKGCFQVYEQGKMTCKTPPSPGQAVECCQGDWCN

RNITAQLPTKGKSFPGTQNFHLEVGLIILSVVFAVCLLACLLGVALRKFK

RRNQERLNPRDVEYGTIEGLITTNVGDSTLADLLDHSCTSGSGSGLPFLV

QRTVARQITLLECVGKGRYGEVWRGSWQGENVAVKIFSSRDEKSWFRETE

LYNTVMLRHENILGFIASDMTSRHSSTQLWLITHYHEMGSLYDYLQLTTL

DTVSCLRIVLSIASGLAHLHIEIFGTQGKPAIAHRDLKSKNILVKKNGQC

CIADLGLAVMHSQSTNQLDVGNNPRVGTKRYMAPEVLDETIQVDCFDSYK

RVDIWAFGLVLWEVARRMVSNGIVEDYKPPFYDVVPNDPSFEDMRKVVCV

DQQRPNIPNRWFSDPTLTSLAKLMKECWYQNPSARLTALRIKKTLTKIDN

SLDKLKTDC

Extracellular domain of human ALK2 (without signal peptide):
(SEQ ID NO: 3)
MEDEKPKVNPKLYMCVCEGLSCGNEDHCEGQQCFSSLSINDGFHVYQKGC

FQVYEQGKMTCKTPPSPGQAVECCQGDWCNRNITAQLPTKGKSFPGTQNF

HLE

The term "antibody" as used herein refers to polypeptides comprising at least one antibody derived antigen binding site (e.g., VH/VL region or Fv, or CDR), and includes whole antibodies and any antigen binding fragments (i.e., "antigen-binding portions") or single chains thereof. Antibodies include known forms of antibodies. For example, the antibody can be a human antibody, a humanized antibody, a bispecific antibody, or a chimeric antibody. A whole "antibody" refers to a glycoprotein comprising at least two heavy (H) chains and two light (L) chains inter-connected by disulfide bonds, in which each heavy chain is comprised of a heavy chain variable region (abbreviated herein as $V_H$) and a heavy chain constant region; and each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

The term "antigen-binding portion" of an antibody, as used herein, refers to one or more fragments of an antibody that retain the ability to specifically bind to an antigen (e.g., ALK2), e.g., a Fab, Fab'2, scFv, SMIP, affibody, nanobody, or a domain antibody. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). In one embodiment of the invention, the formulation contains an antigen-binding portions described in U.S. Pat. Nos. 6,090,382 and 6,258,562, each incorporated by reference herein.

The term "monoclonal antibody," as used herein, includes an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. The monoclonal antibodies to be used in accordance with the formulations disclosed herein may be made by the hybridoma method first described by Kohler, et al., (1975) Nature 256: 495 or other methods known in the art. A "polyclonal antibody" is an antibody which was produced among or in the presence of one or more other, non-identical antibodies. In general, polyclonal antibodies are produced from B-lymphocytes in the presence of several other B-lymphocytes which produced non-identical antibodies. Usually, polyclonal antibodies are obtained directly from an immunized animal.

A "human" antibody (HuMAb) refers to an antibody having variable regions in which the framework and CDR regions are derived from human germline immunoglobulin sequences.

A "humanized" antibody refers to an antibody in which some, most or all of the amino acids outside the CDR domains of a non-human antibody are replaced with corresponding amino acids derived from human immunoglobulins.

A "chimeric antibody" refers to an antibody in which the variable regions are derived from one species and the constant regions are derived from another species, such as an antibody in which the variable regions are derived from a mouse antibody and the constant regions are derived from a human antibody.

An "isolated" antibody or antigen binding fragment is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes.

An "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL).

An "antigen" is an entity (e.g., a proteinaceous entity or peptide) to which an antibody binds.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

As used herein, "isotype" refers to the antibody class (e.g., IgG1, IgG2, IgG3, IgG4, IgM, IgA1, IgA2, IgD, and IgE antibody) that is encoded by the heavy chain constant region genes.

A "native sequence Fc region" or "native sequence Fc" comprises an amino acid sequence that is identical to the amino acid sequence of an Fc region found in nature.

The term "pharmaceutical formulation" refers to preparations which are in such form as to permit the biological activity of the active ingredients to be unequivocally effective, and which contain no additional components which are significantly toxic to the subjects to which the formulation would be administered.

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than 500 nM, such as approximately less than 250 nM, 100 nM, 50 nM, 10 nM, 1 nM, or 100 pM or even lower when determined by, e.g., surface plasmon resonance (SPR) technology in a BIACORE® 2000 surface plasmon resonance instrument using the predetermined antigen, e.g., recombinant human ALK2, as the analyte and the antibody as the ligand, bio-layer interferometry, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, unless otherwise indicated, an antibody that "specifically binds to human ALK2" refers to an antibody that binds to soluble or cell bound human ALK2 with a $K_D$ of 500 nM or less, such as approximately less than 250 nM, 100 nM, 50 nM, 10 nM, 1 nM, or 100 pM, or even lower.

The term "epitope" or "antigenic determinant" refers to a site on an antigen to which an immunoglobulin or antibody specifically binds. Epitopes can be formed both from contiguous amino acids (usually a linear epitope) or noncontiguous amino acids juxtaposed by tertiary folding of a protein (usually a conformational epitope).

The term "binds to the same epitope" with reference to two or more antibodies means that the antibodies bind to the same segment of amino acid residues, as determined by a given method. Techniques for determining whether an antibody binds to the same epitope as another antibody include, for example, epitope mapping methods, such as, x-ray analyses of crystals of antigen: antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same heavy and light chain CDR1, 2 and 3 sequences are expected to bind to the same epitope.

Antibodies that "compete with another antibody for binding to a target" refer to antibodies that inhibit (partially or completely) the binding of the other antibody to the target. In certain embodiments, an antibody competes with, and inhibits binding of another antibody to a target by at least 10%, 20%, 30%, 40%, 50%, 60%, 70%, 80%, 90% or 100%.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnsson, B., et al. (1991) *Anal. Biochem.* 198:268-277.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. Preferred methods for determining the $K_D$ of an antibody are by using surface plasmon resonance, preferably using a biosensor system such as a Biacore system, bio-layer interferometry, flow cytometry, and Scatchard analysis.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "nucleic acid molecule," as used herein, is intended to include DNA molecules and RNA molecules. A nucleic acid molecule may be single-stranded or double-stranded, and may be cDNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, other forms of expression vectors, such as viral vectors (e.g., replication defective retroviruses, adenoviruses and adeno-associated viruses), which serve equivalent functions are also contemplated.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

Also provided are "conservative sequence modifications" of the sequences set forth herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and)(BLAST programs (version 2.0) of Altschul, et al. (1990)*J Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the) (BLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g.,)(BLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

Nucleic acids, e.g., cDNA, may be mutated, in accordance with standard techniques, to provide gene sequences. For coding sequences, these mutations may affect the corresponding amino acid sequence as desired. In particular, DNA sequences substantially homologous to or derived from native V, D, J, constant, switches and other such sequences described herein are contemplated (where "derived" indicates that a sequence is identical or modified from another sequence).

The term "inhibition" as used herein, refers to any statistically significant decrease in biological activity, including partial and full blocking of the activity. For example, "inhibition" can refer to a statistically significant decrease of about 10%, 20%, 30%, 40%, 50%, 60%, 70%, 80%, 90%, 95%, 96%, 97%, 98%, 99%, or 100% in biological activity.

The terms "treat," "treating," and "treatment," as used herein, refer to therapeutic measures described herein. The methods of "treatment" employ administration to a subject the combination disclosed herein in order to cure, delay, reduce the severity of, or ameliorate, one or more symptoms of the disease or disorder or recurring disease or disorder, or in order to prolong the survival of a subject beyond that expected in the absence of such treatment.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

The terms "effective amount" or "therapeutically effective amount" are used interchangeably, and refer to an amount of formulation or antibody effective to alleviate or ameliorate symptoms of disease or to prolong the survival of the subject being treated. Determination of a therapeutically effective amount is within the capability of those skilled in the art, especially in light of the detailed disclosure provided herein. Therapeutically effective dosages may be determined by using in vitro and in vivo methods.

As used herein, the term "chronically" (e.g., to chronically administer a compound), or similar terms, refers to a method of administration in which an agent (e.g., an anti-ALK2 antibody) is administered to a subject in an amount and with a frequency sufficient to maintain an effective amount of the agent in the subject for at least seven (e.g., at least eight, nine, 10, 11, 12, 13, 14, 15, 16, 17, 18, 19, 20, 21, 22, 23, 24). In some embodiments, an agent can be chronically administered to a subject for at least one (e.g., at least two, three, four, five, or six) month(s). In some embodiments, an agent can be chronically administered to a subject for a year or more.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intra-arterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually, or topically. Administering can also be performed, for example, once, a plurality of times, and/or over one or more extended periods.

As used herein, the terms "inhibits" or "blocks" (e.g., referring to inhibition/blocking of ALK2 binding or activity) are used interchangeably and encompass both partial and complete inhibition/blocking.

Various aspects described herein are described in further detail in the following subsections.

I. Anti-ALK2 Antibodies

Provided herein are anti-ALK2 antibodies, and antigen-binding fragments thereof, that are characterized by particular structural and/or functional features.

In one aspect, the anti-ALK2 antibodies described herein exhibit one or more of the following properties:
  a) binds to both mouse and human ALK2;
  b) binds to ALK2 expressed on at least one of osteoblasts, osteoclasts, and/or progenitor cells (i.e., fibro-adipogenic progenitors (FAP));
  c) stimulates bone mineralization;
  d) increases bone mineral density;
  e) inhibits stimulation of ALK2 by BMP ligands; and
  f) inhibits downstream ALK2-mediated BMP signaling by SMAD proteins.

In some embodiments, the anti-ALK2 antibodies exhibit 2 or more, 3 or more, 4 or more, 5 or more, or all 6, of the above properties. In some embodiments, the anti-ALK2 antibodies have been determined to exhibit 2 or more, 3 or more, 4 or more, 5 or more, or all 6, of the above properties.

In some embodiments, the anti-ALK2 antibodies described herein bind to human ALK2 with a $K_D$ of about 500 nM or less, 250 nM or less, 200 nM or less, 150 nM or less, 100 nM or less, 50 nM or less, 25 nM or less, 10 nM or less, 1 nM or less, 500 pM or less, 100 pM or less, 50 pM or less, 25 pM or less, 10 pM or less, 1 pM or less, 1 pM to 500 nM, 10 pM to 500 nM, 100 pM to 500 nM, 1 nM to 500 nM, 50 pM to 500 nM, 100 pM to 500 nM, 1 nM to 250 nM, 1 nM to 200 nM, 50 nM to 500 nM, 50 nM to 250 nM, 50 nM to 200 nM, 100 nM to 500 nM, 150 nM to 500 nM, 100 nM to 250 nM, 150 nM to 500 nM, 150 nM to 250 nM, or 150 nM to 200 nM.

In some embodiments, the anti-ALK2 antibodies described herein bind to human ALK2, as assessed by surface plasmon resonance, with a $K_D$ of about 500 nM or less, 250 nM or less, 200 nM or less, 150 nM or less, 100 nM or less, 50 nM or less, 25 nM or less, 10 nM or less, 1 nM or less, 1 pM to 500 nM, 10 pM to 500 nM, 100 pM to 500 nM, 1 nM to 500 nM, 10 nM to 500 nM, 100 nM to 500 nM, or 100 nM to 250 nM.

In some embodiments, the anti-ALK2 antibodies described herein bind to ALK2 expressed on osteoblasts, osteoclasts, and/or progenitor cells (e.g., fibro-adipogenic progenitors), as assessed by, e.g., flow cytometry.

In some embodiments, the anti-ALK2 antibodies described herein stimulate bone mineralization. In some embodiments, the anti-ALK2 antibodies described herein simulate bone mineralization in mature bone. In some embodiments, the anti-ALK2 antibodies described herein simulate bone mineralization and an increase in bone density. For example, the anti-ALK2 antibodies stimulate bone mineralization by 1% or more, 5% or more, 10% or more, 20% or more, or 25% or more, from baseline, as measured, e.g., using dual-energy x-ray absorptiometry (DEXA). In some embodiments, the anti-ALK2 antibodies stimulate bone mineralization by 8% or more from baseline. In some embodiments, the anti-ALK2 antibodies stimulate bone mineralization in osteoblasts.

In some embodiments, the anti-ALK2 antibodies described herein increase bone mineral density. For example, the anti-ALK2 antibodies stimulate bone mineralization and thus bone density, by 1% or more, 5% or more, 10% or more, 20% or more, or by 25% or more, from baseline, as measured, e.g., using DEXA.

In certain embodiments, the anti-ALK2 antibodies described herein inhibit the stimulation of ALK2 by BMP ligands. For example, the anti-ALK2 antibodies inhibit the stimulation of ALK2 by BMP ligands by 10% or more, 20% or more, 30% or more, 40% or more, 50% or more, 60% or more, 70% or more, 80% or more, 90% or more, 95% or more, or by 100%, for example, as assessed, e.g., using a cell-based reporter assay (e.g., BRE-luciferase assay).

In certain embodiments, the anti-ALK2 antibodies described herein inhibit downstream BMP signaling by SMAD proteins. For example, the anti-ALK2 antibodies inhibit downstream BMP signaling by SMAD proteins by 10% or more, 20% or more, 30% or more, 40% or more, 50% or more, 60% or more, 70% or more, 80% or more, 90% or more, 95% or more, or by 100%, as assessed, e.g., by Western blot analysis of lysates from cells treated with the anti-ALK2 antibodies using phospho-specific SMAD antibodies.

Also provided herein are anti-ALK2 antibodies which compete for binding to ALK2 (e.g., human ALK2) with the anti-ALK2 antibodies described herein. Also provided are anti-ALK2 antibodies which bind to the same epitope on ALK2 (e.g., human ALK2) as the anti-ALK2 antibodies described herein.

An antibody that exhibits one or more of the above-mentioned functional properties (e.g., biochemical, immunochemical, cellular, physiological or other biological activities, or the like) as determined according to methodologies known to the art and described herein, will be understood to relate to a statistically significant difference in the particular activity relative to that seen in the absence of the antibody (e.g., or when a control antibody of irrelevant specificity is present). Preferably, anti-ALK2 antibody-induced increases in a measured parameter effects a statistically significant increase by at least 10% of the measured parameter, more preferably by at least 20%, 30%, 40%, 50%, 60%, 70%, 80%, 90%, 95%, 100% (i.e., 2 fold), 3 fold, 5 fold or 10 fold, and in certain preferred embodiments, an antibody described herein may increase the measured parameter by greater than 92%, 94%, 95%, 97%, 98%, 99%, 100% (i.e., 2 fold), 3 fold, 5 fold or 10 fold. Conversely, anti-ALK2 antibody-induced decreases in a measured parameter effects a statistically significant decrease by at least 10% of the measured parameter, more preferably by at least 20%, 30%, 40%, 50%, 60%, 70%, 80% or 90%, and in certain preferred embodiments, an antibody described herein may decrease the measured parameter by greater than 92%, 94%, 95%, 97%, 98% or 99%.

Standard assays to evaluate the binding ability of the antibodies toward human ALK2 are known in the art, including for example, ELISAs, Western blots, and RIAs. Suitable assays are also described in detail in the Examples. The binding kinetics (e.g., binding affinity) of the antibodies also can be assessed by standard assays known in the art, such as by surface plasmon resonance (Biacore analysis) and bio-layer interferometry. Assays to evaluate the effects of the antibodies on functional properties of ALK2 are described in further detail infra and in the Examples.

Also provided herein are anti-ALK2 antibodies defined by particular structural features. Accordingly, in one aspect, provided herein are isolated antibodies, or antigen binding portions thereof, which bind to ALK2 and comprise heavy and light chain variable regions, wherein the heavy chain variable region comprises an amino acid sequence selected from the group consisting of SEQ ID NOs: 16, 26, 36, and 46.

In another aspect, provided herein are isolated antibodies, or antigen binding portions thereof, which bind to ALK2 and comprise heavy and light chain variable regions, wherein the light chain variable region comprises an amino acid sequence selected from the group consisting of SEQ ID NOs: 17, 27, 37, and 47.

In another aspect, provided herein are isolated antibodies, or antigen binding portions thereof, which bind to ALK2 and comprise the three variable heavy chain CDRs and the three light chain CDRs that are in the variable heavy chain and variable light chain pairs selected from the group consisting of:
(a) SEQ ID NOs: 16 and 17, respectively;
(b) SEQ ID NOs: 26 and 27, respectively;
(c) SEQ ID NOs: 36 and 37, respectively; and
(d) SEQ ID NOs: 46 and 47, respectively.

In another aspect, provided herein are isolated antibodies, or antigen binding portions thereof, which bind to ALK2, comprising:
(a) heavy chain CDR1, CDR2, and CDR3 sequences comprising SEQ ID NOs: 10, 11, and 12, respectively, and/or light chain CDR1, CDR2, and CDR3 sequences comprising SEQ ID NOs: 13, 14, and 15, respectively;
(b) heavy chain CDR1, CDR2, and CDR3 sequences comprising SEQ ID NOs: 20, 21, and 22, respectively, and/or light chain CDR1, CDR2, and CDR3 sequences comprising SEQ ID NOs: 23, 24, and 25, respectively;
(c) heavy chain CDR1, CDR2, and CDR3 sequences comprising SEQ ID NOs: 30, 31, and 32, respectively, and/or light chain CDR1, CDR2, and CDR3 sequences comprising SEQ ID NOs: 33, 34, and 35, respectively; or
(d) heavy chain CDR1, CDR2, and CDR3 sequences comprising SEQ ID NOs: 40, 41, and 42, respectively, and/or light chain CDR1, CDR2, and CDR3 sequences comprising SEQ ID NOs: 43, 44, and 45, respectively.

In another aspect, provided herein are isolated antibodies, or antigen binding portions thereof, which bind to ALK2, comprising:
(a) heavy and light chain variable region sequences comprising SEQ ID NOs: 16 and 17, respectively;
(b) heavy and light chain variable region sequences comprising SEQ ID NOs: 26 and 27, respectively;
(c) heavy and light chain variable region sequences comprising SEQ ID NOs: 36 and 37, respectively; or
(d) heavy and light chain variable region sequences comprising SEQ ID NOs: 46 and 47, respectively.

In some embodiments, the anti-ALK2 antibody comprises a heavy chain and/or light chain variable region sequence that is at least 80%, 85%, 90%, 95%, 96%, 97%, 98%, or 99% identical to the heavy chain and/or light chain variable region sequences of any of subparts (a)-(d) above. In some embodiments, the heavy chain and/or light chain variable region sequences of any of subparts (a)-(d) above has 1, 2, 3, 4, 5, 1-2, 1-3, 1-4, or 1-5 amino acid substitutions (e.g., conservative amino acid substitutions). These anti-ALK2 antibodies can be tested for various functional properties (e.g., binding to ALK2, stimulation of bone mineralization, effects on bone mineral density, inhibition of ALK2 stimulation by BMP ligands, and inhibition of downstream BMP signaling by SMAD proteins) using the assays and animal models described herein.

In some embodiments, the anti-ALK2 antibody comprises the heavy chain variable region sequence of any of subparts (a)-(d) above, and a constant region, e.g., a human IgG constant region (e.g., IgG1, IgG2, IgG3, or IgG4, or variants thereof (e.g., variants comprising Fc regions with reduced or no effector function)). In some embodiments, the constant region is a human IgG1 constant region comprising the amino acid sequence set forth in SEQ ID NO: 8. In some embodiments, the constant region is a hybrid IgG2/IgG4 constant region comprising the amino acid sequence set forth in SEQ ID NO: 9. In some embodiments, the heavy chain variable region sequences of any of subparts (a)-(d) above may be linked to a constant domain to form a heavy chain (e.g., a full length heavy chain). Similarly, the light chain variable region sequences of any of subparts (a)-(d) above may be linked to a constant region to form a light chain (e.g., a full length light chain). A full length heavy chain (with the exception of the C-terminal lysine (K) or with the exception of the C-terminal glycine and lysine (GK), which may be absent or removed) and full length light chain combine to form a full length antibody.

In another aspect, provided herein are isolated antibodies, or antigen binding portions thereof, which bind to ALK2, comprising:
(a) heavy and light chain sequences comprising SEQ ID NOs: 18 and 19, respectively;
(b) heavy and light chain sequences comprising SEQ ID NOs: 28 and 29, respectively;
(c) heavy and light chain sequences comprising SEQ ID NOs: 38 and 39, respectively; or
(d) heavy and light chain sequences comprising SEQ ID NOs: 48 and 49, respectively.

In some embodiments, the full length heavy chain lacks the C-terminal lysine residue (which may be absent or removed).

In some embodiments, the anti-ALK2 antibody comprises a heavy chain and/or light chain sequence that is at least 80%, 85%, 90%, 95%, 96%, 97%, 98%, 99%, 99.5%, or 99.7% identical to the heavy chain and/or light chain sequences of any of subparts (a)-(d) above. In some embodiments, the heavy chain and/or light chain sequences of any of subparts (a)-(d) above has 1, 2, 3, 4, 5, 1-2, 1-3, 1-4, or 1-5 amino acid substitutions (e.g., conservative amino acid substitutions). These anti-ALK2 antibodies can be tested for various functional properties (e.g., binding to ALK2, stimulation of bone mineralization, effects on bone mineral density, inhibition of ALK2 stimulation by BMP ligands, and inhibition of downstream BMP signaling by SMAD proteins) using the assays and animal models described herein.

The anti-ALK2 antibodies disclosed herein include all known forms of antibodies and other protein scaffolds with antibody-like properties. For example, the antibody can be a humanized antibody, human antibody, bispecific antibody, an immunoconjugate, a chimeric antibody, or a protein scaffold with antibody-like properties, such as fibronectin or ankyrin repeats. The antibody also can be a Fab, Fab'2, scFv, affibody, avimer, nanobody, or a domain antibody. Full-length antibodies can be prepared from $V_H$ and $V_L$ sequences using standard recombinant DNA techniques and nucleic acids encoding the desired constant region sequences can be operatively linked to the variable region sequences.

In some embodiments, the heavy and light chains, or portions thereof, of the anti-ALK2 antibodies described herein (e.g., those provided in Table 6), may be linked to a signal sequence. For example, the heavy chains or variable regions thereof (e.g., SEQ ID NOs: 16, 18, 26, 28, 36, 38, 46, and 48), or light chains or variable regions thereof (e.g., SEQ ID NOs: 17, 19, 27, 29, 37, 39, 47, and 49), may be linked or fused to a signal peptide comprising or consisting of

MGWSCIILFLVATATGVHS.           (SEQ ID NO: 50)

In some embodiments, the anti-ALK2 antibodies described herein have reduced effector function, e.g., reduced effector function relative to a second antibody which has effector function (e.g., an antibody which has a native sequence Fc or constant region), or lack effector function. A native sequence Fc or constant region comprises an amino acid sequence identical to the amino acid sequence of an Fc or constant chain region found in nature. A variant or altered Fc or constant region comprises an amino acid sequence which differs from that of a native sequence heavy chain region by virtue of at least one amino acid modification, insertion, or deletion. In some embodiments, the variant or altered constant region has at least one amino acid substitution, insertion, and/or deletion, compared to a native sequence constant region or to the constant region of a parent polypeptide, e.g. from about 1 to about 100 amino acid substitutions, insertions, and/or deletions in a native sequence constant region or in the constant region of the parent polypeptide. In some embodiments, the variant or altered constant region herein will possess at least about 70% homology (similarity) or identity with a native sequence constant region and/or with a constant region of a parent polypeptide, and in some instances at least about 75% and in other instances at least about 80% homology or identity therewith, and in other embodiments at least about 85%, 90%, 95%, 96%, 97%, 98%, 99%, or 99.5% homology or identity therewith. The variant or altered constant region may also contain one or more amino acid deletions or insertions, such as 1, 2, 3, 4, 5, 6, 7, 8, 9, 10, 1-2, 1-3, 1-4, 1-5, 1-6, 1-7, 1-8, 1-9, 1-10, 2-5, or 5-10 amino acid deletions or insertions. Additionally, the variant constant region may contain one or more amino acid substitutions, deletions, or insertions, e.g., 1, 2, 3, 4, 5, 6, 7, 8, 9, 10, 1-2, 1-3, 1-4, 1-5, 1-6, 1-7, 1-8, 1-9, 1-10, 2-5, or 5-10 amino acid substitutions, deletions or insertions, that results in altered post-translational modifications, including, for example, an altered glycosylation pattern.

Antibodies with reduced or no effector function may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g. glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, 2$^{nd}$ Edition," Cold Spring Harbor Laboratory Press, Cold Spring Harbor, N.Y.; Harlow and Lane (1988); Borrebaek, *Antibody Engineering—A practical guide* (1992); Johne et al., *J Immunol Methods* 160:191-198 (1993), in International Publication No. WO 06/53301; and U.S. Pat. No. 7,704,497.

In some embodiments, the anti-ALK2 antibodies comprise a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):44'-452). For example (and in accordance with Kabat numbering), the IgG1 and IgG4 constant regions contain $G_{249}G_{250}$ residues whereas the IgG2 constant region does not contain residue 249, but does contain $G_{250}$. In a G2/G4 hybrid constant region, where the 249-250 region comes from the G2 sequence, the constant region can be further modified to introduce a glycine residue at position 249 to produce a G2/G4 fusion having $G_{249}/G_{250}$. An exemplary G2/G4 hybrid constant region is described in U.S. Pat. No. 8,075,884. For example, in one embodiment, the G2/G4 hybrid constant region comprises the amino acid sequence set forth in SEQ ID NO: 9.

In addition to using a G2/G4 construct as described above, anti-ALK2 antibodies with reduced effector function may be produced by introducing other types of changes in the amino acid sequence of certain regions of the antibody. Such amino acid sequence changes include but are not limited to the Ala-Ala mutation described in, e.g., International Publication Nos. WO 94/28027 and WO 98/47531; and Xu et al. (2000) *Cell Immunol* 200:16-26. Thus, in some embodiments, anti-ALK2 antibodies with mutations within the constant region including the Ala-Ala mutation may be used to reduce or abolish effector function. According to these embodiments, the constant region of an anti-ALK2 antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-ALK2 antibody comprises an IgG4 framework, wherein the Ala- Ala mutation would describe a mutation(s) from phenylalanine to alanine at position 234 and/or a mutation from leucine to alanine at position 235. In another embodiment, the anti-ALK2 antibody comprises an IgG 1 framework, wherein the Ala-Ala mutation would describe a mutation(s) from leucine to alanine at position 234 and/or a mutation from leucine to alanine at position 235. An anti-ALK2 antibody may alternatively or additionally carry other mutations, including the point mutation K322A in the CH2 domain (Hezareh et al. (2001) *J Virol* 75:12161-8).

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al.) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669.

Changes within the hinge region also affect effector functions. For example, deletion of the hinge region may reduce affinity for Fc receptors and may reduce complement activation (Klein et al. 1981 *PNAS USA* 78: 524-528). The present disclosure therefore also relates to antibodies with alterations in the hinge region.

In some embodiments, anti-ALK2 antibodies may be modified to inhibit complement dependent cytotoxicity (CDC). Modulated CDC activity may be achieved by introducing one or more amino acid substitutions, insertions, or deletions in an Fc region of the antibody (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have altered internalization capability and/or decreased complement-mediated cell killing. See Caron et al., *J Exp Med.* 176:1191-1195 (1992) and Shopes, B. *J. Immunol.* 148:2918-2922 (1992), WO 99/51642, Duncan & Winter, *Nature* 322: 738-40 (1988); U.S. Pat. Nos. 5,648,260; 5,624,821; and WO 94/29351.

In some embodiments, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. Unless otherwise specified throughout the specification, numbering of the residues in the Fc region is that of the EU index as in Kabat (WO 00/42072). The effector ligand to which affinity is altered can be, for example, an Fc receptor or the C1 component of complement (see, e.g., U.S. Pat. Nos. 5,624,821 and 5,648,260). In another embodiment, one or more amino acids selected from amino acid residues 329, 331 and 322 can be replaced with a different amino acid residue such that the antibody has altered C1q binding and/or reduced or abolished complement dependent cytotoxicity (CDC) (see, e.g., U.S. Pat. No. 6,194,551). In another example, one or more amino acid residues within amino acid positions 231 and 239 are altered to thereby alter the ability of the antibody to fix complement (see, e.g., International Publication WO 94/29351).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, *Current Opinion in Biotechnology* 20:685-691 (2009).

Optionally, the Fc region may comprise a non-naturally occurring amino acid residue at additional and/or alternative positions known to one skilled in the art (see, e.g.; U.S. Pat. Nos. 5,624,821; 6,277,375; 6,737,056; 6,194,551; 7,317, 091; 8,101,720; International Publication Nos. WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

In certain embodiments, the antibody is modified to increase its biological half-life. For example, this may be done by increasing the binding affinity of the Fc region for FcRn. For example, one or more of more of following residues can be mutated: 252, 254, 256, 433,435, and/or 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434H, 434F, 434Y, and 434M. Other variants that increase Fc binding to FcRn include: 250E, 250Q, 428L, 428F, 250Q/428L, (Hinton et al., 2004, *J. Biol. Chem,* 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, *J Biol Chem,* 2001, 276(9):6591-6604), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall'Acqua et al., *J. Immunol.,* 2002, 169:5171-5180, Dall'Acqua et al., 2006, *J. of Biol. Chem.* 281:23514-23524). Other modifications for modulating FcRn binding are described in Yeung et al., 2010*J Immunol,* 182:7663-7671. In certain embodiments, hybrid IgG isotypes with particular biological characteristics may be used. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, 236G (referring to an insertion of a glycine at position 236), and 327A.

In some embodiments, an Fc is chosen that has reduced binding to FcγRs. An exemplary Fc, e.g., IgG1 Fc, with reduced FcγR binding comprises the following three amino acid substitutions: L234A, L235E and G237A. In some embodiments, an Fc is chosen that has reduced complement fixation. An exemplary Fc, e.g., IgG1 Fc, with reduced complement fixation has the following two amino acid substitutions: A330S and P331S. In some embodiments, an Fc is chosen that has essentially no effector function, i.e., it has reduced binding to FcγRs and reduced complement fixation. An exemplary effectorless Fc (e.g., IgG1 Fc) comprises the following five mutations: L234A, L235E, G237A, A330S and P331S.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) *TIBTECH* 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) *Immunology* 89(4):573-578; Newkirk et al. (1996) *Clin Exp Immunol* 106(2):259-64. A as known alterations that affect effector function include modifications in the glycosylation pattern or a change in the number of glycosylated residues, the present disclosure relates to a ALK2 antibody wherein glycosylation is altered to decrease effector function(s) including ADCC and CDC. Altered glycosylation includes a decrease in the number of glycosylated residues as well as a change in the pattern or location of glycosylated residues.

II. Antibodies which Bind to Same Epitope as or Cross-Compete with Anti-ALK2 Antibodies Anti-ALK2 antibodies which bind to the same or similar epitopes to the antibodies disclosed herein (and thus also cross-compete with the antibodies disclosed herein) may be raised using immunization protocols. The resulting antibodies can be screened for high affinity binding to ALK2 (e.g., human ALK2). Selected antibodies can then be studied, e.g., in yeast display assay in which sequence variants of ALK2 are presented on the surface of yeast cells, or by hydrogen-deuterium exchange experiments, to determine the precise epitope bound by the antibody.

The epitope to which an antibody binds can be determined using art-recognized methods. An anti-ALK2 antibody is considered to bind to the same epitope as a reference anti-ALK2 antibody if it, e.g., contacts one or more of the same residues on ALK2 as the reference antibody; contacts one or more of the same residues within at least one region of ALK2 as the reference antibody; contacts a majority of residues within at least one region of ALK2 as the reference antibody; contacts a majority of the same residues within each region of ALK2 as the reference antibody; contacts a majority of the same residues along the entire length of ALK2 as the reference antibody; contacts all of the same distinct regions of ALK2 as the reference antibody; contacts all of the same residues at any one region on ALK2 as the reference antibody; or contacts all of the same residues at all of the same regions of ALK2 as the reference antibody.

Techniques for determining antibodies that bind to the "same epitope on ALK2" with the anti-ALK2 antibodies described herein include x-ray analyses of crystals of antigen:antibody complexes, which provide atomic resolution of the epitope. Other methods monitor the binding of the antibody to antigen fragments or mutated variations of the antigen where loss of binding due to an amino acid modification within the antigen sequence indicates the epitope component. Methods may also rely on the ability of an antibody of interest to affinity isolate specific short peptides (either in native three dimensional form or in denatured form) from combinatorial phage display peptide libraries or from a protease digest of the target protein. The peptides are then regarded as leads for the definition of the epitope corresponding to the antibody used to screen the peptide library. For epitope mapping, computational algorithms have also been developed that have been shown to map conformational discontinuous epitopes.

The epitope or region comprising the epitope can also be identified by screening for binding to a series of overlapping peptides spanning ALK2. Alternatively, the method of Jespers et al. (1994) *Biotechnology* 12:899 may be used to guide the selection of antibodies having the same epitope and therefore similar properties to the anti-ALK2 antibodies described herein. Using phage display, first, the heavy chain of the anti-ALK2 antibody is paired with a repertoire of (e.g., human) light chains to select a ALK2-binding antibody, and then the new light chain is paired with a repertoire of (e.g., human) heavy chains to select a (e.g., human) ALK2-binding antibody having the same epitope or epitope region as an anti-ALK2 antibody described herein. Alternatively, variants of an antibody described herein can be obtained by mutagenesis of cDNA sequences encoding the heavy and light chains of the antibody.

Alanine scanning mutagenesis, as described by Cunningham & Wells (1989) *Science* 244: 1081, or some other form of point mutagenesis of amino acid residues in ALK2 may also be used to determine the functional epitope for an anti-ALK2 antibody.

The epitope or epitope region (an "epitope region" is a region comprising the epitope or overlapping with the epitope) bound by a specific antibody may also be determined by assessing binding of the antibody to peptides comprising ALK2 fragments. A series of overlapping peptides encompassing the ALK2 sequence may be synthesized and screened for binding, e.g. in a direct ELISA, a competitive ELISA (where the peptide is assessed for its ability to prevent binding of an antibody to ALK2 bound to a well of a microtiter plate), or on a chip. Such peptide screening methods may not be capable of detecting some discontinuous functional epitopes.

An epitope may also be identified by MS-based protein footprinting, such as HDX-MS and Fast Photochemical Oxidation of Proteins (FPOP), structural methods such as X-ray crystal structure determination, molecular modeling, and nuclear magnetic resonance spectroscopy.

III. Nucleic Acids

Also provided herein are nucleic acid molecules that encode the anti-ALK2 antibodies described herein. The nucleic acids may be present in whole cells, in a cell lysate, or in a partially purified or substantially pure form. Accordingly, also provided herein are host cells comprising these nucleic acid molecules, as well as expression vectors comprising these nucleic acid molecules. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, provided herein are nucleic acid molecules that encode the VH and/or VL sequences, or heavy and/or light chain sequences, of any of the anti-ALK2 antibodies described herein. For example, in some embodiments, provided are nucleic acids comprising a nucleotide sequence selected from the group consisting of SEQ ID NOs: 64-67, 74-77, 84-87, and 94-97. In some embodiments, provided are nucleic acids encoding the heavy and/or light chain variable region, or heavy and/or light chain, or antigen-binding portion thereof, within the nucleotide sequence selected from the group consisting of SEQ ID NOs: 64-67, 74-77, 84-87, and 94-97. Host cells comprising the nucleotide sequences (e.g., nucleic acid molecules) described herein are encompassed herein.

Once DNA fragments encoding variable region segments are obtained, these DNA fragments can be further manipulated by standard recombinant DNA techniques, for example, to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification.

The heavy chain constant region can be an IgG1, IgG2, IgG3, IgG4, IgA, IgE, IgM or IgD constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991)) and DNA fragments encompassing these regions can be obtained by standard PCR amplification. The light chain constant region can be a kappa or lambda constant region.

In some embodiments, nucleic acid molecules encoding the heavy and light chain variable regions, or heavy and light chains, are present in a single expression vector. In some embodiments, nucleic acid molecules encoding the heavy and light chain variable regions, or heavy and light chains, are present in multiple expression vectors which can be introduced into a host cell together such that the heavy and light chain variable regions, or heavy and light chains, are co-expressed in the cell.

scFv genes can be created by operatively linking the VH- and VL-encoding DNA fragments to another fragment encoding a flexible linker known in the art such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Also provided herein are nucleic acid molecules with conservative substitutions (i.e., substitutions that do not alter the resulting amino acid sequence upon translation of nucleic acid molecule), e.g., for codon optimization.

IV. Methods of Production

Suitable methods for producing an antibody (e.g., an anti-ALK2 antibody), or antigen-binding fragments thereof, in accordance with the disclosure are known in the art (see, e.g., U.S. Pat. Nos. 7,427,665; 7,435,412; and 7,408,041, the disclosures of each of which are incorporated herein by reference in their entirety) and described herein. Recombinant techniques may be used to produce antibodies based on the sequence of the monoclonal antibodies.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See U.S. Pat. Nos. 5,225,539 and 7,393,648, the contents of each of which are incorporated herein by reference.

Recombinant DNA technology can be used to produce the antibodies according to established procedure, including procedures in bacterial or preferably mammalian cell culture. The selected cell culture system preferably secretes the antibody product.

In some embodiments, the process for the production of an antibody disclosed herein includes culturing a host, e.g., *E. coli* or a mammalian cell (e.g., CHO cell), which has been transformed with a hybrid vector. The vector includes one or more expression cassettes containing a promoter operably linked to a first DNA sequence encoding a signal peptide linked in the proper reading frame to a second DNA sequence encoding the antibody protein (e.g., the heavy and/or light chain variable region, or the heavy and light chain, of an anti-ALK2 antibody described herein). The antibody protein is then collected and isolated. Optionally, the expression cassette may include a promoter operably linked to a polycistronic (e.g., bicistronic) DNA sequence encoding antibody proteins each individually operably linked to a signal peptide in the proper reading frame.

Large quantities of the desired antibodies can also be obtained by multiplying mammalian cells in vivo. Multiplication of mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g., in an airlift reactor or in a continuous stirrer reactor), and immobilized or entrapped cell culture (e.g., in hollow fibers, microcapsules, on agarose microbeads or ceramic cartridges).

The foregoing, and other, techniques are discussed in, for example, Kohler and Milstein, (1975) *Nature* 256:495-497; U.S. Pat. No. 4,376,110; Harlow and Lane, *Antibodies: a Laboratory Manual*, (1988) Cold Spring Harbor, the disclosures of which are all incorporated herein by reference. Techniques for the preparation of recombinant antibody molecules are described in the above references and also in, e.g.: WO 97/08320; U.S. Pat. Nos. 5,427,908; 5,508,717; Smith (1985) *Science* 225:1315-1317; Parmley and Smith (1988) *Gene* 73:305-318; De La Cruz et al. (1988) *J. Biol. Chem.* 263:4318-4322; U.S. Pat. Nos. 5,403,484; 5,223,409; WO 88/06630; WO 92/15679; U.S. Pat. Nos. 5,780,279; 5,571,698; 6,040,136; Davis et al. (1999) *Cancer Metastasis Rev.* 18(4):421-5; and Taylor et al. (1992) *Nucleic Acids Research* 20: 6287-6295; Tomizuka et al. (2000) *Proc. Natl. Acad. Sci. USA* 97(2): 722-727, the contents of each of which are incorporated herein by reference in their entirety.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g., affinity chromatography with one or more surface polypeptides derived from a ALK2-expressing cell line or synthetic ALK2 fragment peptides, or with Protein-A or -G.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application.

The monoclonal antibodies of the present disclosure include "humanized" forms of the non-human (e.g., mouse) antibodies (e.g., humanized form of the anti-ALK2 antibodies described herein). Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257.

In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function. Such modifications can include mutations (e.g., substitutions, insertions, deletions) in the framework regions and/or CDR regions of the antibody.

Human antibodies can be made by a variety of methods known in the art, including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, the contents of which are herein incorporated by reference in their entireties. Human antibodies can also be produced using transgenic mice which express human immunoglobulin genes, and upon immunization are capable of producing a full repertoire of human antibodies in the absence of endogenous immunoglobulin production. For an overview of this technology for producing human antibodies, see, Lonberg and Huszar, 1995, Int. Rev. Immunol. 13:65-93. Phage display technology (McCafferty et al, Nature 348:552-553 (1990)) also can be used to produce human antibodies and antibody fragments in vitro, from immunoglobulin variable (V) domain gene repertoires from unimmunized donors. Human antibodies can also be generated by in vitro activated B cells (see U.S. Pat. Nos. 5,567,610 and 5,229,275, the contents of which are herein incorporated by reference in their entireties). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al, 1994, Bio/technology 12:899-903).

In certain embodiments, de-immunized anti-ALK2 antibodies are provided. De-immunized antibodies are those modified so as to render the antibody non-immunogenic, or less immunogenic, to a given species. De-immunization can be achieved by modifying the antibody utilizing any of a variety of techniques known to those skilled in the art (see, e.g., International Publication Nos. WO 04/108158 and WO 00/34317). For example, an antibody may be de-immunized by identifying potential T cell epitopes and/or B cell epitopes within the amino acid sequence of the antibody and removing one or more of the potential T cell epitopes and/or B cell epitopes from the antibody, for example, using recombinant techniques. The modified antibody may then optionally be produced and tested to identify antibodies that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., International Publication No. WO 02/069232), in vitro or in silico techniques, and biological assays or physical methods (such as, for example, determination of the binding of peptides to MHC molecules, determination of the binding of peptide: MHC complexes to the T cell receptors from the species to receive the antibody, testing of the protein or peptide parts thereof using transgenic animals with the MHC molecules of the species to receive the antibody, or testing with transgenic animals reconstituted with immune system cells from the species to receive the antibody, etc.). In various embodiments, the de-immunized antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies, and semi-synthetic antibodies.

In some embodiments, a recombinant DNA comprising an insert coding for a heavy chain variable domain and/or for a light chain variable domain of an anti-ALK2 antibody, or for a heavy chain and/or for a light chain expressing cell line is produced. The term "DNA" includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-ALK2 antibodies, or a heavy chain and/or a light chain of anti-ALK2 antibodies, can be enzymatically or chemically synthesized to contain the authentic DNA sequence coding for a heavy chain variable domain and/or for the light chain variable domain, or for a heavy chain and/or for a light chain, or a mutant thereof. A mutant of the authentic DNA is a DNA encoding a heavy chain variable domain and/or a light chain variable domain, or a heavy chain and/or a light chain, of the above-mentioned antibodies in which one or more amino acids are deleted, inserted, or exchanged with one or more other amino acids.

The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly E. coli, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an anti-ALK2 antibody or a ALK2-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods known in the art.

Accordingly, the monoclonal antibodies can be naked antibodies that are not conjugated to other agents, for example, a therapeutic agent or detectable label.

Alternatively, the monoclonal antibody can be conjugated to an agent such as, for example, at least one of a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-ALK2 antibody or an antigen-binding fragment (e.g., Fab, Fv, single-chain scFv, Fab', and F(ab')$_2$) is linked to a molecule that increases the half-life of the antibody or antigen-binding fragment.

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing selectable marker drug resistance genes such as E. coli gpt (Mulligan and Berg (1981) *Proc Natl Acad Sci USA*, 78:2072) or Tn5 neo (Southern and Berg (1982) *Mol Appl Genet.* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), polyoma virus (Deans et al. (1984) *Proc Natl Acad Sci USA* 81:1292), or SV40 virus (Lusky and Botchan (1981) *Nature* 293:79).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) *Mol Cell Biol* 3:280; Cepko et al. (1984) *Cell* 37:1053; and Kaufman (1985) *Proc Natl Acad Sci USA* 82:689.

V. Multispecific Antibodies

Also contemplated are multispecific antibodies, such as bispecific antibodies. Bispecific antibodies are monoclonal antibodies that have binding specificities for at least two different antigens. In the present case, one of the binding specificities is for the ALK2 antigen on a cell, the other one is for any other antigen, and preferably for a cell-surface protein or receptor or receptor subunit.

Methods for making multispecific antibodies, such as bispecific antibodies, are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; International Publication No. WO 96/27011; Brennan et al. (1985) *Science* 229:81; Shalaby et al. *J Exp Med* (1992) 175:217-225; Kostelny et al. (1992) *J Immunol* 148(5):1547-1553; Hollinger et al. (1993) *Proc. Natl. Acad. Sci. USA* 90:6444-6448; Gruber et al. (1994) *J Immunol* 152:5368; and Tutt et al. (1991) *J Immunol* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng* 8(10):1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific. The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., International Publication Nos. WO 08/024,188 and WO 07/024,715, the disclosures of each of which are incorporated herein by reference in their entirety.

VI. Immunoconjugates

The anti-ALK2 antibodies described herein can be modified following their expression and purification. The modifications can be covalent or non-covalent modifications. Such modifications can be introduced into the antibodies by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies.

In some embodiments, the antibodies can be conjugated to a heterologous moiety. The heterologous moiety can be, e.g., a heterologous polypeptide, a therapeutic agent (e.g., a drug), or a detectable label such as, but not limited to, a radioactive label, an enzymatic label, a fluorescent label, or a luminescent label. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the antibodies or fragments. Heterologous polypeptides also include polypeptides that are useful as diagnostic or detectable markers, for example, luciferase, green fluorescent protein (GFP), or chloramphenicol acetyl transferase (CAT). Suitable radioactive labels include, e.g., $^{32}P$, $^{33}P$, $^{14}C$, $^{125}I$, $^{131}I$, $^{135}S$, and $^{3}H$. Suitable fluorescent labels include, without limitation, fluorescein, fluorescein isothiocyanate (FITC), green fluorescence protein (GFP), DyLight 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase. Heterologous polypeptides can be incorporated into the anti-ALK2 antibodies as fusion proteins. Methods for generating nucleic acids encoding an antibody-heterologous polypeptide fusion protein are well known in the art of antibody engineering and described in, e.g., Dakappagari et al. (2006) *J Immunol* 176:426-440.

Two proteins (e.g., an anti-ALK2 antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α (2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the anti-ALK2 antibodies described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an anti-ALK2 antibody) are known in the art of protein chemistry. For example, fluorophores can be conjugated to free amino groups (e.g., of lysines) or sulfhydryl groups (e.g., cysteines) of proteins using succinimidyl (NETS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) *Handbook of Radiopharmaceuticals: Radiochemistry and Applications*, John Wiley and Sons (ISBN 0471495603).

In some embodiments, the anti-ALK2 antibodies described herein can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody (or fragment) by at least 1.5 (e.g., at least 2, 5, 10, 15, 20, 25, 30, 40, or 50 or more) fold.

In some embodiments, the anti-ALK2 antibodies described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

In some embodiments, the anti-ALK2 antibodies described herein can be conjugated to another agent that targets the antibody to bone, e.g., tetracyclines, calcein, bisphosphonates, polyaspartic acid, polyglutamic acid, amino phosphosugars, antibodies which bind to bone-specific proteins, proteins or peptides with bone cell binding domains. In some embodiments, the anti-ALK2 antibodies described herein can be conjugated to agents which further stimulate bone formation and/or growth.

VII. Compositions

Further provided are compositions, e.g., a pharmaceutical composition, containing one or a combination of anti-ALK2 antibodies or combination with antibodies to other targets, or antigen-binding portion(s) thereof, described herein, formulated together with a pharmaceutically acceptable carrier. Such compositions may include one or a combination of (e.g., two or more different) antibodies, or immunoconjugates or bispecific molecules described herein. For example, a pharmaceutical composition described herein can comprise a combination of antibodies (or immunoconjugates or bispecifics) that bind to different epitopes on the target antigen or that have complementary activities.

Pharmaceutical compositions described herein also can be administered in combination therapy, i.e., combined with other agents. For example, the combination therapy can include an anti-ALK2 antibody described herein combined with, e.g., at least one other agent which promotes bone growth, increases bone strength, and/or increases bone density. In some embodiments, therapeutic compositions disclosed herein can include other compounds, drugs, and/or agents used for the treatment of bone disorders (e.g., osteoporosis). Exemplary compounds, drugs, and/or agents that can be co-formulated with the anti-ALK2 antibodies described herein or prepared in a separate composition, include, for example, growth factors include insulin-like growth factor 1 (IGF-1), platelet-derived growth factor (PDGF), alpha and beta transforming growth factors, epidermal growth factor, bone morphogenetic proteins, leukemia inhibitory factor, and fibroblast growth factors. Other therapeutic agents that can be co-formulated with the anti-ALK2 antibodies described herein include vitamin D, calcium, bisphosphonates, calcitonin, estrogens, parathyroid hormone, osteogenin, NaF, osteoprotegerin, and statins.

When the anti-ALK2 antibody is used in combination with a second active agent, the agents can be formulated separately or together. For example, the respective pharmaceutical compositions can be mixed, e.g., just prior to administration, and administered together or can be administered separately, e.g., at the same or different times.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The compositions can be formulated according to standard methods. Pharmaceutical formulations are known, and are described in, e.g., Gennaro (2000) *Remington: The Science and Practice of Pharmacy*, 20$^{th}$ Edition, Lippincott, Williams & Wilkins (ISBN: 0683306472); Ansel et al. (1999) *Pharmaceutical Dosage Forms and Drug Delivery Systems*, 7$^{th}$ Edition, Lippincott Williams & Wilkins Publishers (ISBN: 0683305727); and Kibbe (2000) *Handbook of Pharmaceutical Excipients American Pharmaceutical Association*, 3$^{rd}$ Ed. (ISBN: 091733096X). In some embodiments, a composition can be formulated, for example, as a buffered solution at a suitable concentration and suitable for storage at 2-8° C. In some embodiments, a composition can be formulated for storage at a temperature below 0° C. (e.g., −20° C. or −80° C.).

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

In some embodiments, the anti-ALK2 antibodies described herein can be modified, e.g., with a moiety that improves its stabilization and/or retention in circulation, e.g., in blood, serum, or other tissues. The stabilization moiety can improve the stability, or retention of, the antibody by at least 1.5 (e.g., at least 2, 5, 10, 15, 20, 25, 30, 40, or 50 or more) fold.

A pharmaceutical composition described herein may also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 or 10 mg/kg, of the host body weight. For example dosages can be 1 mg/kg body weight, 3 mg/kg body weight, 5 mg/kg body weight, 10 mg/kg body weight, 20 mg/kg body weight, or within the range of 1-20 mg/kg.

In some methods, two or more monoclonal antibodies with different binding specificities are administered simultaneously. Antibody is usually administered on multiple occasions. Intervals between single dosages can be, for example, weekly, monthly, every three months or yearly. Intervals can also be irregular as indicated by measuring blood levels of antibody to the target antigen in the patient.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

An "effective dose" or "effective amount" of an anti-ALK2 antibody described herein preferably results in, for example, a statistically significant increase in bone growth, bone strength, and/or bone density, a decrease in severity of disease symptoms, an increase in frequency and duration of disease symptom-free periods, or a prevention of impairment or disability due to the disease affliction. An effective dose or effective amount of an anti-ALK2 antibody described herein may also result in a statistically significant increase in, e.g., the rate of fracture repair, reversal of bone loss in osteoporosis, increase in the rate of healing of a joint injury, and increase or acceleration of local bone growth.

A therapeutically effective dose may prevent or delay the onset of a bone disorder, for example, osteoporosis, which may be desired when early or preliminary signs of the disease are present. Accordingly, any clinical or biochemical assay that monitors any of the foregoing may be used to determine whether a particular treatment is a therapeutically effective dose for treating a bone disorder. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos.

5,399,163; 5,383,851; 5,312,335; 5,064,413; 4,941,880; 4,790,824; or 4,596,556. Examples of well-known implants and modules for use with anti-ALK2 antibodies described herein include: U.S. Pat. No. 4,487,603, which discloses an implantable micro-infusion pump for dispensing medication at a controlled rate; U.S. Pat. No. 4,486,194, which discloses a therapeutic device for administering mendicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Also contemplated is local administration of the anti-ALK2 antibodies described herein where local bone growth is desired (e.g., fracture healing). Local administration of anti-ALK2 antibodies can be achieved using, e.g., medical devices (e.g., prosthetics) and implants. Exemplary local delivery methods are described in, e.g., U.S. Pat. Nos. 5,344,654, 5,324,819; 5,468,845; 6,949,251; and 6,426,332; and U.S. Pat. Appln. Pub. Nos. 2002/0187104, and 2006/0177475.

VIII. Assays

Anti-ALK2 antibodies can be tested for binding to soluble ALK2 (e.g., human ALK2 or portions thereof, e.g., the extra-cellular domain of human ALK2) using standard techniques in the art, for example, ELISA. Binding to ALK2 expressed on cells (e.g., C2C12 cells) can be determined using, e.g., flow cytometry as described in the Examples. Binding of antibodies to ALK2 can also be determined by Western blot. Methods for analyzing binding affinity, cross-reactivity, and binding kinetics of anti-ALK2 antibodies include standard assays known in the art, for example, surface plasmon resonance (SPR) and bio-layer interferometry.

The effects of anti-ALK2 antibodies on bone growth can be tested using cell-based assays, e.g., by measuring the induction of Msx2 or differentiation of osteoprogenitor cells into osteoblasts. For example, osteoprogenitor cells can be contacted (in vitro or in vivo) with the antibodies described herein, followed by measurement of osteogenic activity, e.g., induction of alkaline phosphatase, osteocalcin, and matrix mineralization.

The effects of anti-ALK2 antibodies on cell signaling can be determined using cell-based reporter assays. For example, an assay based on a BMP response element luciferase reporter (BRE reporter assay) can be used to determine the effects of the anti-ALK2 antibodies on BMP (e.g., BMP6, BMP7, BMP9, BMP10) induced reporter activity, wherein a reduction in signal compared to a control (e.g., isotype control antibody) reflects inhibition of the BMP signaling pathway and an increase in signal compared to a control reflects activation of the BMP pathway.

Anti-ALK2 antibodies can be tested for their effects on downstream BMP signaling by SMAD proteins. For example, phosphorylation of SMAD proteins (e.g., SMAD1, 5, and/or 8) in cells treated with the antibodies with or without activation by BMPs can be determined by Western blot using phospho-specific SMAD antibodies. Additionally, ALK2 expressing cell lines transfected with a reporter plasmid that encodes an enzyme under the genetic regulation of a BMP-response element may be used to measure downstream BMP signaling. Here Smad proteins that have been phosphorylated by BMP-stimulated ALK2 dimerize and translocate into the nucleus. There they bind to the BMP-response element and activate transcription of the reporter enzyme, for instance, firefly luciferase. Luciferase generates photons which can be measured with a photospectrometer.

Additionally, mouse progenitor C2C12 cells that naturally express ALK2 can be induced to express the enzyme alkaline phosphatase when stimulated with ALK2 ligands such as BMP9. Alkaline phosphatase dephosphorylates the colorless substrate p-nitrophenyl phosphate which then turns yellow ($\lambda$max=405 nm). Thereafter, alkaline phosphatase activity can be measured with a plate reader that measures absorbance at a wavelength of 405 nm.

The effects of anti-ALK2 antibodies on in vivo bone growth can be tested using, e.g., animal models of osteoporosis (e.g., Kubo et al., *Steroid Biochemistry & Molecular Biology* 1999; 68:197-202; Andersson et al., *J Endocrinol* 2001; 170:529-37). For example, as described in the Examples, ovariectomized mice can be administered the anti-ALK2 antibodies described herein and tested for various bone parameters. Bone parameters can be assessed using conventional methods known in the art, such as DEXA. In vivo fracture healing assays can also be used to assess the effects of anti-ALK2 antibodies on bone growth, for example, as described in U.S. Pat. No. 6,521,750.

IX. Uses and Methods

The anti-ALK2 antibodies, antibody compositions, and methods described herein have numerous in vitro and in vivo utilities. For example, anti-ALK2 antibodies described herein can be administered to cells in culture, in vitro or ex vivo, or to human subjects, e.g., in vivo, to promote bone growth (e.g., bone formation) and/or increase and improve parameters related to bone function (e.g., bone strength, bone density, bone mineralization, cortical bone thickness). The anti-ALK2 antibodies are useful in particular for treating subjects (e.g., human patients) who suffer from or are at risk of disorders that involve bone damage, e.g., bone loss, bone breakage, and bone demineralization.

For example, in some embodiments, provided herein is a method of promoting bone growth or formation comprising administering to a subject an effective amount (e.g., a therapeutically effective amount) of an anti-ALK2 antibody described herein (or a bispecific antibody, immunoconjugate, or composition comprising the antibody).

The anti-ALK2 antibodies described herein are also useful for increasing, improving, and/or promoting various bone-related parameters, e.g., bone strength, bone density, bone mineralization, and cortical bone thickness, and reducing, inhibiting, and/or preventing aspects related to bone loss, for example, bone demineralization.

Accordingly, in some embodiments, provided herein is a method of increasing bone strength in a subject comprising administering to the subject an effective amount (e.g., a therapeutically effective amount) of an anti-ALK2 antibody described herein.

In some embodiments, provided herein is a method of increasing bone density in a subject comprising administering to the subject an effective amount (e.g., a therapeutically effective amount) of an anti-ALK2 antibody described herein.

In some embodiments, provided herein is a method of promoting bone (e.g., skeletal bone) mineralization in a subject comprising administering to the subject an effective amount (e.g., a therapeutically effective amount) of an anti-ALK2 antibody described herein.

In some embodiments, provided herein is a method of increasing cortical bone thickness in a subject comprising administering to the subject an effective amount (e.g., a therapeutically effective amount) of an anti-ALK2 antibody described herein.

In some embodiments, provided herein is a method of treating a bone disorder characterized by bone loss (e.g., loss of bone density) comprising administering to a subject in need thereof an effective amount (e.g., a therapeutically effective amount) of an anti-ALK2 antibody described herein.

In some embodiments, provided herein is a method of promoting bone formation in a subject with a bone disorder characterized by bone loss (e.g., loss of bone density) or bone damage comprising administering to a subject in need thereof an effective amount (e.g., a therapeutically effective amount) of an anti-ALK2 antibody described herein.

The anti-ALK2 antibodies described herein are also useful for treating injuries, for example, bone fractures. Accordingly, in some embodiments, provided herein is a method of treating a bone injury (e.g., bone fracture) comprising administering to a subject in need thereof an effective amount (e.g., a therapeutically effective amount) of an anti-ALK2 antibody described herein. In certain embodiments, the anti-ALK2 antibody is administered locally, e.g., at or proximal to the site of bone injury. In some embodiments, the anti-ALK2 antibody promotes bone healing.

Also provided herein are methods of prophylaxis using the anti-ALK2 antibodies described herein. For example, provided herein is a method of reducing, inhibiting, or preventing bone loss comprising administering to a subject in need thereof a therapeutically effective amount of an anti-ALK2 antibody described herein. Also provided herein is a method of reducing, inhibiting, or preventing bone demineralization comprising administering to a subject in need thereof a therapeutically effective amount of an anti-ALK2 antibody described herein. In some embodiments, the subject has a disorder that is associated with bone loss, such as osteoporosis or cancer.

The anti-ALK2 antibodies described herein are useful for the treatment of various indications associated with bone damage, for example, low bone density, decreased bone strength, bone demineralization. Exemplary indications that involve bone damage for which the anti-ALK2 antibodies described herein are useful include, for example, bone loss (e.g., bone loss associated with cancer), osteoporosis (primary and secondary osteoporosis), bone fracture, osteogenesis imperfecta, hyperparathyroidism, chronic kidney disease mineral bone disorder, sex hormone deprivation or ablation (e.g. androgen and/or estrogen), glucocorticoid treatment, rheumatoid arthritis, severe burns, hyperparathyroidism, hypercalcemia, hypocalcemia, hypophosphatemia, osteomalacia (including tumor-induced osteomalacia), hyperphosphatemia, vitamin D deficiency, hyperparathyroidism (including familial hyperparathyroidism) and pseudohypoparathyroidism, tumor metastases to bone, bone loss as a consequence of a tumor or chemotherapy, tumors of the bone and bone marrow (e.g., multiple myeloma), ischemic bone disorders, periodontal disease and oral bone loss, Cushing's disease, Paget's disease, thyrotoxicosis, renal tubular acidosis, or anorexia nervosa. The anti-ALK2 antibodies described herein are also useful for the treatment of conditions characterized by a failure of bone formation and/or healing, such as non-union fractures, slow-healing fractures, and osteonecrosis (including osteonecrosis of the jaw).

The anti-ALK2 antibodies described herein are also useful for treating subjects who take medication that cause bone loss (e.g., corticosteroids, anti-seizure medications, barbiturates, high-dose thyroid replacement drugs), subjects who have type 1 diabetes, liver disease, kidney disease, or a family history of osteoporosis, subjects with high bone turnover, subjects with thyroid conditions (e.g., hyperthyroidism), and post-menopausal women who are not taking estrogen or other hormone replacement therapy.

Evidence of bone loss can be determined by, e.g., dual energy x-ray absorptiometry (DEXA) scans (to assess changes in bone density), CAT scans (to assess bone growth and fracture healing), and serum markers (e.g., B SAP, osteocalcin, procollagen peptides, BMP7, ICTP, NTx, pyridinoline, deoxypyridinoline).

Accordingly, in one embodiment, provided herein is a method of treating a subject with bone damage (e.g., bone loss) comprising (a) determining whether the subject has evidence of bone loss (e.g., by DEXA, CAT scan, or serum markers), and (b) administering an anti-ALK2 antibody described herein in an effective amount if there is evidence of bone loss.

The anti-ALK2 antibodies described herein may also be used in combination therapies. For example, in some embodiments, the anti-ALK2 antibodies described herein are administered in combination with one or more agents that stimulates bone growth, e.g., growth factors include IGF-1, PDGF, TGF, EGF, BMPs, LIF, and FGFs. Other therapeutic agents that can be administered in combination with the anti-ALK2 antibodies described herein include one or more of vitamin D, calcium, parathyroid hormone (e.g., teriparatide), osteogenin, NaF, osteoprotegerin, and statins.

In certain embodiments, the anti-ALK2 antibodies described herein are administered in combination with anti-resorptive agents, such as bisphosphonates (alendronate, ibandronate, risedronate), calcitonin, estrogens, and raloxifene.

In some embodiments, the anti-ALK2 antibodies described herein are administered to cancer patients who have or are at risk of bone loss. Accordingly, in some embodiments, the anti-ALK2 antibodies described herein are administered to patients with cancer in combination with one or more agents that are useful for treating the cancer (e.g., anti-cancer agents, radiation, surgery).

In some embodiments, the anti-ALK2 antibodies described herein do not cause significant adverse effects. For example, while increasing cortical density, the anti-ALK2 antibodies do not adversely disrupt bone morphology or growth.

In some embodiments of the methods described above, the methods comprise an additional step of determining that the anti-ALK2 antibody exhibits one or more (e.g., 2, 3, 4, 5, or 6) of the following properties:
  a) binds to both mouse and human ALK2;
  b) binds to ALK2 expressed on at least one of osteoblasts, osteoclasts, and/or progenitor cells (i.e., fibro-adipogenic progenitors (FAP));
  c) stimulates bone mineralization;
  d) increases bone mineral density;
  e) inhibits stimulation of ALK2 by BMP ligands; and
  f) inhibits downstream ALK2-mediated BMP signaling by SMAD proteins.

Also encompassed are methods for detecting the presence of ALK2 (e.g., human ALK2) in a sample, or measuring the amount of ALK2, comprising contacting the sample, and a control sample, with a monoclonal antibody, e.g., a human monoclonal antibody, or an antigen binding portion thereof, which specifically binds to ALK2, under conditions that allow for formation of a complex between the antibody or portion thereof and ALK2. The formation of a complex is then detected, wherein a difference complex formation between the sample compared to the control sample is indicative the presence of ALK2 in the sample. Moreover, the anti-ALK2 antibodies described herein can be used to purify ALK2 (e.g., human ALK2) via immunoaffinity purification.

X. Kits

Provided herein are kits comprising the anti-ALK2 antibodies, multispecific molecules, or immunoconjugates described herein, optionally contained in a single vial or container, and include instructions for use. The kits may include a label indicating the intended use of the contents of the kit. The term label includes any writing, marketing materials or recorded material supplied on or with the kit, or which otherwise accompanies the kit. Such kits may comprise the antibody, multispecific molecule, or immunoconjugate in unit dosage form, such as in a single dose vial or a single dose pre-loaded syringe.

The present invention is further illustrated by the following examples which should not be construed as further limiting. The contents of Sequence Listing, figures and all references, patents, and published patent applications cited throughout this application are expressly incorporated herein by reference.

EXAMPLES

Commercially available reagents referred to in the Examples below were used according to manufacturer's instructions unless otherwise indicated. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

Example 1: Generation of Immune-Biased Phage Display Libraries

Anti-ALK2 antibodies were obtained from immune-biased phage display libraries of Fab fragments derived from mice immunized with plasmids encoding ALK2 (from the ACVR1 gene) and/or recombinant ALK2 protein.

Biolistic Bullet Preparation

Seven plasmids and two controls (Table 1) were used to immunize 36 CD-1 and 36 NZBWF/J mice. Table 1 summarizes the plasmids used for gene gun bullet preparation. Amino acid sequences encoded by the plasmids are provided in Table 6. Eighteen mice of each strain were immunized (subcutaneously) with DNA suspended in sterile TE buffer supplemented with aSMART™ DNA Immunization Adjuvant Reagent (Antibody Research) or the HELIOS® gene gun according to manufacturer's instructions (Bio-Rad, HELIOS® Gene Gun). Approximately 46 µg DNA was precipitated onto 16.6 µg gold beads which were suspended in polyvinylpyrrolidone (PVP). Prepared cartridges containing DNA/gold particles were stored at 4° C. until use.

TABLE 1

ALK2 antigens and DNA constructs used to immunize mice

| SEQ ID | Plasmid | Description |
|---|---|---|
| 98 | pDMC074 | Human ALK2 extracellular domain (ECD) (Uniprot Accession # Q04771) without signal peptide in vaccine vector (pVAX1, Invitrogen) |
| 99 | pDMC094 | Human ALK2 signal peptide and ECD in vector pVAX1 |
| 100 | pDMC075 | Human ALK2 signal peptide and ECD in vaccine vector pVAX1. Six codons within the human ALK2 ECD are different from ones used in the pDMC094 construct |
| 101 | pDMC076 | Human ALK2 ECD without signal peptide in vector pVAX1 |
| 102 | pDMC099 | Human ALK2 signal peptide, N-terminal glutathione S-transferase (GST)-human ALK2 ECD fusion protein in vector pVAX1 |
| 103 | pDMC100 | N-terminal GST-human ALK2 ECD fusion protein without signal peptide in vector pVAX1 |
| 104 | pDMC068 | Human ALK2 signal peptide, ECD and transmembrane domain in vector pVAX1 |
| — | pVAX1 control | Empty expression vector without gene insert |

Phage Library Construction

Two different phage libraries were constructed from the immunized animals as follows. Immune biased Fab display libraries were produced from RNA isolated from spleens of NZBWF1/J and CD-1 female mice exposed to the ALK2 ECD by either protein or DNA immunization. Standard panning techniques were used to isolate a series of murine antibodies reactive to the ALK2 ECD. Variable regions of heavy and light chains were transferred into eukaryotic expression vectors bearing the murine IgG1 FC and kappa constant regions, respectively, and signal peptides to generate full length heavy and light chains. Antibodies were produced by transient transfection of HEK 293 cells and purified using protein A chromatography. The intact molecular weight of each antibody was found to conform to the theoretical molecular weight predicted by the amino acid sequence and expected glycosylation by electrospray ionization time of flight (ESI-TOF) mass spectrometry.

A first phage library (pZIP00000) of gene gun and DNA immunized early sacrifice/low titer mouse spleens and lymph nodes was generated by pooling lymph nodes and spleens from the eight mice (sacrificed after 25 days) giving the highest sera titer. Mice were sacrificed, and spleens and lymph nodes were harvested, homogenized, and stored in RNA stabilizing buffer (TRI REAGENT®, Sigma-Aldrich) at −80° C. until library construction. For library construction, total RNA was purified using 0.5 mL isopropanol to 1 mL buffer TRI REAGENT® precipitation, washed with 75% ethanol, and re-suspended in 250 μL DEPC-treated (RNAse-inhibiting) water (Ambion). First strand cDNA was amplified from total RNA using commercial kits (Superscript III First-Strand Synthesis System for RT-PCR, Life Technologies) following the manufacturer's protocol. Second strand cDNA synthesis to generate pools of IgG1, IgG2a, and Ig Kappa germline sequences was performed. Ig Kappa sequences were digested with restriction enzymes and cloned into a gpIII fusion phagemid, followed by the restriction digest and cloning of the IgG1 and IgG2a heavy chain pools using standard cloning procedures.

A second phage library (pZAP0000) of gene gun and DNA immunized late sacrifice/high titer mouse spleens and lymph nodes, immunized with Gene Gun gold coupled plasmids, was generated by pooling lymph nodes and spleens from eight mice (sacrificed after 53 days) giving the highest sera titer binding results. Mice were sacrificed, and spleens and lymph nodes were harvested, homogenized, and stored in buffer (TRI REAGENT®, Sigma-Aldrich) at −80° C. until library construction. The library was constructed using the same method as pZIP0000 described above.

Sera Titer Analysis

Sera titer analysis was performed using commercially available ELISA plates (ELISA MaxiSorp™ plates) coated with 1-4 μg/mL of a pool of recombinant human ALK2 proteins in equimolar concentrations (Creative Biomart ALK2, Sino Biological ALK2-Fc Chimera). Sera was harvested from whole blood by centrifugation, serial dilutions from 1:00 to 1:7,812,500 were prepared in PBS, then applied to ALK2 coated plates, washed, and detected by goat anti-mouse IgG labeled with horseradish peroxidase (Life Technologies) using TMB Ultra (Pierce) to develop absorbance. The resulting plates were read at 450 nm.

Example 2: Identification of Anti-ALK2 Antibodies

This Example describes the identification of anti-ALK2 antibodies by phage panning, screening, and sequence analysis.

Identification of Anti ALK2 Antibodies

Anti-ALK2 antibodies were obtained by panning immune-biased phage display libraries pZIP0000 and pZAP0000 with standard methods using DYNABEADS® MyOne™ Streptavidin Ti (Life Technologies) with biotinylated ALK2 ECD (Creative Biomart catalog number ACVR1-01H). Phage plasmids were used as templates for PCR to clone the variable heavy and light chain domains into a monoclonal Ab (mAb) murine IgG1. The resulting anti-ALK2 antibodies were tested for activity in a BRE-luciferase reporter assay, which was developed as described below.

BRE-Luciferase Reporter Assay

A BMP reporter plasmid was constructed by synthesizing the BMP-response element (BRE) described in Yadav et al. (*PloS One* 2012; 7:e37134). NheI and HindIII sites were added to the 5' and 3' termini, respectively, to facilitate cloning into plasmid pGL4.26 luc2/minP/Hygro (Promega E8441) that encodes luciferase downstream of a minimal promoter. The plasmid also encodes the hygromycin resistance marker. The final plasmid was designated pGL4.26 BRE2. This plasmid was verified by DNA sequencing of the BRE region.

Host C2C12 cells (ATCC CRL-1772) were cultured in DMEM with high glucose and L-glutamine (ATCC 30-2002) supplemented with 10% FBS (Tissue Culture Biology 101). Cells were sub-cultured every 3-4 days prior to transfection. C2C12 cells were transfected with plasmid pGL4.26 BRE2 using commercial DNA transfection reagent protocols (LIPOFECTAMINE® 3000, Invitrogen L300015) according to manufacturer's instructions. Transfected cells were cultured in 96 well plates in media containing 200 μg/mL hygromycin. Stable clones were scaled up in selective media and cryopreserved at liquid nitrogen temperatures.

Figure 1:
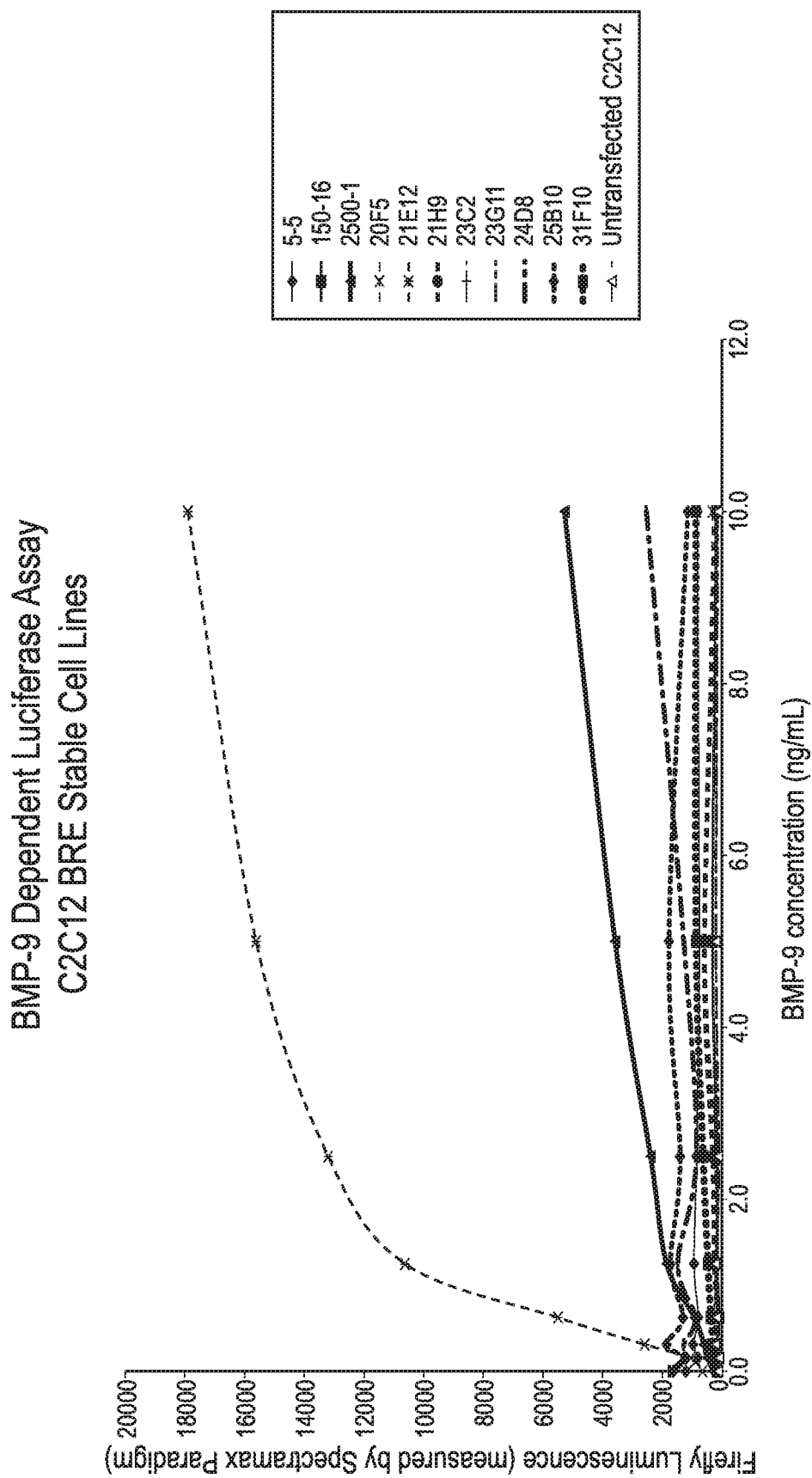
FIG. 1 shows the response of multiple cell lines transfected with reporter C2C12 cells to BMP9 (also designated BMP-9) in the BRE-luciferase cell-based assay.

To evaluate clones for BMP-dependent luciferase expression, clones were stimulated with mouse BMP9 (R&D Systems) in media containing 1% FBS. Expression of luciferase was determined using the Dual-Glo Luciferase Assay System (Promega E2940) and a Spectramax Paradigm plate reader (Molecular Devices). As shown in FIG. 1, clone 21E12 was found to have the highest luciferase signal.

Activity of Anti-ALK2 Antibodies

Figure 2:
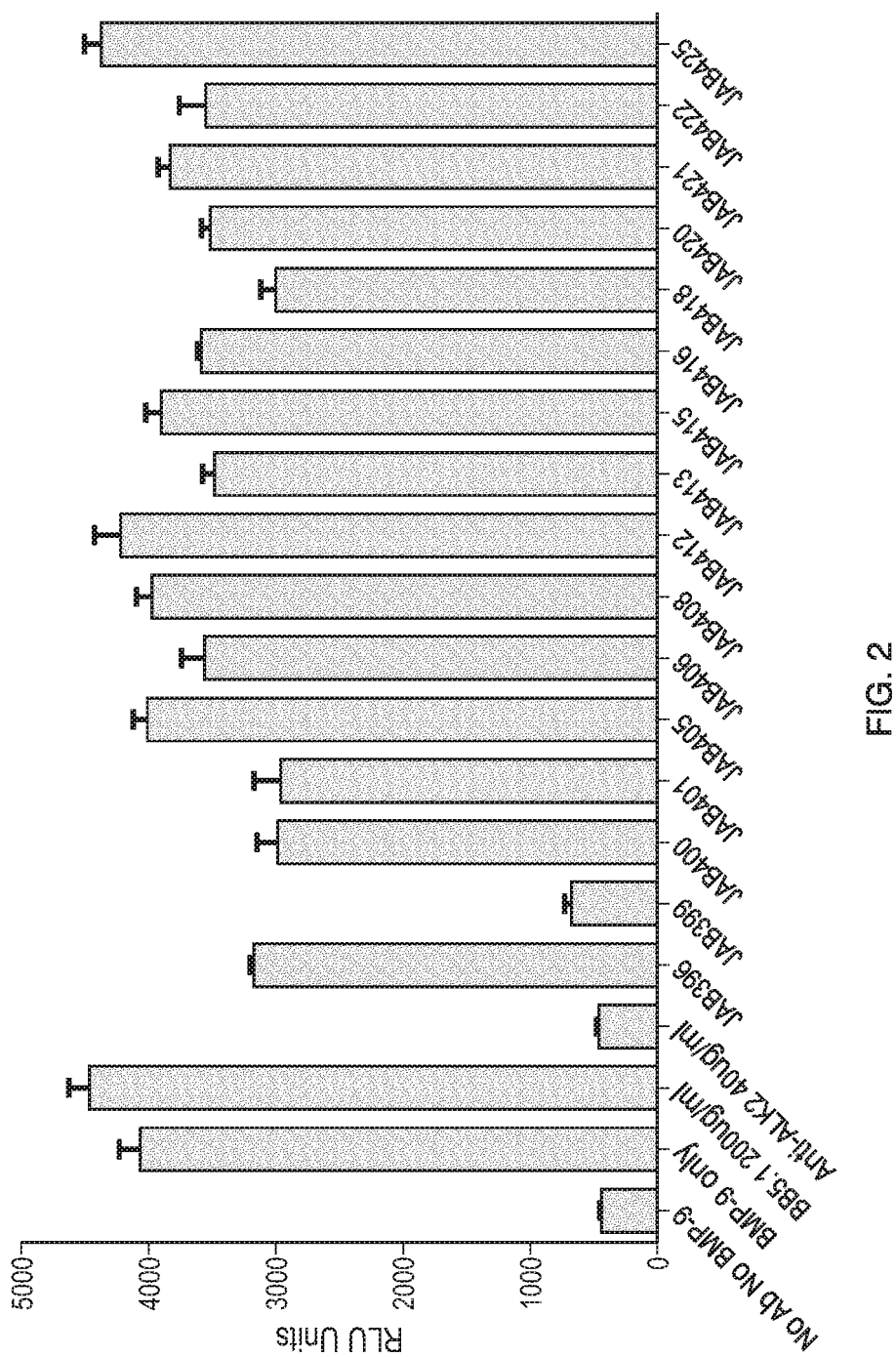
FIG. 2 shows the evaluation of anti-ALK2 mAbs for inhibition of BMP9-dependent signaling in the BRE-luciferase assay. Standard deviation bars for n=3 shown.

The activity of mAbs isolated from phage libraries was ascertained via the BMP response element luciferase reporter assay described above (FIG. 2). Each antibody was tested at a concentration of 1.3 μM for inhibition of BMP9-mediated ALK2 signaling. A polyclonal anti-ALK2 antibody (R&D Systems) was used as a positive control for inhibition.

Figure 3:
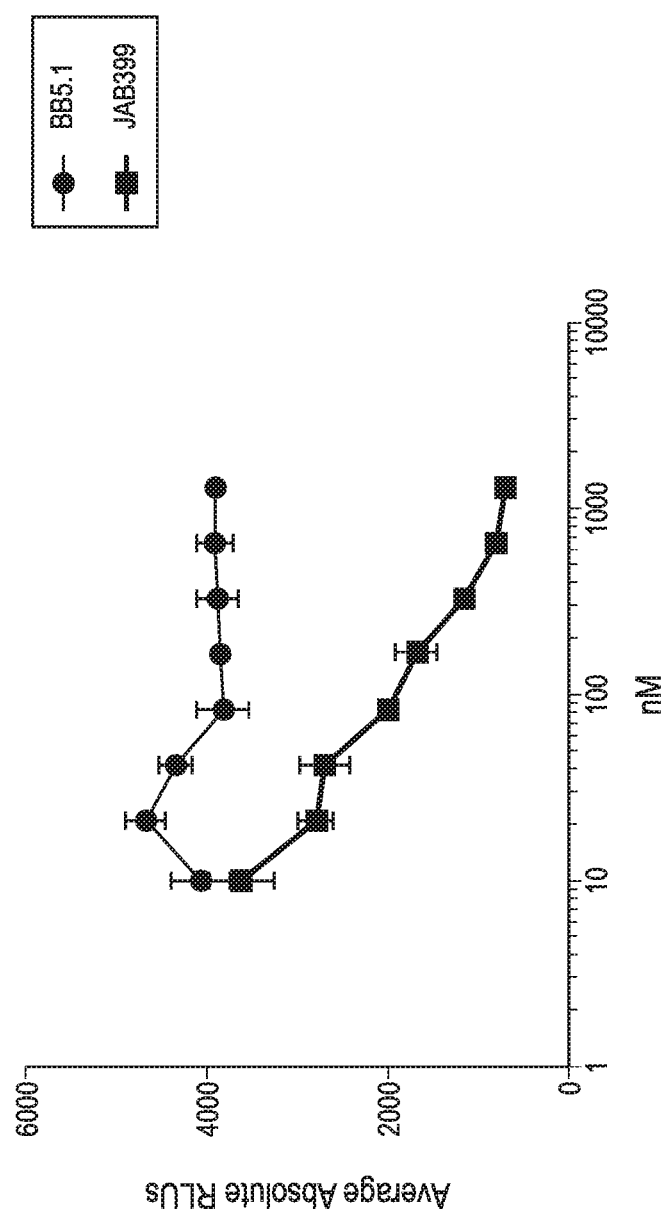
FIG. 3 shows the titration of antibody JAB0399 in the BRE-luciferase functional assay compared to BB5.1 isotype matched control. Standard deviation bars for n=3 shown.

Monoclonal antibody JAB0399, which was isolated from phage library pZIP000 after two rounds of phage panning, was selected for further characterization and optimization. FIG. 3 shows the titration of antibody JAB0399 in the BRE-luciferase assay, with antibody BB5.1 used as an isotype-matched negative control. Approximately 100 other mAbs were shown to be non-functional via the BRE-luciferase assay (data not shown).

Upon sequencing, mAb JAB0399 was found to have a cloning artifact mutation (Ser135Phe) within the CH1 domain of the constant region. This mutation was corrected using standard PCR cloning techniques. The resulting mAb that has the wild-type serine at position 135 was designated JAB0481.

Example 3: Characterization of Anti-ALK2 Antibodies

This Example describes the characterization of various aspects of the anti-ALK2 antibodies JAB0399 and JAB0481.

Molecular Weight Confirmation

Figure 4:
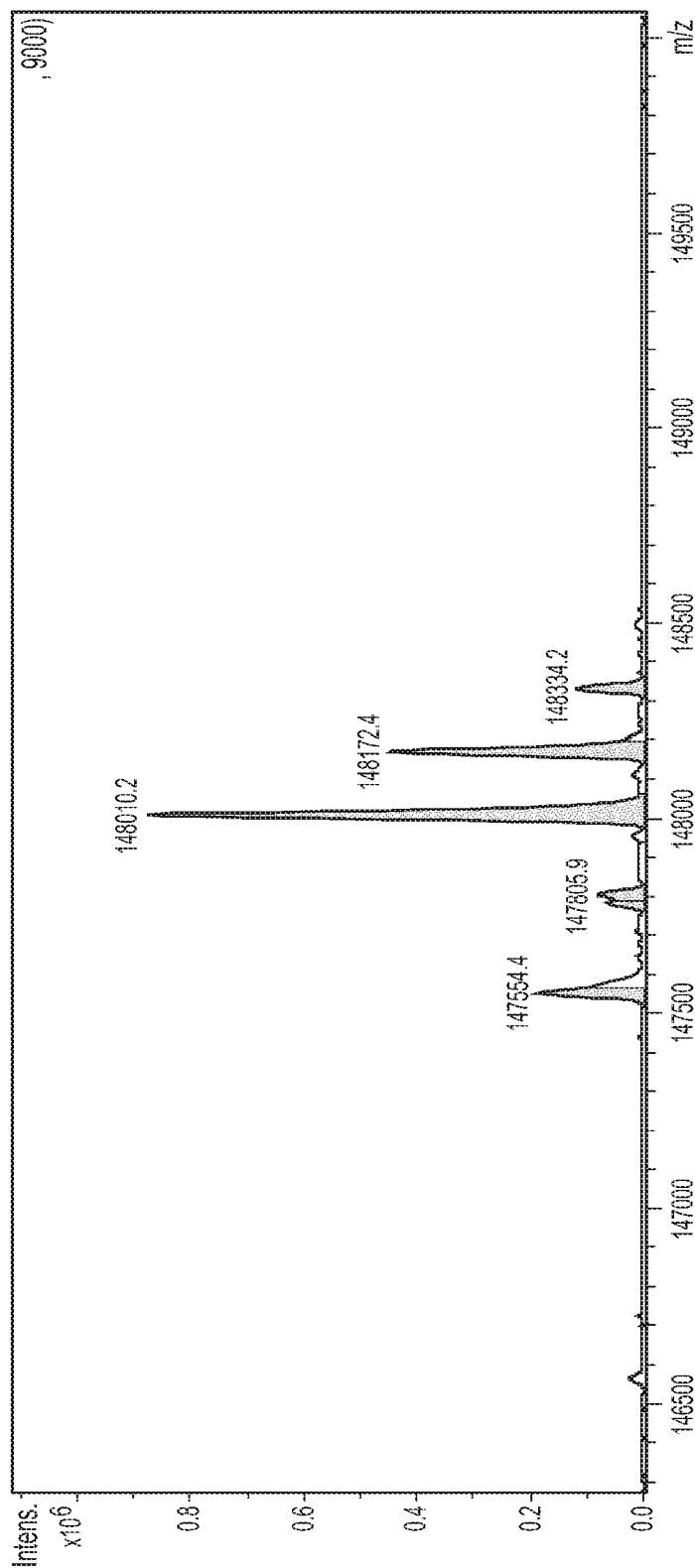
FIG. 4 shows the ESI-ToF Mass Spectrometry of JAB0399 for intact molecular weight determination.
Figure 5:
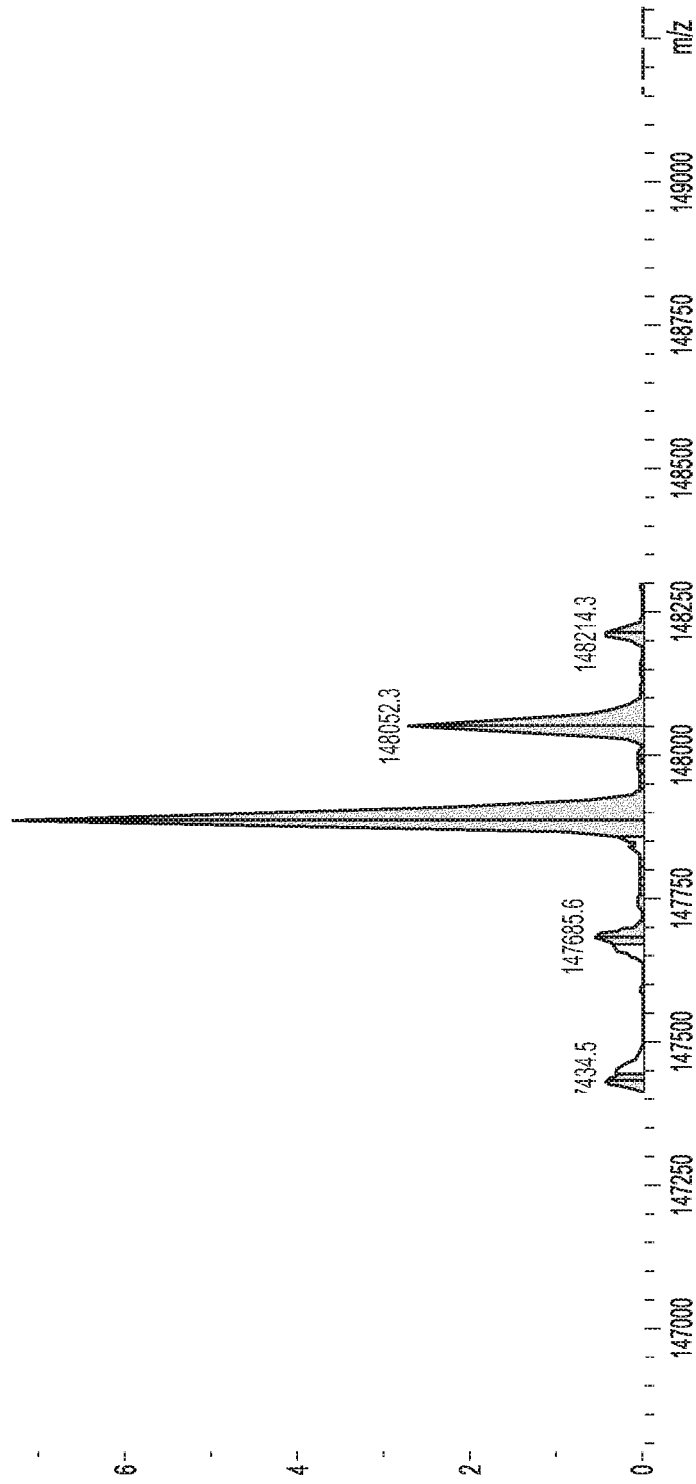
FIG. 5 shows the ESI-ToF Mass Spectrometry of JAB0481 for intact molecular weight determination.

The intact molecular weights of JAB0399 and JAB0481 were found to conform to the theoretical molecular weight predicted by their respective amino acid sequences added to the mass of a complex-type G0F N-linked glycan on each heavy chain by electrospray ionization time of flight (ESI-TOF) mass spectrometry. The experimentally determined molecular weights of JAB0399 and JAB0481 were determined to be 148,010.2 Da (FIG. 4) and 147,889.6 Da (FIG. 5), respectively.

Thermal Stability

Figure 6:
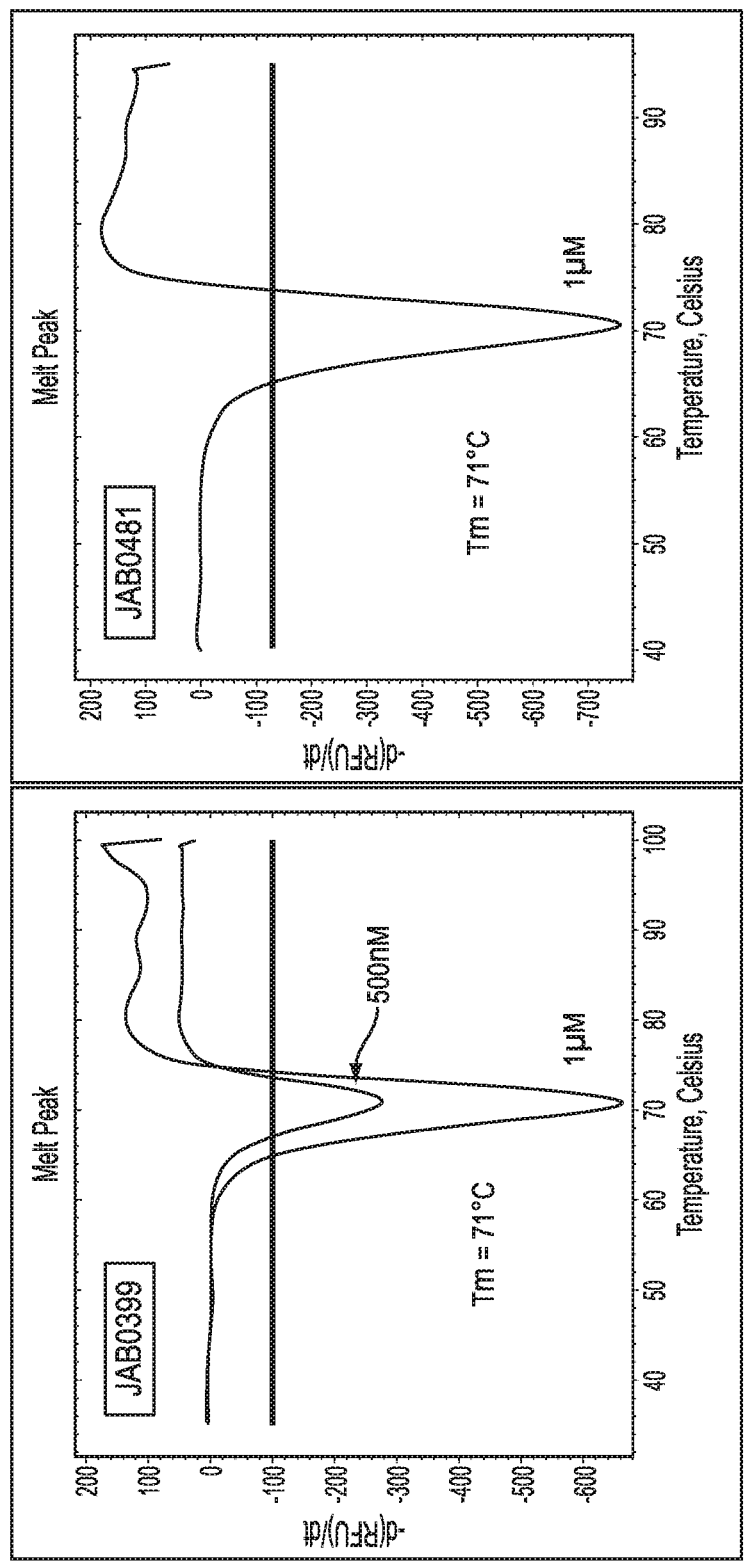
FIG. 6 shows the thermal denaturation midpoint determinations for antibodies JAB0399 and JAB0481.

Differential scanning fluorimetry (DSC) was performed to determine the thermal denaturation midpoint (Tm) temperatures of JAB0399 and JAB0481. DSC was performed on a C1000 thermal cycler (Bio-Rad) with SYPRO® Orange fluorescent dye, temperature increase from 40 to 95° C. with 0.1° C./s intervals using the melt curve method, and collection of all channels. As shown in FIG. 6, both JAB0399 and JAB0481 have a Tm of 71° C.

Example 4: Binding Affinity of Anti-ALK2 Antibodies to Human ALK2

This Example describes the binding affinity of anti-ALK2 antibodies to human ALK2 using bio-layer interferometry (Octet) and surface plasmon resonance (SPR/Biacore).

Octet Binding Analysis

The binding of anti-ALK2 antibodies to human ALK2 ECD and absence of binding to human ALK1 ECD was verified by bio-layer interferometry using an Octet HTX instrument (ForteBio).

ALK2-Fc (R&D Systems), ALK2-Fc (Sino Biological catalog number 10227-H03H), and ALK1-Fc (R&D Systems catalog number 370-AL-100) were diluted to 10 µg/mL in 1× kinetics buffer (ForteBio) and loaded onto anti-human Fc tips (ForteBio). After baseline equilibration in kinetics buffer (ForteBio), the sensors were applied to solutions of antibodies JAB0399, JAB0481, and BB5.1 (isotype control mAb) diluted to 10 µg/ml in kinetics buffer. The sensors were then applied to antibody-free kinetics buffer to measure antibody dissociation.

Figure 7:
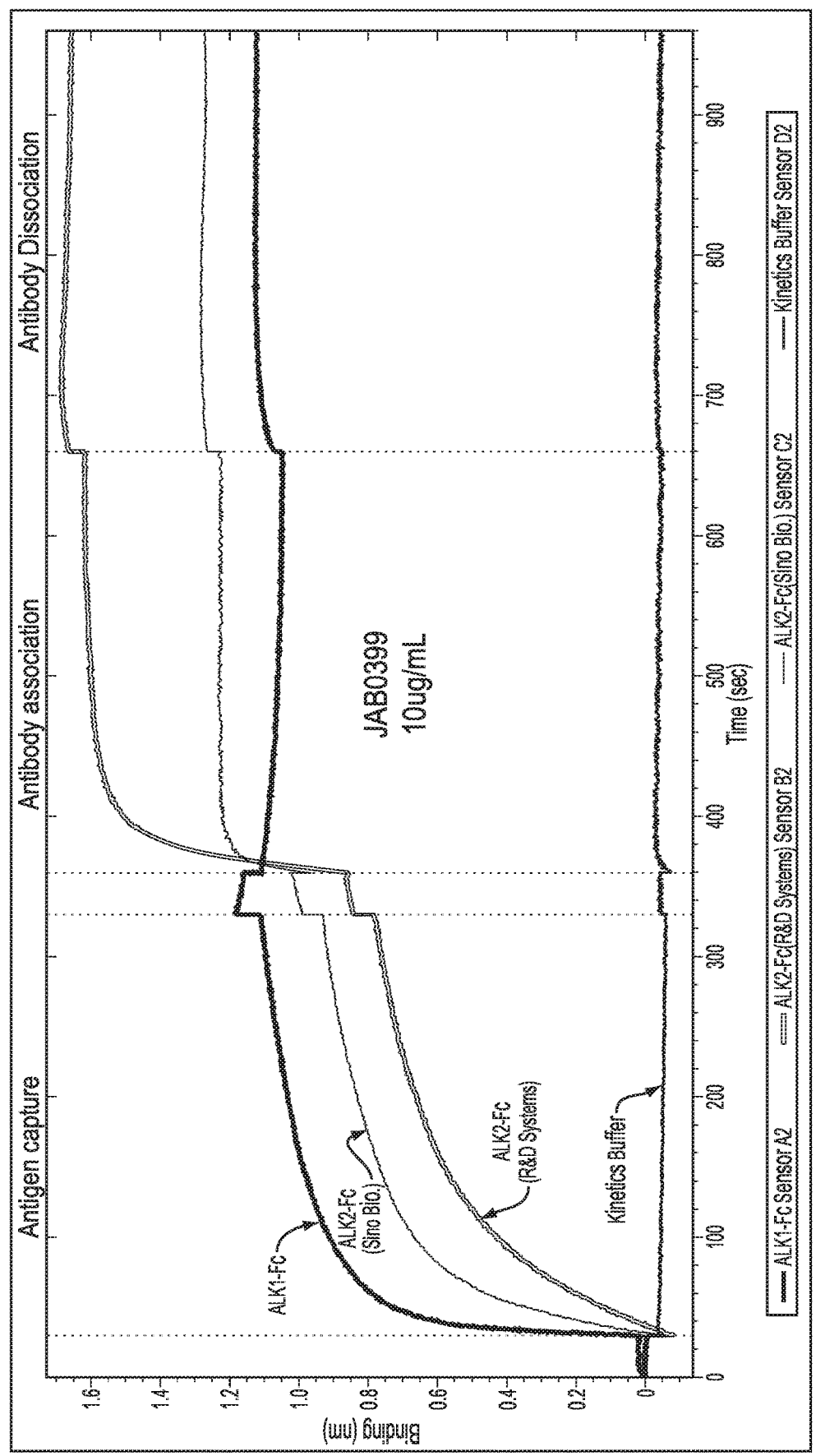
FIG. 7 shows binding of antibody JAB0399 to recombinant ALK2-Fc and recombinant ALK1-Fc by bio-layer interferometry.
Figure 8:
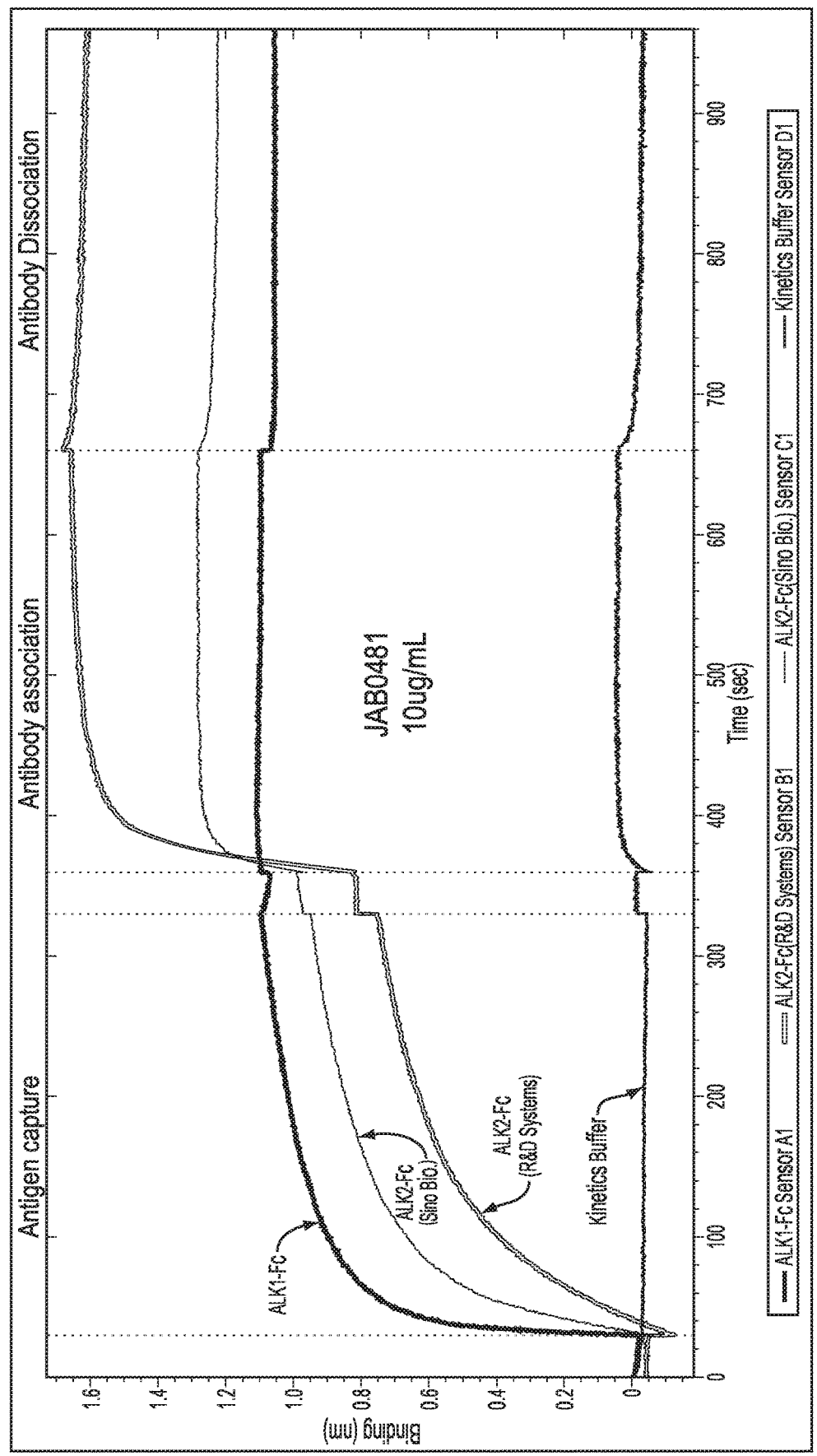
FIG. 8 shows binding of JAB0481 to recombinant ALK2-Fc and recombinant ALK1-Fc by bio-layer interferometry.

A summary of the parameters used to assess binding is provided below:
1. Baseline: 1×KB, 30 seconds
2. Loading: Antigens in 1×KB, 300 seconds
3. Baseline: 1×KB, 30 seconds
4. Association: mAb in 1×KB, 300 seconds
5. Dissociation: 1×KB, 300 seconds As shown in FIG. 7 and FIG. 8, JAB0399 and JAB0481 show specificity of binding. Both mAbs bound to the ALK2 ECD Fc fusions obtained from two different commercial sources, but did not bind to the paralog ALK1. Non-specific binding to the sensor was not observed.

Biacore Analysis

The binding kinetics and affinity dissociation constant for antibody JAB0481 binding the extracellular domain of ALK2 (amino acids 1-123 of the mature ALK2 protein; Creative Biomart catalog number ACVR1-01H) was determined by surface plasmon resonance using a Biacore instrument (GE Lifesciences).

Anti-mouse IgG was immobilized on carboxymethylated dextran BiaCore sensor chips (CMS, GE Biosciences) using a Mouse Antibody Capture Kit (GE Lifesciences product number BR100838). Two sensors were prepared; one for a "low" density of JAB0481 captured on the sensor and one with a "high" density of JAB0481 captured on the sensor. JAB0481 was diluted to 0.05 mg/ml in HEPES EDTA surfactant buffer (HBS-EP), pH 7.4 and injected onto the mouse antibody capture sensors. The volume of JAB0481 solution injected for the "low" density condition was 104, and the volume that was used for the "high" density condition was 30 µL.

The ALK2 ECD was diluted in HBS-EP buffer and injected over the JAB0481 captured sensors at concentrations ranging from 2000 nM to 250 nM followed by a 300 second association period. This was followed by the injection of HBS-EP buffer and a 500 second dissociation period. Relative response deflection was plotted against time and the data were fitted to curves according to the Langmuir 1:1 binding kinetic model.

Figure 9:
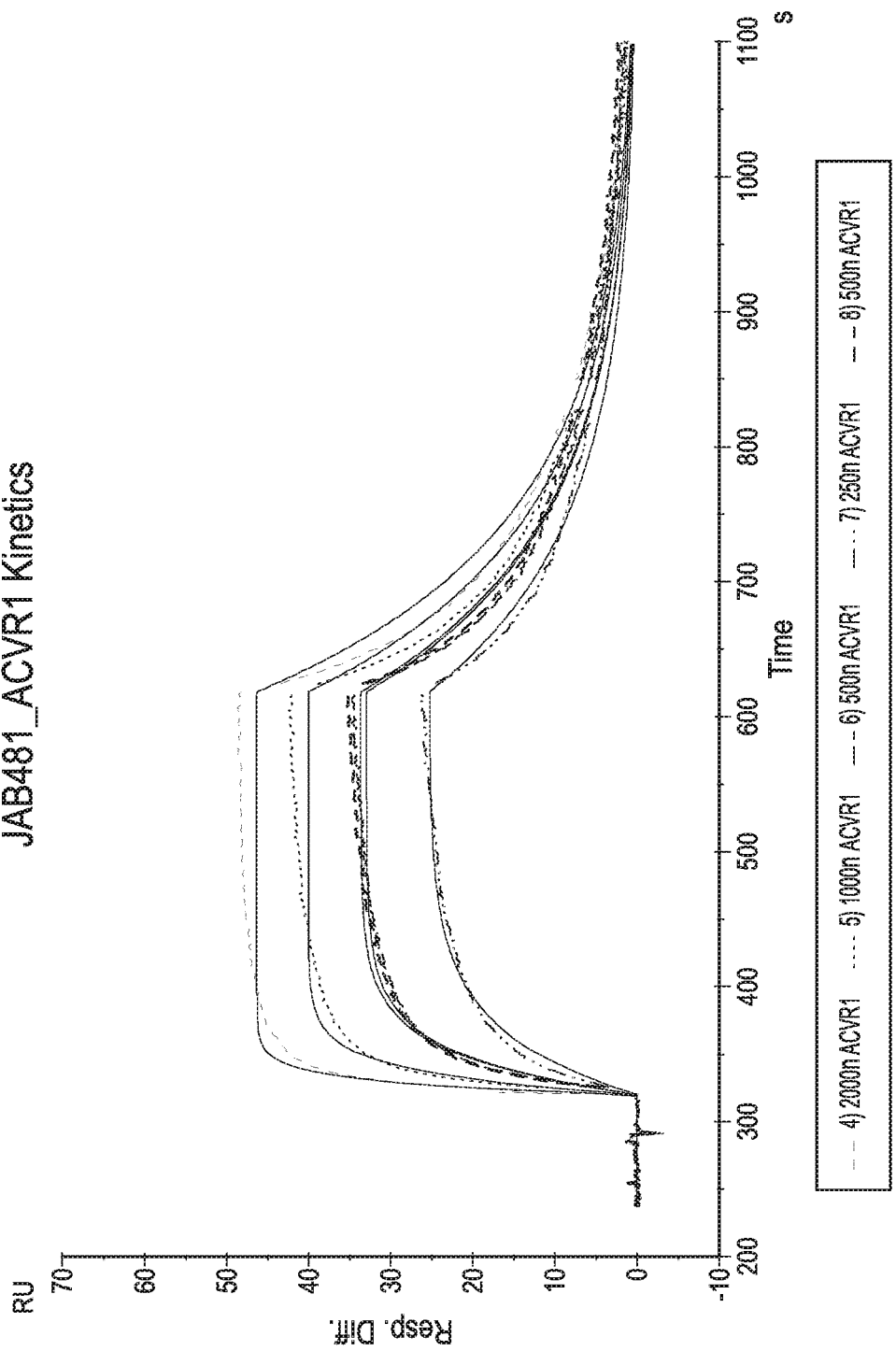
FIG. 9 shows binding of JAB0481 to the ALK2 ECD (ACVR1) by surface plasmon resonance (SPR, or Biacore) as a function of time; low density JAB0481 capture surface. Values given are in nM.
Figure 10:
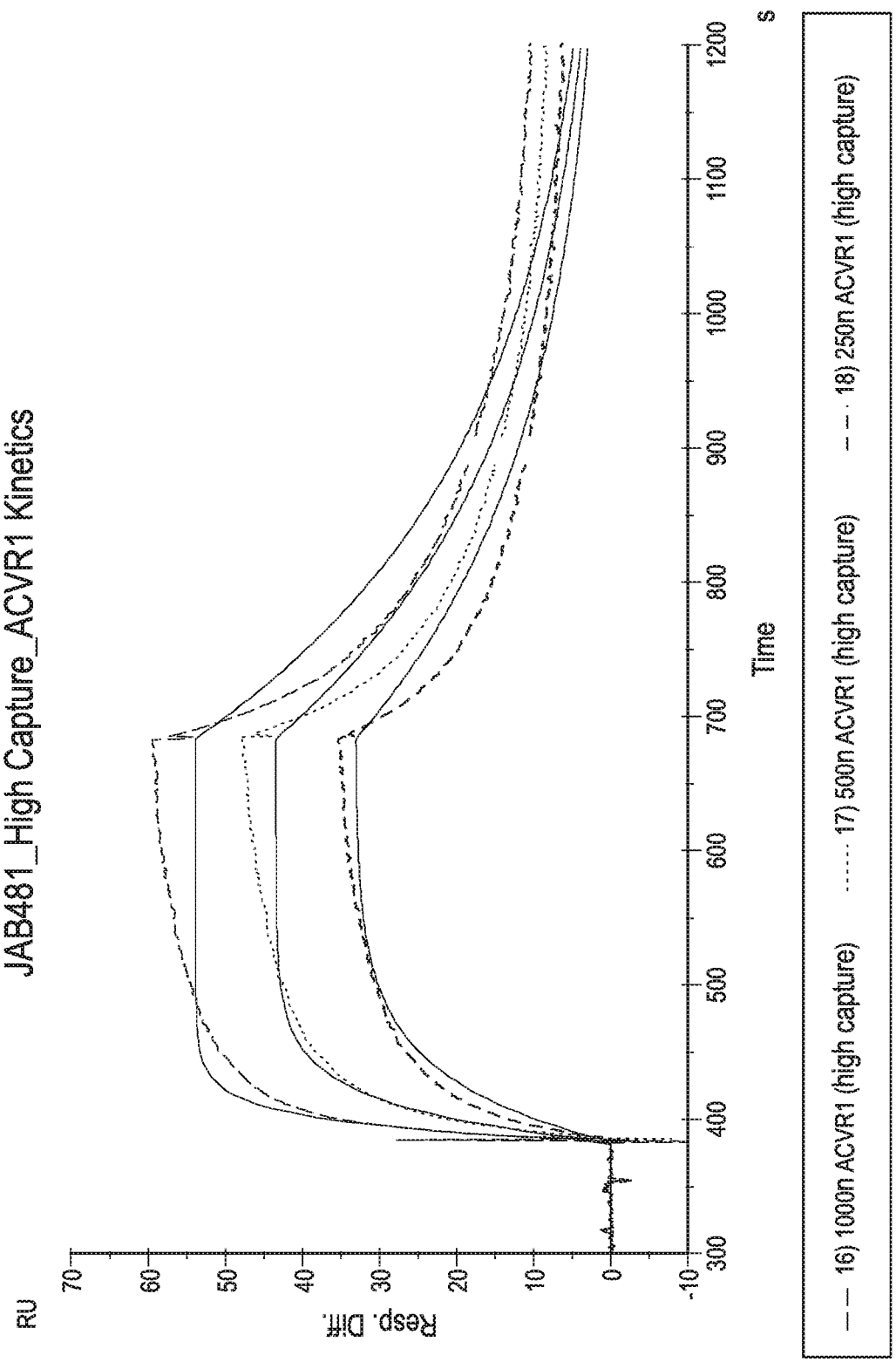
FIG. 10 shows binding of JAB0481 to the ALK2 ECD by surface plasmon resonance as a function of time; high density JAB0481 capture surface. Values given are in nM.

The sensorgrams for the binding of the ALK2 ECD to JAB0481 at low surface density is provided in FIG. 9, while the sensorgrams for the binding of the ALK2 ECD to JAB0481 at high surface density is provided in FIG. 10. Table 2 provides the association and dissociation rates, the dissociation constant, and Chi squared values calculated from the Biacore binding data. The dissociation constant ($K_D$) determined for binding of JAB0481 to recombinant human ALK2 ECD was determined to be 155 nM when measured with the low density JAB0481 sensor and to be 72.7 nM when measured with the high density JAB0481 sensor.

TABLE 2

SPR binding of antibody JAB0481 to recombinant ALK2 ECD

| mAb | Surface Density | Antigen | $k_a$ (1/Ms) | $k_d$ (1/s) | $K_D$ (M) | Chi² |
|---|---|---|---|---|---|---|
| JAB0481 | Low | ACVR1 ECD | $5.36 \times 10^4$ | $8.33 \times 10^{-3}$ | $1.55 \times 10^{-7}$ | 1.74 |
| JAB0481 | High | ACVR1 ECD | $6.42 \times 10^4$ | $4.67 \times 10^{-3}$ | $7.27 \times 10^{-8}$ | 10.1 |

Example 5: Binding of Anti-ALK2 Antibodies to ALK2 Expressed on Cells

Anti-ALK2 antibodies were evaluated for binding to ALK2 expressed on the cell surface of mouse myoblast cells (C2C12; ATCC CRL-1772) by flow cytometry. The expression of ALK2 in wild-type C2C12 cells was confirmed by RT-qPCR and by observing the binding of commercially available polyclonal anti-ALK2 antibodies to the cells by flow cytometry (data not shown). To demonstrate specificity, the antibodies were also tested for binding to ALK2 knock-out C2C12 cells in which the ACVR1 alleles were deleted using CRISPR/Cas9 technology (PNA Bio). Loss of ALK2 expression was verified by flow cytometry and genomic sequencing (data not shown).

Wild-type and ALK2 knock-out C2C12 cells were detached from culture flasks using AssayComplete™ Cell Detachment Reagent (DiscoverX) which was used to maintain intact cell membrane morphology. Cells were washed twice with PBS and then re-suspended in PBS. A dilution series of anti-ALK2 antibodies ranging from 5000 ng/mL to 2.45 ng/mL were added to the cells and incubated for 30 minutes at 4° C. Cells were washed once in FACS buffer (5% bovine serum albumin, 5% sodium azide in PBS) re-suspended in blocking buffer (6% BSA in PBS) and incubated on wet ice for 15 minutes. The binding of the anti-ALK2 antibodies to cells was detected with a 1:100 dilution of Alexa Fluor488-conjugated donkey anti-mouse IgG (ThermoFisher catalog number A21202). Cells were then washed twice in FACS buffer, re-suspended in FACS buffer and the binding of anti-ALK2 antibodies determined by flow cytometry using a DxP6 flow cytometer (Cytek).

Figure 11:
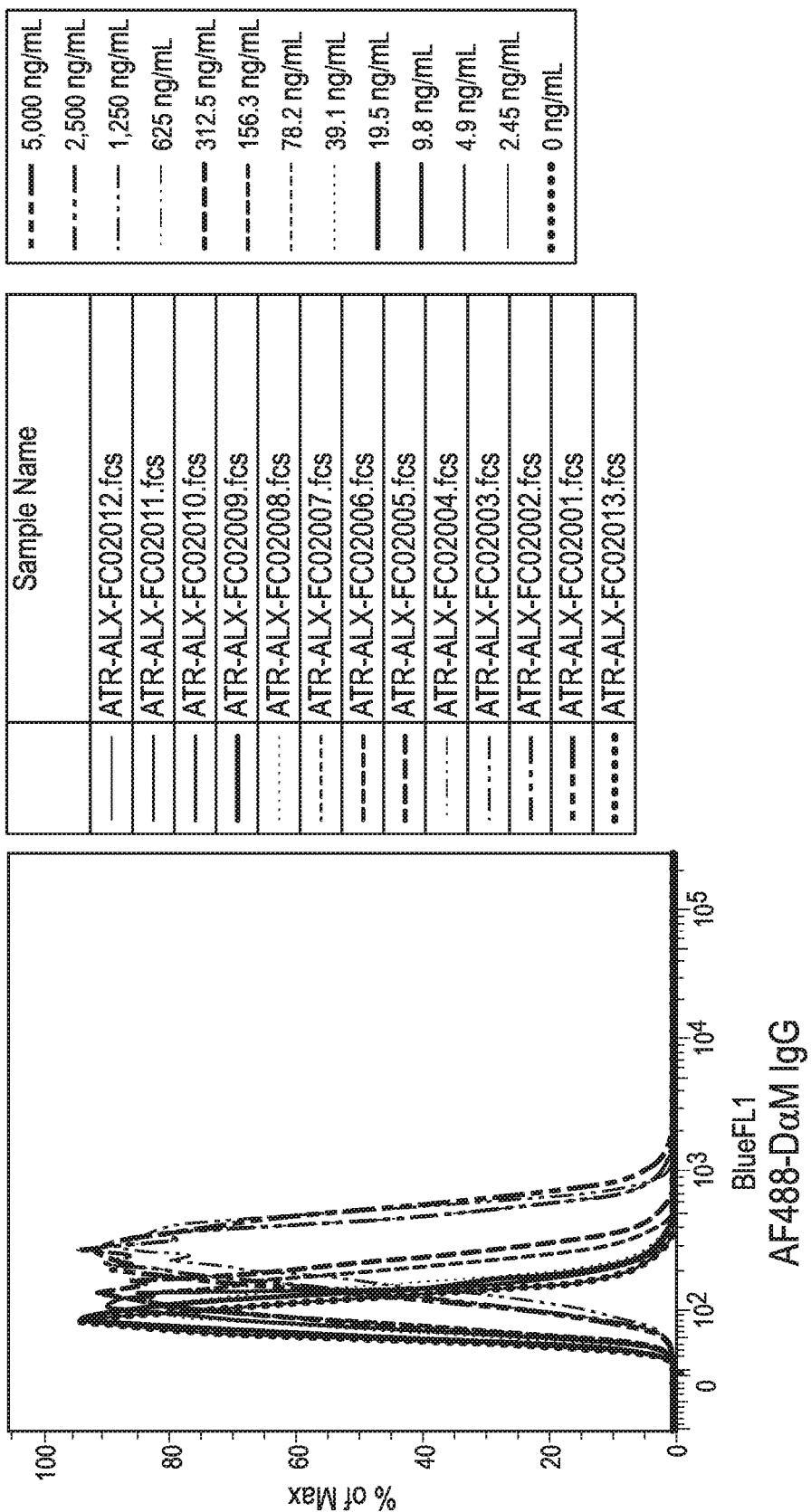
FIG. 11 shows antibody JAB0481 binding to wild-type C2C12 cells by flow cytometry at multiple antibody concentrations.
Figure 12:
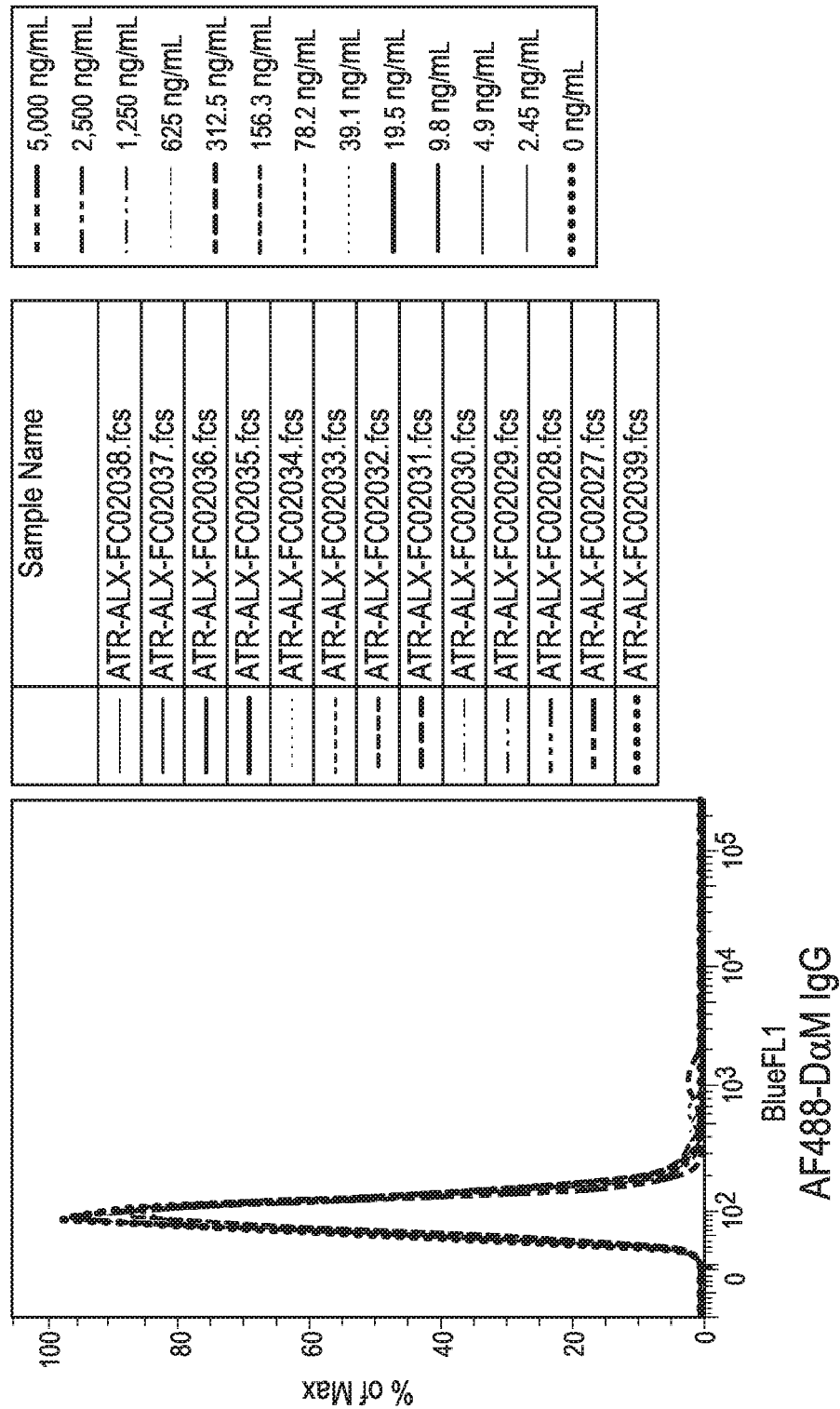
FIG. 12 shows lack of binding of antibody JAB0481 to ALK2 knock-out C2C12 cells by flow cytometry at multiple antibody concentrations.

Antibody JAB0481 binds to wild-type C2C12 cells in a concentration dependent manner (FIG. 11), but does not bind to ALK2 knock-out C2C12 cells (FIG. 12).

Example 6: Affinity Maturation of Anti-ALK2 Antibodies

In vitro affinity maturation of anti-ALK2 antibodies was performed to improve their binding to ALK2, and thus their ultimate potency for administration.

Affinity maturation was performed by mutating the complementary determining regions (CDRs) of JAB0481 by saturation mutagenesis of each position of heavy chain CDRs 2 and 3 and light chain CDR3 independently using primers that randomly encode NNK at each codon where N=A/C/G/T and K=G/T. Mutated antibody sequences were pooled and cloned into a phagemid vector to generate an affinity maturation library. This phage library was panned for ALK2 binders for four rounds under binding conditions with increasing stringency at each round. Phage binders were sequenced and convergent antibody sequences were cloned and expressed as murine IgG1 mAbs. Antibodies were expressed and screened for binding to ALK2 by BIAcore and evaluated for inhibition of BMP9-mediated ALK2 signaling using the BMP Response Element (BRE) luciferase reporter assay.

Figure 13:
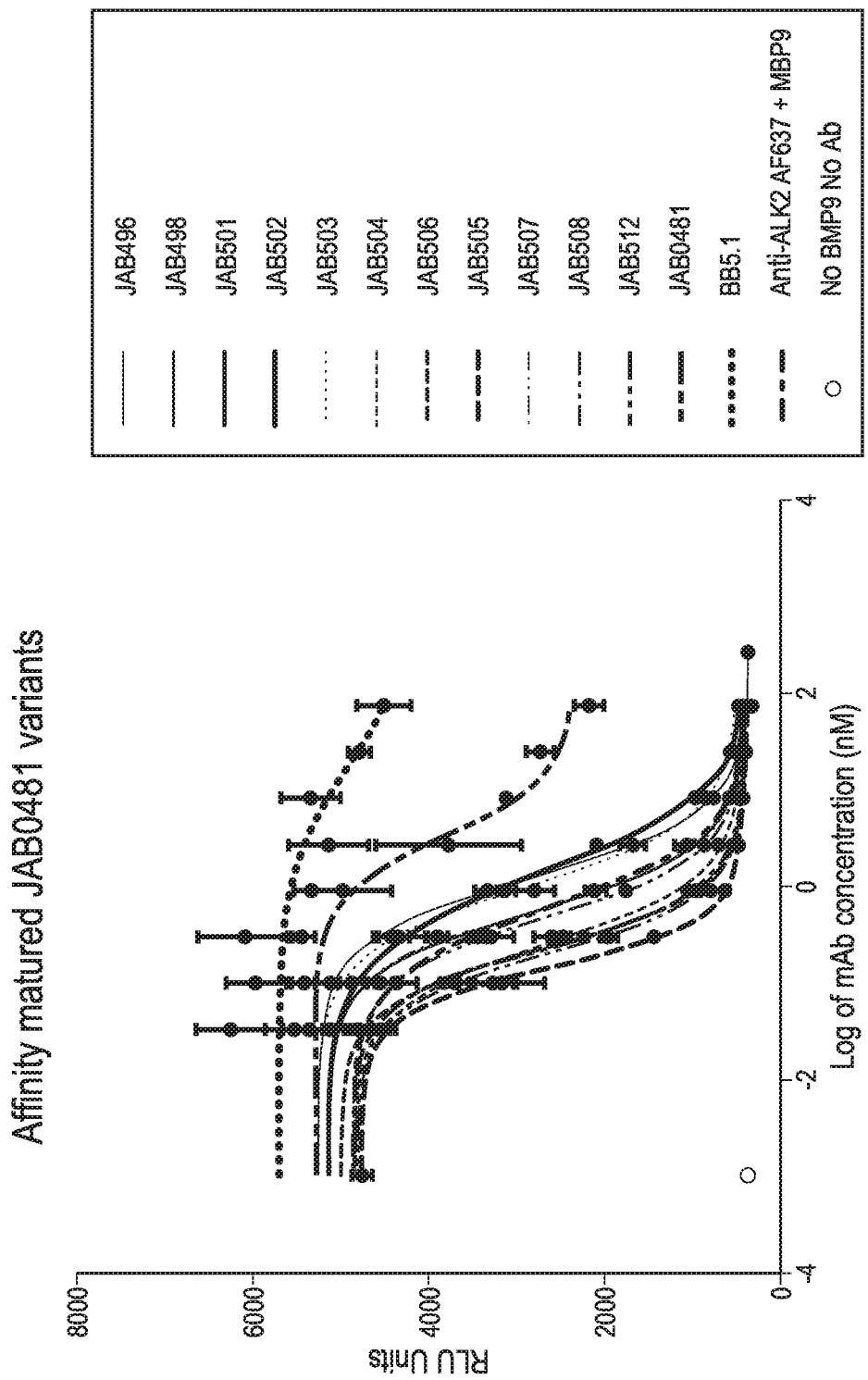
FIG. 13 shows inhibition of BMP9-mediated ALK2 signaling in C2C12 cells by affinity matured anti-ALK2 antibody variants derived from JAB0481. Standard deviation bars for n=3 shown.
Figure 14:
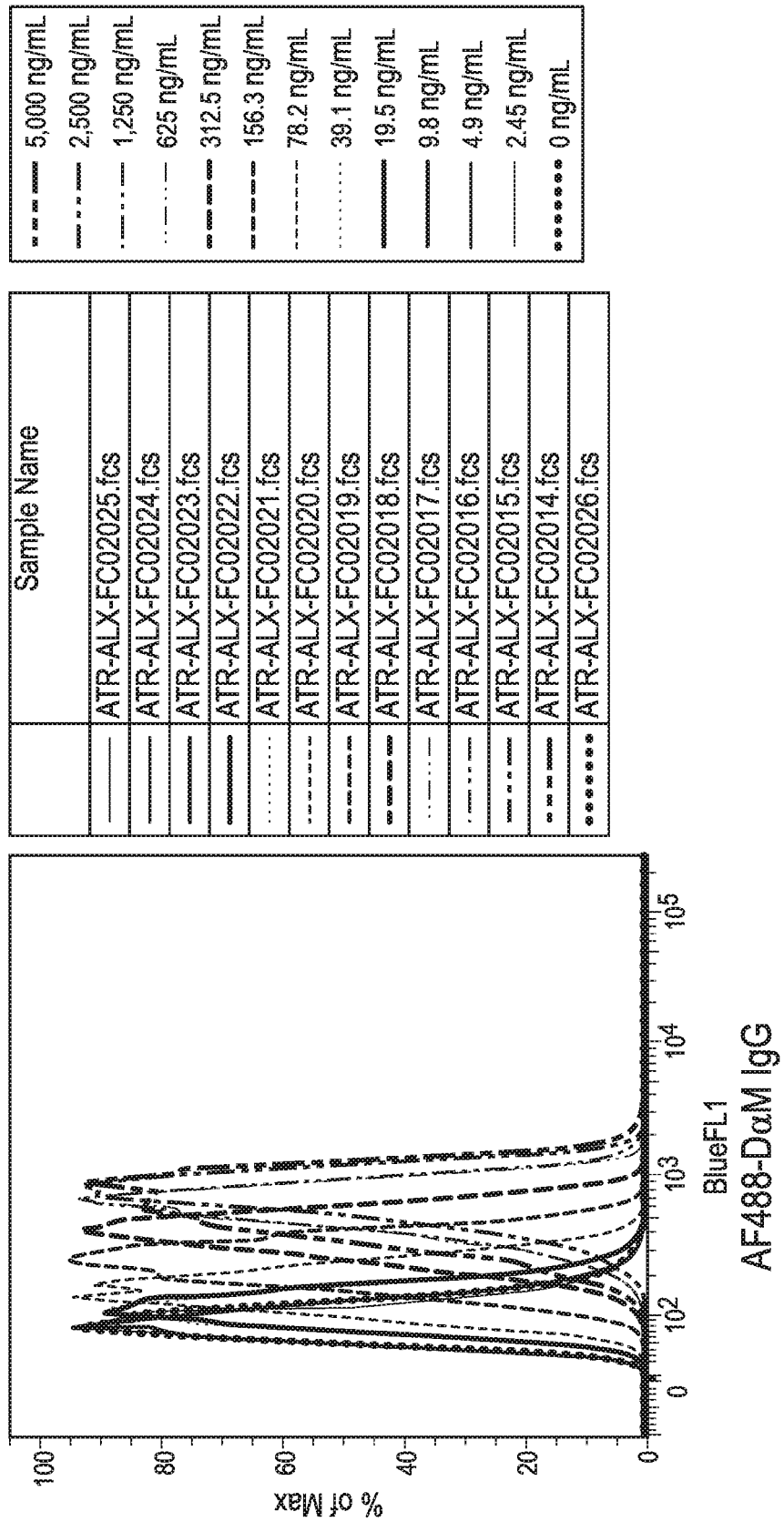
FIG. 14 shows antibody JAB0505 binding to wild-type C2C12 cells by flow cytometry at multiple antibody concentrations.
Figure 15:
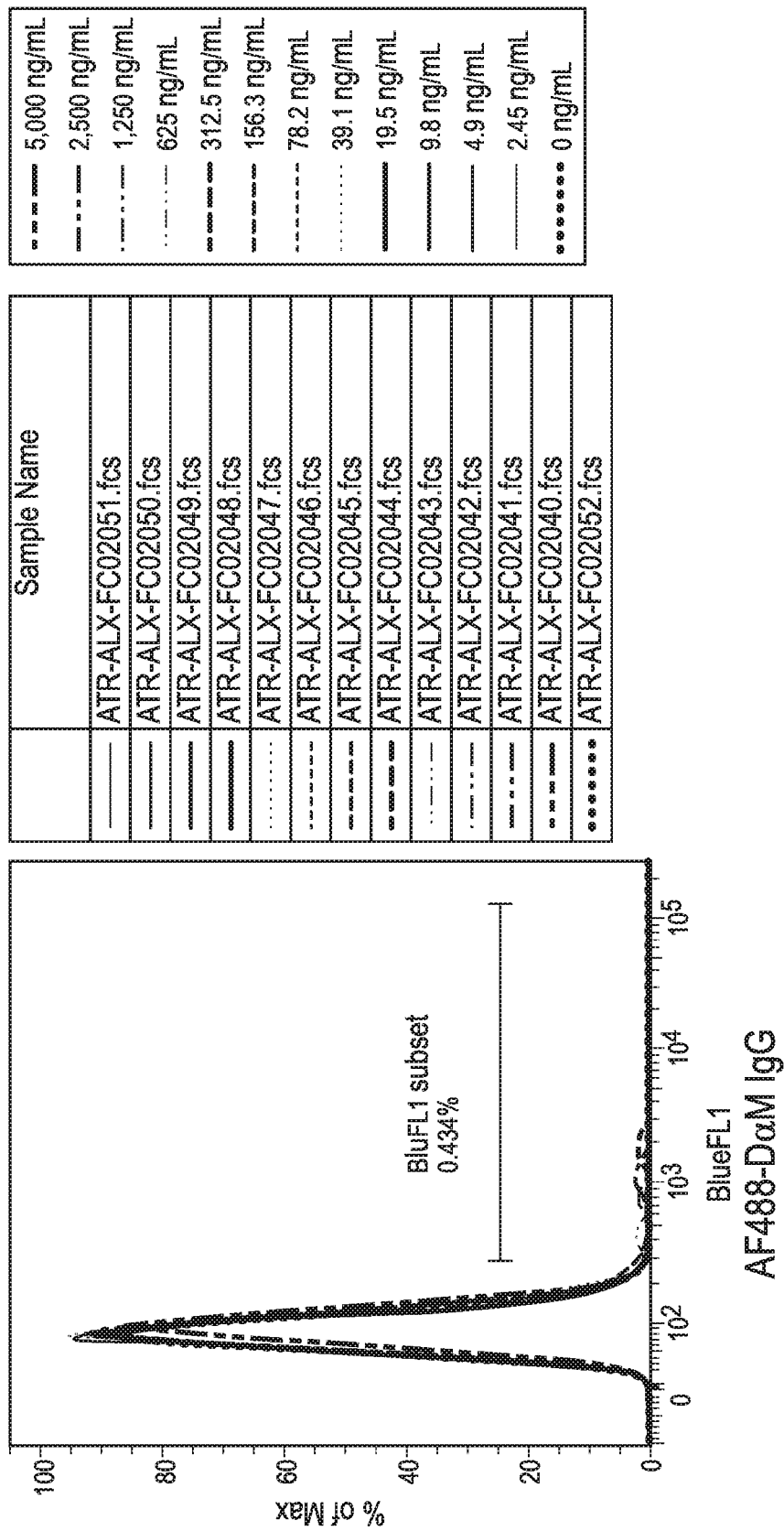
FIG. 15 shows lack of binding of antibody JAB0505 to ALK2 knock-out C2C12 cells at multiple antibody concentrations.

As shown in FIG. 13, 13 of the 18 affinity matured mAb anti-ALK2 variants demonstrated significantly increased potency in the BRE luciferase assay over parent mAb JAB0481. Also, the affinity matured variants were shown to completely inhibit BMP9-mediated ALK2 signaling, decreasing to baseline the BMP-dependent transcription of luciferase as measured by luminescence. However, parent mAb JAB0481 was not able to completely inhibit ALK2 signaling at the highest concentration tested (73.3 nM), and the resulting luminescence remained significantly above baseline values (FIG. 13). The $IC_{50}$ of the affinity matured variants, shown in Table 3, ranged from 1.388 pM to 1.353 nM.

TABLE 3

$IC_{50}$ values for inhibition for BMP9-mediated ALK2 signaling by affinity matured variants in the BRE-luciferase assay

| Antibody | $IC_{50}$ (nM) |
| --- | --- |
| JAB0496 | 1.22 |
| JAB0498 | 0.541 |
| JAB0501 | 0.204 |
| JAB0502 | 1.35 |
| JAB0503 | 0.986 |
| JAB0504 | 0.253 |
| JAB0505 | 0.139 |
| JAB0506 | 0.219 |
| JAB0507 | 0.616 |
| JAB0508 | 0.469 |
| JAB0512 | 0.217 |

The specificity of the affinity matured antibodies was further assessed by measuring the binding of the antibodies to baculovirus particles by ELISA. In principle, antibodies with low affinity to baculovirus particles have lower risk of non-specific binding interactions that may lead to poor PK in vivo (Hotzel et al., *Mabs* 2012; 4(6):753-60).

To measure non-specific binding to baculovirus particles, ELISA plates were coated overnight at 4° C. with high titer Baclovirus Particle Stock (BlueSky Biotech) diluted in carbonate coating buffer pH 9.5. Plates were washed, blocked for one hour, washed, and anti-Alk2 antibodies diluted to 1 μM were added. The plates were incubated at room temperature for one hour, washed, and HRP-conjugated goat anti-mouse IgG secondary antibody (Thermo Scientific catalog number A-10668) was added and plates incubated for one hour at room temperature. Plates were then washed and developed with TMP ELISA substrate (Thermo Scientific catalog number 34029). The absorbance at 450 nM was then obtained using a plate reader. Baclovirus Particle binding scores (BVP scores) were calculated by dividing the absorbance for the antibodies by the absorbance of the no-antibody background controls. A BPV score greater than 5 indicates a high risk for non-specific binding and rapid clearance in vivo.

Figure 16:
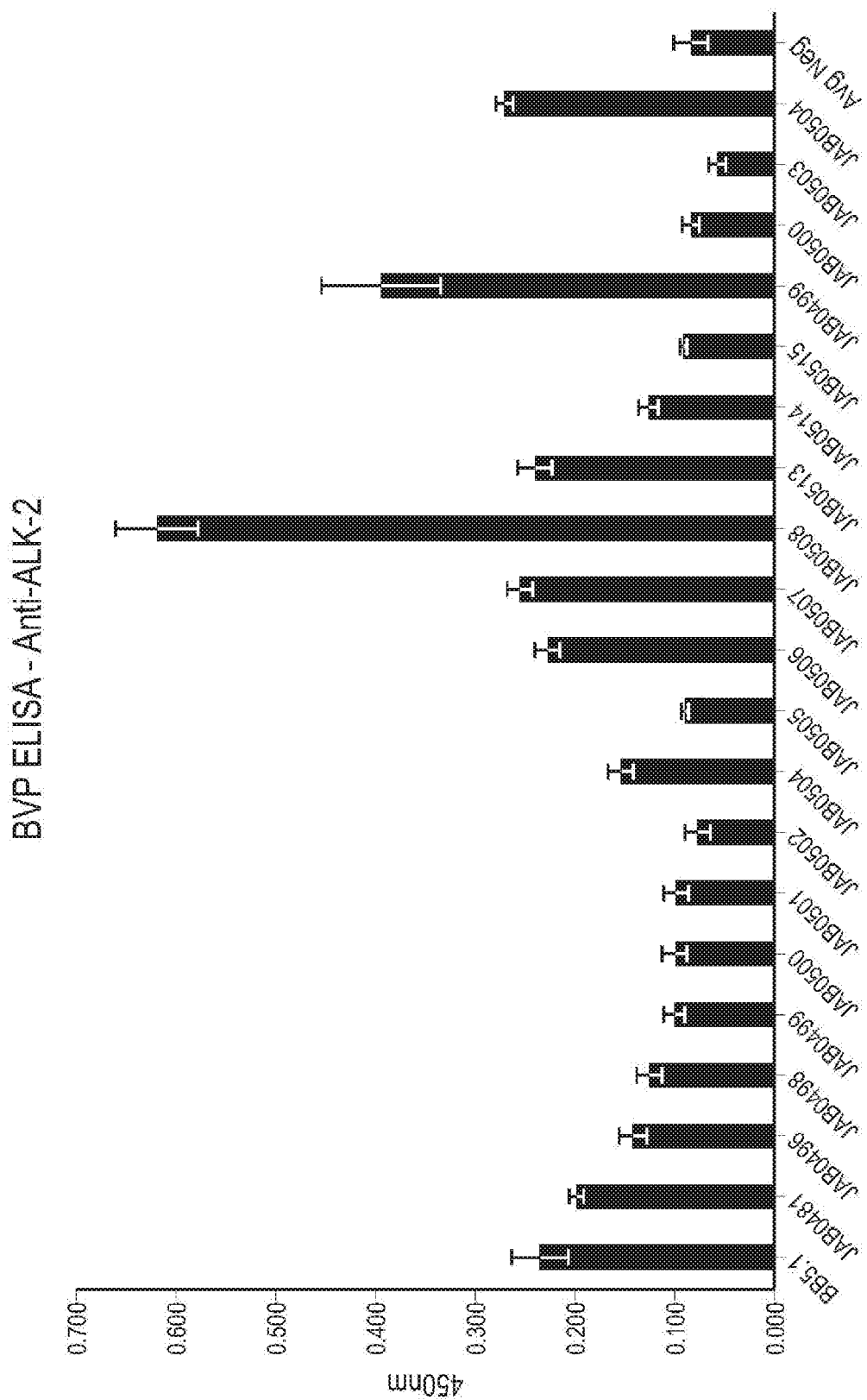
FIG. 16 shows evaluation of non-specific baculovirus particle-binding of JAB0481 and affinity matured antibodies. Standard deviation bars for n=3 shown.

FIG. 16 provides the absorbance values at 450 nM for JAB0481 and affinity matured antibodies. Table 4 provides the absorbance values and BVP scores for the antibodies tested. Antibody JAB0508 was the only antibody found to have a high risk for non-specific binding.

TABLE 4

Binding of anti-Alk2 antibodies to baculovirus particles and BPV scores

| Sample | Lot # | Average 450 nm | Stdev | BVP Score |
| --- | --- | --- | --- | --- |
| BB5.1 | 14OCT14Alxn | 0.236 | 0.029 | 2.8 |
| JAB0481 | 042015JC | 0.200 | 0.008 | 2.3 |
| JAB0496 | 043015JC | 0.143 | 0.014 | 1.7 |
| JAB0498 | 043015JC | 0.127 | 0.013 | 1.5 |
| JAB0499 | 043015JC | 0.102 | 0.011 | 1.2 |
| JAB0500 | 043015JC | 0.102 | 0.013 | 1.2 |
| JAB0501 | 043015JC | 0.1 | 0.008 | 1.2 |
| JAB0502 | 043015JC | 0.078 | 0.009 | 0.9 |
| JAB0504 | 043015JC | 0.155 | 0.014 | 1.8 |
| JAB0505 | 043015JC | 0.091 | 0.003 | 1.1 |
| JAB0506 | 043015JC | 0.228 | 0.016 | 2.7 |
| JAB0507 | 043015JC | 0.255 | 0.015 | 3 |
| JAB0508 | 043015JC | 0.619 | 0.041 | 7.3 |
| JAB0513 | 051715JC | 0.242 | 0.017 | 2.8 |
| JAB0514 | 051715JC | 0.129 | 0.009 | 1.5 |
| JAB0515 | 051715JC | 0.093 | 0.004 | 1.1 |
| JAB0499 | 051715JC | 0.395 | 0.059 | 4.6 |
| JAB0500 | 051715JC | 0.085 | 0.010 | 1 |
| JAB0503 | 043015JC | 0.059 | 0.009 | 0.7 |
| JAB0504 | 050415JC | 0.271 | 0.010 | 3.2 |
| Avg Neg | | 0.085 | 0.016 | 1.0* |

Figure 17:
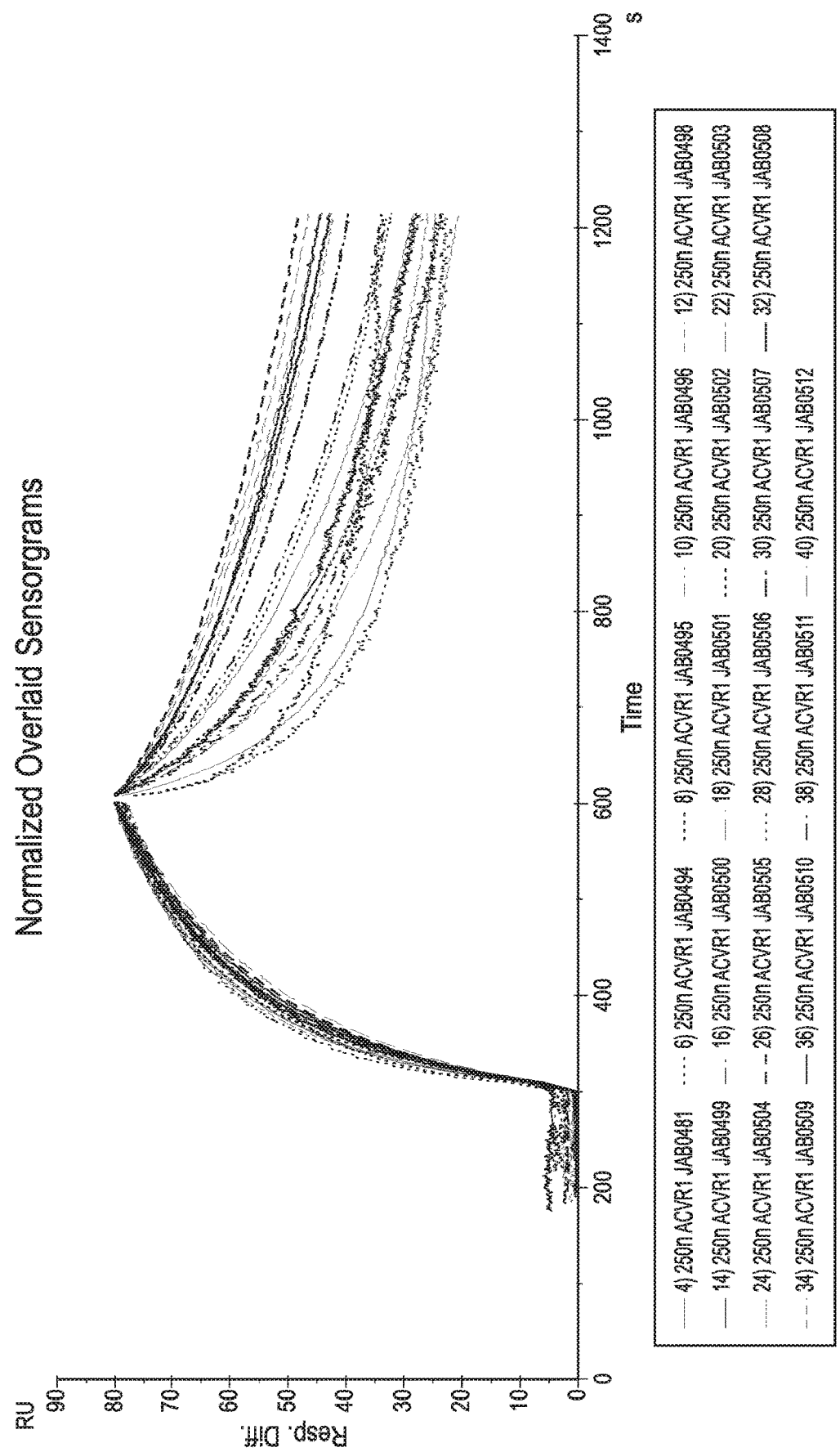
FIG. 17 shows surface plasmon resonance sensorgrams of JAB0481 and affinity matured variants to the ECD of ALK2.

The binding kinetics of affinity matured antibody binding to the extracellular domain of ALK2 was determined by Biacore analysis as described above. FIG. 17 provides the normalized overlaid Biacore sensorgrams for the affinity matured antibodies and the parental antibody, JAB0481, showing that the process of affinity maturation yielded mAb variants with improved affinities for ALK2 as shown by reduction in the off-rate. Table 5 provides the binding kinetic parameters determined by Biacore for these antibodies.

TABLE 5

Biacore binding kinetics for affinity matured mAbs binding to the ALK2 ECD

| Sample | ka (1/Ms) | kd (1/s) | $K_D$ (M) | Chi2 |
| --- | --- | --- | --- | --- |
| JAB0481 | $3.91 \times 10^4$ | $5.16 \times 10^{-3}$ | $1.32 \times 10^{-7}$ | 2.23 |
| JAB0494 | $4.16 \times 10^4$ | $6.42 \times 10^{-3}$ | $1.54 \times 10^{-7}$ | 0.38 |
| JAB0495 | $4.16 \times 10^4$ | $4.59 \times 10^{-3}$ | $1.10 \times 10^{-7}$ | 0.58 |
| JAB0496 | $4.51 \times 10^4$ | $2.76 \times 10^{-3}$ | $6.11 \times 10^{-8}$ | 2.02 |
| JAB0498 | $4.42 \times 10^4$ | $1.01 \times 10^{-3}$ | $2.28 \times 10^{-8}$ | 1.73 |
| JAB0499 | $4.45 \times 10^4$ | $9.25 \times 10^{-4}$ | $2.08 \times 10^{-8}$ | 1.23 |

TABLE 5-continued

Biacore binding kinetics for affinity matured mAbs binding to the ALK2 ECD

| Sample | ka (1/Ms) | kd (1/s) | $K_D$ (M) | Chi2 |
|---|---|---|---|---|
| JAB0500 | $4.66 \times 10^4$ | $1.49 \times 10^{-3}$ | $3.20 \times 10^{-8}$ | 2.36 |
| JAB0501 | $3.79 \times 10^4$ | $9.29 \times 10^{-4}$ | $2.45 \times 10^{-8}$ | 1.51 |
| JAB0502 | $5.23 \times 10^4$ | $2.11 \times 10^{-3}$ | $4.03 \times 10^{-8}$ | 2.08 |
| JAB0503 | $4.67 \times 10^4$ | $3.36 \times 10^{-3}$ | $7.19 \times 10^{-8}$ | 1.82 |
| JAB0504 | $5.43 \times 10^4$ | $1.73 \times 10^{-3}$ | $3.19 \times 10^{-8}$ | 2.52 |
| JAB0505 | $4.03 \times 10^4$ | $8.39 \times 10^{-4}$ | $2.08 \times 10^{-8}$ | 1.85 |
| JAB0506 | $4.52 \times 10^4$ | $1.55 \times 10^{-3}$ | $3.44 \times 10^{-8}$ | 2.46 |
| JAB0507 | $4.72 \times 10^4$ | $1.16 \times 10^{-3}$ | $2.46 \times 10^{-8}$ | 1.66 |
| JAB0508 | $4.62 \times 10^4$ | $9.89 \times 10^{-4}$ | $2.14 \times 10^{-8}$ | 1.61 |
| JAB0509 | $3.61 \times 10^4$ | $2.61 \times 10^{-3}$ | $7.22 \times 10^{-8}$ | 0.17 |
| JAB0510 | $3.80 \times 10^4$ | $2.65 \times 10^{-3}$ | $6.96 \times 10^{-8}$ | 0.12 |
| JAB0511 | $4.61 \times 10^4$ | $2.30 \times 10^{-3}$ | $5.00 \times 10^{-8}$ | 0.26 |
| JAB0512 | $4.37 \times 10^4$ | $8.59 \times 10^{-3}$ | $1.97 \times 10^{-8}$ | 1.39 |

Example 7: Humanization of Anti-ALK2 Antibodies

This Example describes the humanization of monoclonal anti-ALK2 antibodies, including the affinity matured versions of JAB0481.

In-silico design of the humanized JAB0481 was performed by Ig blast of the murine VL and VH sequences to human germlines. pJVL481 has 72% matched identity to the light chain germline IGKV1-39*01, and 55% sequence identity to heavy chain germline (IGHV1-46*02). Complimentary determining regions (CDRs) were determined by alignment to referenced germlines and according to Kabat numbering definitions. The CDRs of pJVH481 were transposed onto frameworks and cloned as a human G2/G4 monoclonal antibody (Table 6). The same germlines were utilized to graft the heavy and light chain sequences for affinity matured variants JAB0501 and JAB0505. In addition, the four other top matched human germlines were used to graft the CDRs of JAB0501 and JAB0505, and were cloned and tested similarly.

Example 8: Binding of Anti-ALK2 Antibodies to Human Tissue

The resulting mAbs will be further evaluated for their binding to human ALK2 using the methods described in Examples 4-6, and a commercially available normal human tissue panel according to standard procedures which are available from commercial Contract Research Organizations.

Example 9: Effects of Anti-ALK2 Antibodies in an Osteopenia Model

Ovariectomized (OVX) C57Bl/6 mice develop osteopenia, and thus are an accepted model for determining the in vivo efficacy of therapeutics to treat osteopenia. The anti-ALK2 antibody JAB0505 from previous Examples was tested for efficacy in this model of osteopenia.

Eight-week old female C57Bl/6J mice (Jackson Laboratories, Bar Harbor, ME) were bilaterally ovariectomized (n=20) and aged six weeks following surgery to induce osteopenia. Pre-study (Day −14) and baseline (Day −5) in vivo μCT scans were performed on all hindlimbs using the Quantum FX μCT Cabinet X-Ray System (PerkinElmer Inc., Waltham, MA). Scans were performed with the following parameters: voltage=90 kV, current=180 μA, FOV=40 mm, and acquisition time=2 minutes. Beginning on study Day 0, OVX mice were treated with 10 mg/kg of either anti-ALK2 monoclonal antibody (n=10) (JAB0505) or IgG1 isotype control (R&D Systems) antibody (n=5) via intraperitoneal injection, 3 times/week for 4 weeks. Non-treated OVX mice (n=5) and aged-matched, non-ovariectomized C57Bl6/J mice (n=10) were included as controls. Additional in vivo μCT scans were performed on all mice on study Days 14 and 28 as described above to assess changes in femoral bone mineral density (BMD) as a result of treatment. Ex vivo μCT scans were individually acquired on harvested femurs using the following parameters: voltage=90 kV, current=180 μA, FOV=20 mm, and acquisition time=4.5 minutes. All animal studies were conducted according to provisions of the Animal Welfare Act and the principles of the Guide for the Care and Use of Laboratory Animals.

Quantitative analysis of μCT images was performed using AccuCT 1.0 Advanced Analysis software (PerkinElmer Inc., Waltham, MA). Longitudinal in vivo measurements (study Days −14, −5, 14, and 28) of femoral BMD were calculated using the software's Bone Growth workflow. All images were calibrated to a 5-insert hydroxyapatite resin phantom (QRM, Moehrendorf, Germany) standard. Quantitative analyses of Day 28 ex vivo femoral bone morphology parameters, including Bone Volume (Tb.BV), Trabecular Total Volume (Tb.TV), Bone Surface (Tb.BS), Bone Volume Fraction (Tb.BV/TV), Specific Bone Surface (Tb.BS.BV), Trabecular Thickness (Tb.Th), Cortical Total Volume (Ct.TV), Average Cortical Thickness (Ct.Th), Total Volume (TV), Cortical Periosteal Area (Ps.Ar), and Endocortical Area (Ec.Ar) were performed using the software's ASBMR Morphology workflow. Statistical analyses were performed using GraphPad Prism 7 (La Jolla, CA).

Figure 18:
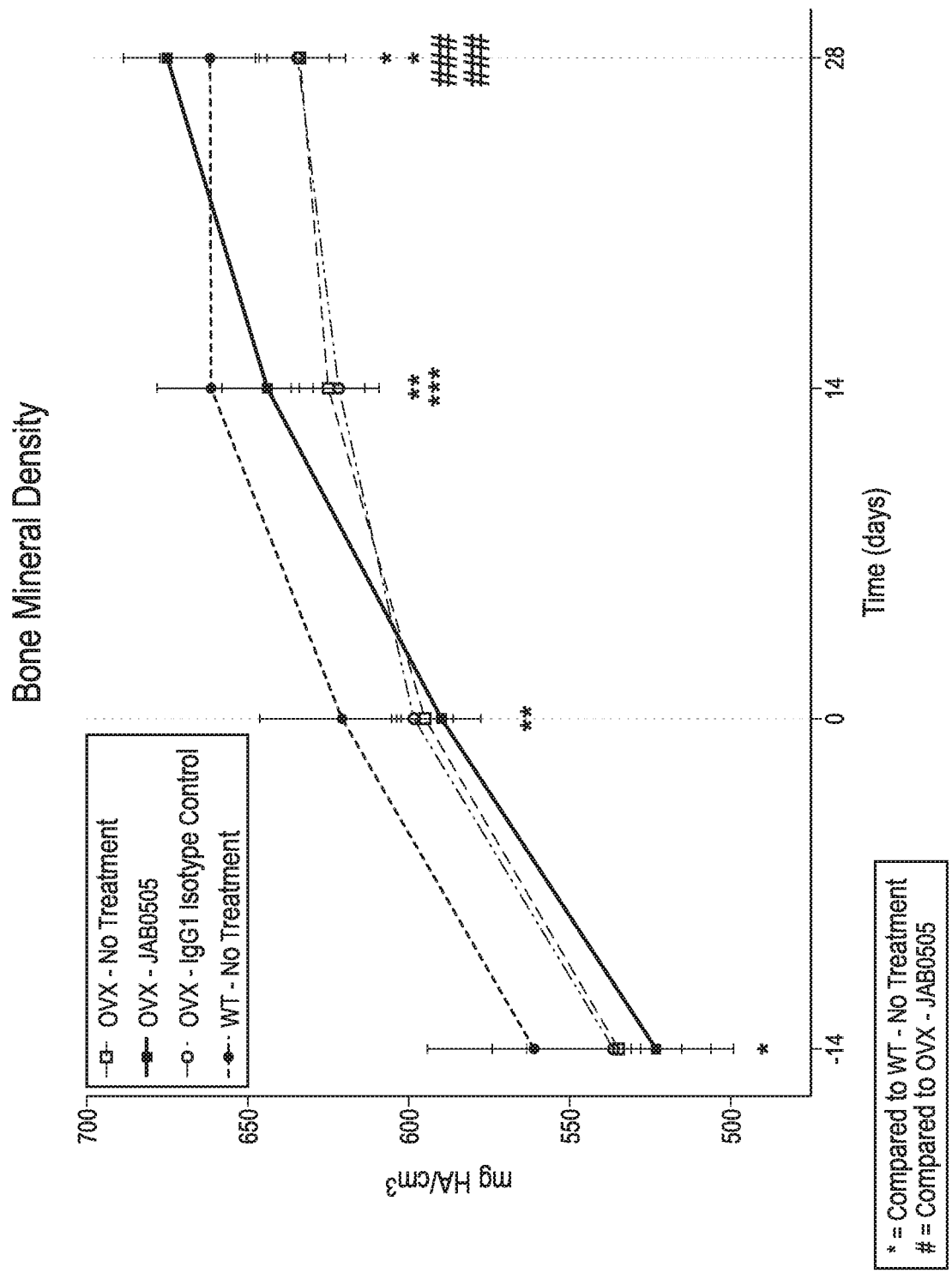
FIG. 18 shows the change in bone mineral density in OVX mice treated with antibody JAB0505 (* or # corresponds to <0.05;  or ## correspond to <0.01; * or ### correspond to <0.001, and **** or #### correspond to <0.0001; * indicates comparison to untreated WT mice and # indicates comparison to OVX treated with JAB0505).
Figure 19:
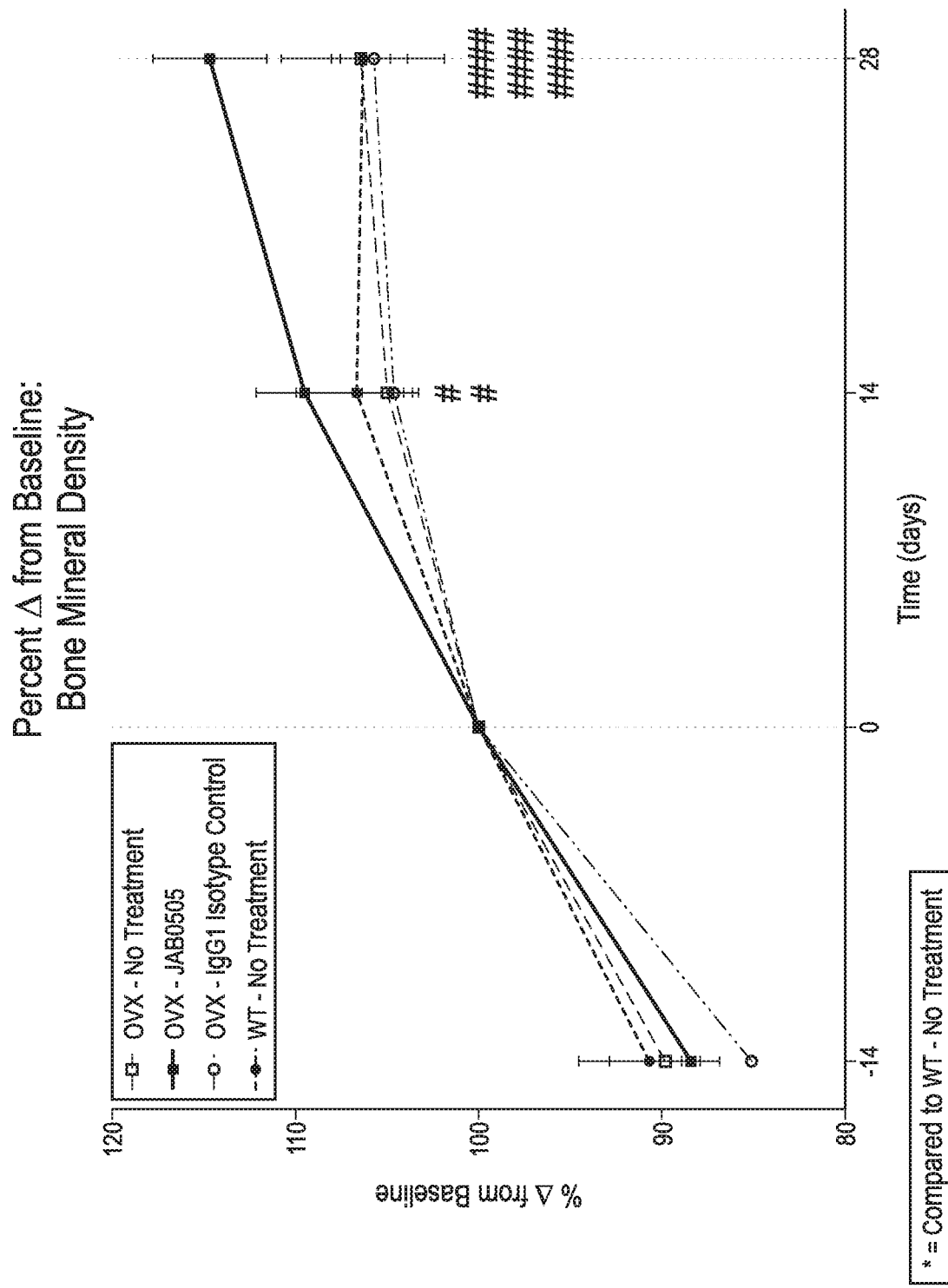
FIG. 19 shows the percent change from baseline in bone mineral density in OVX mice treated with antibody JAB0505 (* or # corresponds to <0.05;  or ## correspond to <0.01; * or ### correspond to <0.001, and **** or #### correspond to <0.0001; * indicates comparison to untreated WT mice, and # indicates comparison to OVX treated with JAB0505).

As shown in FIGS. 18 and 19, BMD and the percent change from baseline of BMD increased in vivo over 28 days upon three times per week treatment with 10 mg/kg JAB0505 compared to control animals. Similarly, as shown in FIGS. 20 and 21, when normalized to total bone volume, the percent change from baseline as a function of total bone volume increased in JAB0505 treated subjects compared to controls. Evaluation of body weight in all groups confirmed no generalized negative effects from the treatment or the controls (FIG. 22).

As shown in FIG. 23, average cortical thickness significantly increased with JAB0505 treatment relative to controls, and was restored to wild-type levels. Decreases in average cortical volume are associated with bone mineralization disorders such as osteopenia and osteoporosis.

Other measurements of bone surface (FIG. 24A), total volume (FIG. 24B), bone volume (FIG. 24C), cortical total volume (FIG. 24D), trabecular total volume (FIG. 24E), bone volume fraction (FIG. 24F), trabecular thickness (FIG. 24G), specific bone surface (FIG. 24H), cortical periosteal area (FIG. 24I), and endocortical area (FIG. 24J), showed insignificant differences between treated and control animals, confirming that treatment with an anti-ALK2 mAb (exemplified by JAB0505), while increasing cortical density, did not adversely disrupt bone morphology or growth.

TABLE 6

Summary of sequences

| SEQ ID | Description | Sequence |
|---|---|---|
| 1 | Mouse ALK2, signal peptide underlined | MVDGVMILPVLMMMAFPSPSVEDEKPKVNQKLYMCVCEGLSCGNE DHCEGQQCFSSLSINDGFHVYQKGCFQVYEQGKMTCKTPPSPGQA VECCQGDWCNRNITAQLPTKGKSFPGTQNFHLEVGLIILSVVFAV CLLACILGVALRKFKRRNQERLNPRDVEYGTIEGLITTNVGDSTL AELLDHSCTSGSGSGLPFLVQRTVARQITLLECVGKGRYGEVWRG SWQGENVAVKIFSSRDEKSWFRETELYNTVMLRHENILGFIASDM TSRHSSTQLWLITHYHEMGSLYDYLQLTTLDTVSCLRIVLSIASG LAHLHIEIFGTQGKSAIAHRDLKSKNILVKKNGQCCIADLGLAVM HSQSTNQLDVGNNPRVGTKRYMAPEVLDETIQVDCFDSYKRVDIW AFGLVLWEVARRMVSNGIVEDYKPPFYDVVPNDPSFEDMRKVVCV DQQRPNIPNRWFSDPTLTSLAKLMKECWYQNPSARLTALRIKKTL TKIDNSLDKLKTDC |
| 2 | Human ALK2; signal peptide underlined | MVDGVMILPVLIMIALPSPSMEDEKPKVNPKLYMCVCEGLSCGNE DHCEGQQCFSSLSINDGFHVYQKGCFQVYEQGKMTCKTPPSPGQA VECCQGDWCNRNITAQLPTKGKSFPGTQNFHLEVGLIILSVVFAV CLLACLLGVALRKFKRRNQERLNPRDVEYGTIEGLITTNVGDSTL ADLLDHSCTSGSGSGLPFLVQRTVARQITLLECVGKGRYGEVWRG SWQGENVAVKIFSSRDEKSWFRETELYNTVMLRHENILGFIASDM TSRHSSTQLWLITHYHEMGSLYDYLQLTTLDTVSCLRIVLSIASG LAHLHIEIFGTQGKPAIAHRDLKSKNILVKKNGQCCIADLGLAVM HSQSTNQLDVGNNPRVGTKRYMAPEVLDETIQVDCFDSYKRVDIW AFGLVLWEVARRMVSNGIVEDYKPPFYDVVPNDPSFEDMRKVVCV DQQRPNIPNRWFSDPTLTSLAKLMKECWYQNPSARLTALRIKKTL TKIDNSLDKLKTDC |
| 3 | Human ALK2 extracellular domain | MEDEKPKVNPKLYMCVCEGLSCGNEDHCEGQQCFSSLSINDGFHV YQKGCFQVYEQGKMTCKTPPSPGQAVECCQGDWCNRNITAQLPTK GKSFPGTQNFHLE |
| 4 | Human ALK2 ECD with signal peptide | MVDGVMILPVLIMIALPSPSMEDEKPKVNPKLYMCVCEGLSCGNE DHCEGQQCFSSLSINDGFHVYQKGCFQVYEQGKMTCKTPPSPGQA VECCQGDWCNRNITAQLPTKGKSFPGTQNFHLE |
| 5 | Human ALK2 ECD with signal peptide and N-term. GST tag | MVDGVMILPVLIMIALPSPSMSPILGYWKIKGLVQPTRLLLEYLE EKYEEHLYERDEGDKWRNKKFELGLEFPNLPYYIDGDVKLTQSMA IIRYIADKHNMLGGCPKERAEISMLEGAVLDIRYGVSRIAYKSDF ETLKVDFLSKLPEMLKMFEDRLCHKTYLNGDHVTHPDFMLYDALD VVLYMDPMCLDAFPKLVCFKKRIEAIPQIDKYLKSSKYIAWPLQG WQATFGGGDHPPKSDGGSGMEDEKPKVNPKLYMCVCEGLSCGNED HCEGQQCFSSLSINDGFHVYQKGCFQVYEQGKMTCKTPPSPGQAV ECCQGDWCNRNITAQLPTKGKSFPGTQNFHLE |
| 6 | Human ALK2 ECD with N-term. GST tag | MVMSPILGYWKIKGLVQPTRLLLEYLEEKYEEHLYERDEGDKWRN KKFELGLEFPNLPYYIDGDVKLTQSMAIIRYIADKHNMLGGCPKE RAEISMLEGAVLDIRYGVSRIAYKSDFETLKVDFLSKLPEMLKMF EDRLCHKTYLNGDHVTHPDFMLYDALDVVLYMDPMCLDAFPKLVC FKKRIEAIPQIDKYLKSSKYIAWPLQGWQATFGGGDHPPKSDGGS GMEDEKPKVNPKLYMCVCEGLSCGNEDHCEGQQCFSSLSINDGFH VYQKGCFQVYEQGKMTCKTPPSPGQAVECCQGDWCNRNITAQLPT KGKSFPGTQNFHLE |
| 7 | Human ALK ECD with C-terminal transmembrane domain | MEDEKPKVNPKLYMCVCEGLSCGNEDHCEGQQCFSSLSINDGFHV YQKGCFQVYEQGKMTCKTPPSPGQAVECCQGDWCNRNITAQLPTK GKSFPGTQNFHLEVGLIILSVVFAVCLLACLLGVAL |
| 8 | Human IgG1 heavy chain constant region | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKKVEPKSCDKTHTCPPCPAPELLGGPSVFLFPPKPKDTLM ISRTPEVTCVVVDVSHEDPEVKFNWYVDGVEVHNAKTKPREEQYN STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEAL HNHYTQKSLSLSPGK |
| 9 | IgG2/4 hybrid Fc | ASTKGPSVFPLAPCSRSTSESTAALGCLVKDYFPEPVTVSWNSGA LTSGVHTFPAVLQSSGLYSLSSVVTVPSSNFGTQTYTCNVDHKPS NTKVDKTVERKCCVECPPCPAPPVAGPSVFLFPPKPKDTLMISRT PEVTCVVVDVSQEDPEVQFNWYVDGVEVHNAKTKPREEQFNSTYR VVSVLTVLHQDWLNGKEYKCKVSNKGLPSSIEKTISKAKGQPREP QVYTLPPSQEEMTKNQVSLTCLVKGFYPSDIAVEWESNGQPENNY KTTPPVLDSDGSFFLYSRLTVDKSRWQEGNVFSCSVMHEALHNHY TQKSLSLSLGK |

TABLE 6-continued

Summary of sequences

| SEQ ID | Description | Sequence |
|---|---|---|
| 10 | JAB0399 VHCDR1 | GFNIKDSLMH |
| 11 | JAB0399 VHCDR2 | IDPEDGETKYAPNFQD |
| 12 | JAB0399 VHCDR3 | YTSDYYTMDY |
| 13 | JAB0399 VLCDR1 | LASQTIGTWLA |
| 14 | JAB0399 VLCDR2 | AATSLAD |
| 15 | JAB0399 VLCDR3 | QQLYSTPWT |
| 16 | JAB0399 VH | EVQLQQSGAELVRPGASVRLSCTASGFNIKDSLMHWVKQRPEQGL<br>EWIGWIDPEDGETKYAPNFQDKATITAVTSSNTAYLQLSSLTSED<br>SAIYYCARYTSDYYTMDYWGQGTSVTVSS |
| 17 | JAB0399 VL | DIQMTQSPASQSASLGESVTFTCLASQTIGTWLAWYQQKPGKSPQ<br>LLIYAATSLADGVPSRFSGSGSGTKFSFKISSLQAEDFASYYCQQ<br>LYSTPWTFGGGTKLEIK |
| 18 | JAB0399 HC<br>Constant region is<br>underlined | EVQLQQSGAELVRPGASVRLSCTASGFNIKDSLMHWVKQRPEQGL<br>EWIGWIDPEDGETKYAPNFQDKATITAVTSSNTAYLQLSSLTSED<br>SAIYYCARYTSDYYTMDYWGQGTSVTVSSAKTTPPSVYPLAPGFA<br>AQTNSMVTLGCLVKGYFPEPVTVTWNSGSLSSGVHTFPAVLQSDL<br>YTLSSSVTVPSSTWPSQTVTCNVAHPASSTKVDKKIVPRDCGCKP<br>CICTVPEVSSVFIFPPKPKDVLTITLTPKVTCVVVDISKDDPEVQ<br>FSWFVDDVEVHTAQTKPREEQINSTFRSVSELPIMHQDWLNGKEF<br>KCRVNSAAFPAPIEKTISKTKGRPKAPQVYTIPPPKEQMAKDKVS<br>LTCMITNFFPEDITVEWQWNGQPAENYKNTQPIMDTDGSYFVYSK<br>LNVQKSNWEAGNTFTCSVLHEGLHNHHTEKSLSHSPGK |
| 19 | JAB0399 LC<br>Constant region is<br>underlined | DIQMTQSPASQSASLGESVTFTCLASQTIGTWLAWYQQKPGKSPQ<br>LLIYAATSLADGVPSRFSGSGSGTKFSFKISSLQAEDFASYYCQQ<br>LYSTPWTFGGGTKLEIKRADAAPTVSIFPPSSEQLTSGGASVVCF<br>LNNFYPKDINVKWKIDGSERQNGVLNSWTDQDSKDSTYSMSSTLT<br>LTKDEYERHNSYTCEATHKTSTSPIVKSFNRNEC |
| 20 | JAB0481 VHCDR1 | GFNIKDSLMH |
| 21 | JAB0481 VHCDR2 | IDPEDGETKYAPNFQD |
| 22 | JAB0481 VHCDR3 | YTSDYYTMDY |
| 23 | JAB0481 VLCDR1 | LASQTIGTWLA |
| 24 | JAB0481 VLCDR2 | AATSLAD |
| 25 | JAB0481 VLCDR3 | QQLYSTPWT |
| 26 | JAB0481 VH | EVQLQQSGAELVRPGASVRLSCTASGFNIKDSLMHWVKQRPEQGL<br>EWIGWIDPEDGETKYAPNFQDKATITAVTSSNTAYLQLSSLTSED<br>SAIYYCARYTSDYYTMDYWGQGTSVTVSS |
| 27 | JAB0481 VL | DIQMTQSPASQSASLGESVTFTCLASQTIGTWLAWYQQKPGKSPQ<br>LLIYAATSLADGVPSRFSGSGSGTKFSFKISSLQAEDFASYYCQQ<br>LYSTPWTFGGGTKLEIK |
| 28 | JAB0481 HC<br>Constant region is<br>underlined | EVQLQQSGAELVRPGASVRLSCTASGFNIKDSLMHWVKQRPEQGL<br>EWIGWIDPEDGETKYAPNFQDKATITAVTSSNTAYLQLSSLTSED<br>SAIYYCARYTSDYYTMDYWGQGTSVTVSSAKTTPPSVYPLAPGSA<br>AQTNSMVTLGCLVKGYFPEPVTVTWNSGSLSSGVHTFPAVLQSDL<br>YTLSSSVTVPSSTWPSQTVTCNVAHPASSTKVDKKIVPRDCGCKP<br>CICTVPEVSSVFIFPPKPKDVLTITLTPKVTCVVVDISKDDPEVQ<br>FSWFVDDVEVHTAQTKPREEQINSTFRSVSELPIMHQDWLNGKEF<br>KCRVNSAAFPAPIEKTISKTKGRPKAPQVYTIPPPKEQMAKDKVS<br>LTCMITNFFPEDITVEWQWNGQPAENYKNTQPIMDTDGSYFVYSK<br>LNVQKSNWEAGNTFTCSVLHEGLHNHHTEKSLSHSPGK |
| 29 | JAB0481 LC<br>Constant region is<br>underlined | DIQMTQSPASQSASLGESVTFTCLASQTIGTWLAWYQQKPGKSPQ<br>LLIYAATSLADGVPSRFSGSGSGTKFSFKISSLQAEDFASYYCQQ<br>LYSTPWTFGGGTKLEIKRADAAPTVSIFPPSSEQLTSGGASVVCF<br>LNNFYPKDINVKWKIDGSERQNGVLNSWTDQDSKDSTYSMSSTLT<br>LTKDEYERHNSYTCEATHKTSTSPWKSFNRNEC |

TABLE 6-continued

Summary of sequences

| SEQ ID | Description | Sequence |
|---|---|---|
| 30 | JAB0501 VHCDR1 | GFNIKDSLMH |
| 31 | JAB0501 VHCDR2 | IDPEDGETKYAPNFQS |
| 32 | JAB0501 VHCDR3 | YTSPYYTMDY |
| 33 | JAB0501 VLCDR1 | LASQTIGTWLA |
| 34 | JAB0501 VLCDR2 | AATSLAD |
| 35 | JAB0501 VLCDR3 | QQVYSTPWT |
| 36 | JAB0501 VH | EVQLQQSGAELVRPGASVRLSCTASGFNIKDSLMHWVKQRPEQGL EWIGWIDPEDGETKYAPNFQSKATITAVTSSNTAYLQLSSLTSED SAIYYCARYTSPYYTMDYWGQGTSVTVSS |
| 37 | JAB0501 VL | DIQMTQSPASQSASLGESVTFTCLASQTIGTWLAWYQQKPGKSPQ LLIYAATSLADGVPSRFSGSGSGTKFSFKISSLQAEDFASYYCQQ VYSTPWTFGGGTKLEIK |
| 38 | JAB0501 HC Constant region is underlined | EVQLQQSGAELVRPGASVRLSCTASGFNIKDSLMHWVKQRPEQGL EWIGWIDPEDGETKYAPNFQSKATITAVTSSNTAYLQLSSLTSED SAIYYCARYTSPYYTMDYWGQGTSVTVSSAKTTPPSVYPLAPGSA AQTNSMVTLGCLVKGYFPEPVTVTWNSGSLSSGVHTFPAVLQSDL YTLSSSVTVPSSTWPSQTVTCNVAHPASSTKVDKKIVPRDCGCKP CICTVPEVSSVFIFPPKPKDVLTITLTPKVTCVVVDISKDDPEVQ FSWFVDDVEVHTAQTKPREEQINSTFRSVSELPIMHQDWLNGKEF KCRVNSAAFPAPIEKTISKTKGRPKAPQVYTIPPPKEQMAKDKVS LTCMITNFFPEDITVEWQWNGQPAENYKNTQPIMDTDGSYFVYSK LNVQKSNWEAGNTFTCSVLHEGLHNHHTEKSLSHSPGK |
| 39 | JAB0501 LC Constant region is underlined | DIQMTQSPASQSASLGESVTFTCLASQTIGTWLAWYQQKPGKSPQ LLIYAATSLADGVPSRFSGSGSGTKFSFKISSLQAEDFASYYCQQ VYSTPWTFGGGTKLEIKRADAAPTVSIFPPSSEQLTSGGASVVCF LNNFYPKDINVKWKIDGSERQNGVLNSWTDQDSKDSTYSMSSTLT LTKDEYERHNSYTCEATHKTSTSPWKSFNRNEC |
| 40 | JAB0505 VHCDR1 | GFNIKDSLMH |
| 41 | JAB0505 VHCDR2 | IDPEDGETRYAPNFQD |
| 42 | JAB0505 VHCDR3 | YTSRYYTMEY |
| 43 | JAB0505 VLCDR1 | LASQTIGTWLA |
| 44 | JAB0505 VLCDR2 | AATSLAD |
| 45 | JAB0505 VLCDR3 | QQLYWTPWT |
| 46 | JAB0505 VH | EVQLQQSGAELVRPGASVRLSCTASGFNIKDSLMHWVKQRPEQGL EWIGWIDPEDGETRYAPNFQDKATITAVTSSNTAYLQLSSLTSED SAIYYCARYTSRYYTMEYWGQGTSVTVSS |
| 47 | JAB0505 VL | DIQMTQSPASQSASLGESVTFTCLASQTIGTWLAWYQQKPGKSPQ LLIYAATSLADGVPSRFSGSGSGTKFSFKISSLQAEDFASYYCQQ LYWTPWTFGGGTKLEIK |
| 48 | JAB0505 HC Constant region is underlined | EVQLQQSGAELVRPGASVRLSCTASGFNIKDSLMHWVKQRPEQGL EWIGWIDPEDGETRYAPNFQDKATITAVTSSNTAYLQLSSLTSED SAIYYCARYTSRYYTMEYWGQGTSVTVSSAKTTPPSVYPLAPG SAAQTNSMVTLGCLVKGYFPEPVTVTWNSGSLSSGVHTFPA VLQSDLYTLSSSVTVPSSTWPSQTVTCNVAHPASSTKVDKK IVPRDCGCKPCICTVPEVSSVFIFPPKPKDVLTITLTPKVT CVVVDISKDDPEVQFSWFVDDVEVHTAQTKPREEQINSTFR SVSELPIMHQDWLNGKEFKCRVNSAAFPAPIEKTISKTKGR PKAPQVYTIPPPKEQMAKDKVSLTCMITNFFPEDITVEWQW NGQPAENYKNTQPIMDTDGSYFVYSKLNVQKSNWEAGNTFT CSVLHEGLHNHHTEKSLSHSPGK |
| 49 | JAB0505 LC Constant region is underlined | DIQMTQSPASQSASLGESVTFTCLASQTIGTWLAWYQQKPGKSPQ LLIYAATSLADGVPSRFSGSGSGTKFSFKISSLQAEDFASYYCQQ LYWTPWTFGGGTKLEIKRADAAPTVSIFPPSSEQLTSGGASVVCF LNNFYPKDINVKWKIDGSERQNGVLNSWTDQDSKDSTYSMSSTLT LTKDEYERHNSYTCEATHKTSTSPWKSFNRNEC |

TABLE 6-continued

Summary of sequences

| SEQ ID | Description | Sequence |
|---|---|---|
| 50 | Signal sequence | MGWSCIILFLVATATGVHS |
| 51 | Human ALK2 extracellular domain; nucleic acid | ATGGAGGACGAAAAGCCTAAAGTGAATCCCAAATTGTATATGTGC GTCTGCGAAGGACTGTCATGTGGTAATGAAGATCATTGCGAAGGG CAACAATGCTTCAGCAGCTTGTCAATCAACGACGGATTTCACGTG TATCAAAAAGGATGTTTCCAAGTGTACGAACAAGGTAAAATGACT TGCAAAACGCCACCTTCCCCGGGACAAGCGGTCGAATGTTGTCAG GGCGATTGGTGTAATCGCAATATCACTGCACAGCTCCCGACCAAG GGAAAGTCGTTTCCGGGCACCCAAAATTTTCATCTCGAGT |
| 52 | Human ALK2 ECD with signal peptide; nucleic acid | ATGGTCGACGGCGTTATGATCCTGCCGGTGCTTATCATGATCGCC CTCCCATCGCCGTCCATGGAGGACGAAAAGCCTAAAGTGAATCCC AAATTGTATATGTGCGTCTGCGAAGGACTGTCATGTGGTAATGAA GATCATTGCGAAGGGCAACAATGCTTCAGCAGCTTGTCAATCAAC GACGGATTTCACGTGTATCAAAAAGGATGTTTCCAAGTGTACGAA CAAGGTAAAATGACTTGCAAAACGCCACCTTCCCCGGGACAAGCG GTCGAATGTTGTCAGGGCGATTGGTGTAATCGCAATATCACTGCA CAGCTCCCGACCAAGGGAAAGTCGTTTCCGGGCACCCAAAATTTT CATCTCGAGT |
| 53 | Human ALK2 ECD with signal peptide and N-term. GST tag; nucleic acid | ATGGTCGACGGCGTTATGATCCTGCCGGTGCTTATCATGATCGCC CTCCCATCGCCGTCCATGTCCCTATACTAGGTTATTGGAAAATT AAGGGCCTTGTGCAACCCACTCGACTTCTTTTGGAATATCTTGAA GAAAAATATGAAGAGCATTTGTATGAGCGCGATGAAGGTGATAAA TGGCGAAACAAAAAGTTTGAATTGGGTTTGGAGTTTCCCAATCTT CCTTATTATATTGATGGTGATGTTAAATTAACACAGTCTATGGCC ATCATACGTTATATAGCTGACAAGCACAACATGTTGGGTGGTTGT CCAAAAGAGCGTGCAGAGATTTCAATGCTTGAAGGAGCGGTTTTG GATATTAGATACGGTGTTTCGAGAATTGCATATAGTAAAGACTTT GAAACTCTCAAAGTTGATTTTCTTAGCAAGCTACCTGAAATGCTG AAAATGTTCGAAGATCGTTTATGTCATAAAACATATTTAAATGGT GATCATGTAACCCATCCTGACTTCATGTTGTATGACGCTCTTGAT GTTGTTTTATACATGGACCCAATGTGCCTGGATGCGTTCCCAAAA TTAGTTTGTTTTAAAAAACGTATTGAAGCTATCCCACAAATTGAT AAGTACTTGAAATCCAGCAAGTATATAGCATGGCCTTTGCAGGGC TGGCAAGCCACGTTTGGTGGTGGCGACCATCCTCCAAAATCGGAT GGCGGTAGCGGGATGGAGGACGAAAAGCCTAAAGTGAATCCCAAA TTGTATATGTGCGTCTGCGAAGGACTGTCATGTGGTAATGAAGAT CATTGCGAAGGGCAACAATGCTTCAGCAGCTTGTCAATCAACGAC GGATTTCACGTGTATCAAAAAGGATGTTTCCAAGTGTACGAACAA GGTAAAATGACTTGCAAAACGCCACCTTCCCCGGGACAAGCGGTC GAATGTTGTCAGGGCGATTGGTGTAATCGCAATATCACTGCACAG CTCCCGACCAAGGGAAAGTCGTTTCCGGGCACCCAAAATTTTCAT CTCGAG |
| 54 | Human ALK2 ECD with N-term. GST tag; nucleic acid | ATGGTCATGTCCCTATACTAGGTTATTGGAAAATTAAGGGCCTT GTGCAACCCACTCGACTTCTTTTGGAATATCTTGAAGAAAAATAT GAAGAGCATTTGTATGAGCGCGATGAAGGTGATAAATGGCGAAAC AAAAAGTTTGAATTGGGTTTGGAGTTTCCCAATCTTCCTTATTAT ATTGATGGTGATGTTAAATTAACACAGTCTATGGCCATCATACGT TATATAGCTGACAAGCACAACATGTTGGGTGGTTGTCAAAAGAG CGTGCAGAGATTTCAATGCTTGAAGGAGCGGTTTTGGATATTAGA TACGGTGTTTCGAGAATTGCATATAGTAAAGACTTTGAAACTCTC AAAGTTGATTTTCTTAGCAAGCTACCTGAAATGCTGAAAATGTTC GAAGATCGTTTATGTCATAAAACATATTTAAATGGTGATCATGTA ACCCATCCTGACTTCATGTTGTATGACGCTCTTGATGTTGTTTTA TACATGGACCCAATGTGCCTGGATGCGTTCCCAAAATTAGTTTGT TTTAAAAAACGTATTGAAGCTATCCCACAAATTGATAAGTACTTG AAATCCAGCAAGTATATAGCATGGCCTTTGCAGGGCTGGCAAGCC ACGTTTGGTGGTGGCGACCATCCTCCAAAATCGGATGGCGGTAGC GGGATGGAGGACGAAAAGCCTAAAGTGAATCCCAAATTGTATATG TGCGTCTGCGAAGGACTGTCATGTGGTAATGAAGATCATTGCGAA GGGCAACAATGCTTCAGCAGCTTGTCAATCAACGACGGATTTCAC GTGTATCAAAAAGGATGTTTCCAAGTGTACGAACAAGGTAAAATG ACTTGCAAAACGCCACCTTCCCCGGGACAAGCGGTCGAATGTTGT CAGGGCGATTGGTGTAATCGCAATATCACTGCACAGCTCCCGACC AAGGGAAAGTCGTTTCCGGGCACCCAAAATTTTCATCTCGAG |
| 55 | Human ALK2 ECD with C-terminal transmembrane domain | ATGGTCGACGGCGTTATGATCCTGCCGGTGCTTATCATGATCGCC CTCCCATCGCCGTCCATGGAGGACGAAAAGCCTAAAGTGAATCCC AAATTGTATATGTGCGTCTGCGAAGGACTGTCATGTGGTAATGAA GATCATTGCGAAGGGCAACAATGCTTCAGCAGCTTGTCAATCAAC GACGGATTTCACGTGTATCAAAAAGGATGTTTCCAAGTGTACGAA CAAGGTAAAATGACTTGCAAAACGCCACCTTCCCCGGGACAAGCG GTCGAATGTTGTCAGGGCGATTGGTGTAATCGCAATATCACTGCA |

TABLE 6-continued

Summary of sequences

| SEQ ID | Description | Sequence |
|---|---|---|
|  |  | CAGCTCCCGACCAAGGGAAAGTCGTTTCCGGGCACCCAAAATTTT<br>CATCTCGAGGTGGGACTCATCATTCTGTCGGTGGTGTTCGCCGTG<br>TGCCTGCTGGCTTGCCTTCTGGGGGTCGCCCTG |
| 56 | Human IgG1 constant region | GCCTCCACCAAGGGCCCATCGGTCTTCCCCCTGGCACCCTCCTCC<br>AAGAGCACCTCTGGCGGCACAGCGGCCCTGGGCTGCCTGGTCAAG<br>GACTACTTCCCCGAACCGGTGACGGTGTCGTGGAACTCAGGCGCC<br>CTGACCAGCGGCGTGCACACCTTCCCGGCTGTCCTACAGTCCTCA<br>GGACTCTACTCCCTCAGCAGCGTGGTGACCGTGCCCTCCAGCAGC<br>TTGGGCACCCAGACCTACATCTGCAACGTGAATCACAAGCCCAGC<br>AACACCAAGGTGGACAAGAGAGTTGAGCCCAAATCTTGTGACAAA<br>ACTCACACATGCCCACCGTGCCCAGCACCTGAACTCCTGGGGGGA<br>CCGTCAGTCTTCCTCTTCCCCCCAAAACCCAAGGACACCCTCATG<br>ATCTCCCGGACCCCTGAGGTCACATGCGTGGTGGTGGACGTGAGC<br>CACGAAGACCCTGAGGTCAAGTTCAACTGGTACGTGGACGGCGTG<br>GAGGTGCATAATGCCAAGACAAAGCCGCGGGAGGAGCAGTACAAC<br>AGCACGTACCGTGTGGTCAGCGTCCTCACCGTCCTGCACCAGGAC<br>TGGCTGAATGGCAAGGAGTACAAGTGCAAGGTCTCCAACAAAGCC<br>CTCCCAGCCCCCATCGAGAAAACCATCTCCAAAGCCAAAGGGCAG<br>CCCCGAGAACCACAGGTGTACACCCTGCCCCCATCCCGGGAGGAG<br>ATGACCAAGAACCAGGTCAGCCTGACCTGCCTGGTCAAAGGCTTC<br>TATCCCAGCGACATCGCCGTGGAGTGGGAGAGCAATGGGCAGCCG<br>GAGAACAACTACAAGACCACGCCTCCCGTGCTGGACTCCGACGGC<br>TCCTTCTTCCTCTATAGCAAGCTCACCGTGGACAAGAGCAGGTGG<br>CAGCAGGGGAACGTCTTCTCATGCTCCGTGATGCATGAGGCTCTG<br>CACAACCACTACACGCAGAAGAGCCTCTCCCTGTCCCCGGGTAAA |
| 57 | IgG2/4 hybrid Fc; nucleic acid | GCCTCCACCAAGGGCCCATCCGTCTTCCCCCTGGCGCCCTGCTCC<br>AGGAGCACCTCCGAGAGCACAGCCGCCCTGGGCTGCCTGGTCAAG<br>GACTACTTCCCCGAACCGGTGACGGTGTCGTGGAACTCAGGCGCC<br>CTGACCAGCGGCGTGCACACCTTCCCGGCTGTCCTACAGTCCTCA<br>GGACTCTACTCCCTCAGCAGCGTGGTGACCGTGCCCTCCAGCAAC<br>TTCGGCACCCAGACCTACACCTGCAACGTAGATCACAAGCCCAGC<br>AACACCAAGGTGGACAAGACAGTTGAGCGCAAATGTTGTGTCGAG<br>TGCCCACCGTGCCCAGCACCACCTGTGGCAGGACCGTCAGTCTTC<br>CTCTTCCCCCCAAAACCCAAGGACACCCTCATGATCTCCCGGACC<br>CCTGAGGTCACGTGCGTGGTGGTGGACGTGAGCCAGGAAGACCCC<br>GAGGTCCAGTTCAACTGGTACGTGGATGGCGTGGAGGTGCATAAT<br>GCCAAGACAAAGCCGCGGGAGGAGCAGTTCAACAGCACGTACCGT<br>GTGGTCAGCGTCCTCACCGTCCTGCACCAGGACTGGCTGAACGGC<br>AAGGAGTACAAGTGCAAGGTCTCCAACAAAGGCCTCCCGTCCTCC<br>ATCGAGAAAACCATCTCCAAAGCCAAAGGGCAGCCCCGAGAGCCA<br>CAGGTGTACACCCTGCCCCCATCCCAGGAGGAGATGACCAAGAAC<br>CAGGTCAGCCTGACCTGCCTGGTCAAAGGCTTCTACCCCAGCGAC<br>ATCGCCGTGGAGTGGGAGAGCAATGGGCAGCCGGAGAACAACTAC<br>AAGACCACGCCTCCCGTGCTGGACTCCGACGGCTCCTTCTTCCTC<br>TACAGCAGGCTAACCGTGGACAAGAGCAGGTGGCAGGAGGGGAAT<br>GTCTTCTCATGCTCCGTGATGCATGAGGCTCTGCACAACCACTAC<br>ACACAGAAGAGCCTCTCCCTGTCTCTGGGTAAA |
| 58 | JAB0399 VHCDR1; Nucleic acid | GGCTTCAACATTAAAGACAGCCTTATGCAC |
| 59 | JAB0399 VHCDR2; nucleic acid | ATTGATCCTGAGGATGGTGAAACTAAATATGCCCCGAACTTCCAG<br>GAC |
| 60 | JAB0399 VHCDR3; nucleic acid | TATACTTCCGATTACTATACTATGGACTAC |
| 61 | JAB0399 VLCDR1; nucleic acid | CTGGCAAGTCAGACCATTGGTACATGGTTAGCA |
| 62 | JAB0399 VLCDR2; nucleic acid | GCTGCAACCAGCTTGGCAGAT |
| 63 | JAB0399 VLCDR3; nucleic acid | CAACAACTTTACAGTACTCCGTGGACG |

TABLE 6-continued

Summary of sequences

| SEQ ID | Description | Sequence |
|---|---|---|
| 64 | JAB0399 VH; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAAATAT<br>GCCCCGAACTTCCAGGACAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCGATTACTATACT<br>ATGGACTACTGGGGTCAAGGAACCTCGGTCACCGTCTCCTC |
| 65 | JAB0399 VL; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAAGTTATTACTGTCAACAA<br>CTTTACAGTACTCCGTGGACGTTCGGTGGAGGCACCAAGCTGGAA<br>ATCAAACG |
| 66 | JAB0399 HC; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAAATAT<br>GCCCCGAACTTCCAGGACAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCGATTACTATACT<br>ATGGACTACTGGGGTCAAGGAACCTCGGTCACCGTCTCCTCGGCT<br>AAAACGACACCCCCATCTGTCTATCCGCTAGCCCCTGGATTTGCT<br>GCCCAAACTAACTCCATGGTGACGCTGGGATGCCTGGTCAAGGGC<br>TATTTCCCTGAGCCAGTGACAGTGACCTGNAACTCTGGATCCCTG<br>TCCAGCGGTGTGCACACCTTCCCAGCTGTCCTGCAGTCTGACCTC<br>TACACTCTGAGCAGCTCAGTGACTGTCCCCTCCAGCACCTGGCCC<br>AGCCAGACCGTCACCTGCAACGTTGCCCACCCGGCCAGCAGCACC<br>AAGGTGGACAAGAAAATTGTGCCCAGGGATTGTGGTTGTAAGCCT<br>TGCATATGTACAGTCCCAGAAGTATCATCTGTCTTCATCTTCCCC<br>CCAAAGCCCAAGGATGTGCTCACCATTACTCTGACTCCTAAGGTC<br>ACGTGTGTTGTGGTAGACATCAGCAAGGATGATCCCGAGGTCCAG<br>TTCAGCTGGTTTGTAGATGATGTGGAGGTGCACACAGCTCAGACG<br>AAACCCCGGGAGGAGCAGATCAACAGCACTTTCCGTTCAGTCAGT<br>GAACTTCCCATCATGCACCAGGACTGGCTCAATGGCAAGGAGTTC<br>AAATGCAGGGTCAACAGTGCAGCTTTCCCTGCCCCCATCGAGAAA<br>ACCATCTCCAAAACCAAAGGCAGACCGAAGGCTCCACAGGTGTAC<br>ACCATTCCACCTCCCAAGGAGCAGATGGCCAAGGATAAAGTCAGT<br>CTGACCTGCATGATAACAAACTTCTTCCCTGAAGACATTACTGTG<br>GAGTGGCAGTGGAATGGGCAGCCAGCGGAGAACTACAAGAACACT<br>CAGCCCATCATGGACACAGATGGCTCTTACTTCGTCTACAGCAAG<br>CTCAATGTGCAGAAGAGCAACTGGGAGGCAGGAAATACTTTCACC<br>TGCTCTGTGTTACATGAGGGCCTGCACAACCACCATACTGAGAAG<br>AGCCTCTCCCACTCTCCTGGTAAATGA |
| 67 | JAB0399 LC; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAAGTTATTACTGTCAACAA<br>CTTTACAGTACTCCGTGGACGTTCGGTGGAGGCACCAAGCTGGAA<br>ATCAAACGGGCTGATGCTGCACCAACTGTATCCATCTTCCCACCA<br>TCCAGTGAGCAGTTAACATCCGGAGGTGCCTCAGTCGTGTGCTTC<br>TTGAACAACTTCTACCCCAAAGACATCAATGTCAAGTGGAAGATT<br>GATGGCAGTGAACGACAAAATGGCGTCCTGAACAGTTGGACTGAT<br>CAGGACAGCAAAGACAGCACCTACAGCATGAGCAGCACCCTCACG<br>TTGACCAAGGACGAGTATGAACGACATAACAGCTATACCTGTGAG<br>GCCACTCACAAGACATCAACTTCACCCATTGTCAAGAGCTTCAAC<br>AGGAATGAGTGTTAA |
| 68 | JAB0481 VHCDR1; Nucleic acid | GGCTTCAACATTAAAGACAGCCTTATGCA |
| 69 | JAB0481 VHCDR2; nucleic acid | ATTGATCCTGAGGATGGTGAAACTAAATATGCCCCGAACTTCCAG<br>GAC |

TABLE 6-continued

Summary of sequences

| SEQ ID | Description | Sequence |
|---|---|---|
| 70 | JAB0481 VHCDR3; nucleic acid | TATACTTCCGATTACTATACTATGGACTAC |
| 71 | JAB0481 VLCDR1; nucleic acid | CTGGCAAGTCAGACCATTGGTACATGGTTAGCA |
| 72 | JAB0481 VLCDR2; nucleic acid | GCTGCAACCAGCTTGGCAGAT |
| 73 | JAB0481 VLCDR3; nucleic acid | CAACAACTTTACAGTACTCCGTGGACG |
| 74 | JAB0481 VH; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAAATAT<br>GCCCCGAACTTCCAGGACAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCGATTACTATACT<br>ATGGACTACTGGGGTCAAGGAACCTCGGTCACCGTCTCCTCG |
| 75 | JAB0481 VL; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAAGTTATTACTGTCAACAA<br>CTTTACAGTACTCCGTGGACGTTCGGTGGAGGCACCAAGCTGGAA<br>ATCAAACG |
| 76 | JAB0481 HC; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAAATAT<br>GCCCCGAACTTCCAGGACAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCGATTACTATACT<br>ATGGACTACTGGGGTCAAGGAACCTCGGTCACCGTCTCCTCGGCT<br>AAAACGACACCCCCATCTGTCTATCCGCTAGCCCCTGGATCTGCT<br>GCCCAAACTAACTCCATGGTGACGCTGGGATGCCTGGTCAAGGGC<br>TATTTCCCTGAGCCAGTGACAGTGACCTGGAACTCTGGATCCCTG<br>TCCAGCGGTGTGCACACCTTCCCAGCTGTCCTGCAGTCTGACCTC<br>TACACTCTGAGCAGCTCAGTGACTGTCCCCTCCAGCACCTGGCCC<br>AGCCAGACCGTCACCTGCAACGTTGCCCACCCGGCCAGCAGCACC<br>AAGGTGGACAAGAAAATTGTGCCCAGGGATTGTGGTTGTAAGCCT<br>TGCATATGTACAGTCCCAGAAGTATCATCTGTCTTCATCTTCCCC<br>CCAAAGCCCAAGGATGTGCTCACCATTACTCTGACTCCTAAGGTC<br>ACGTGTGTTGTGGTAGACATCAGCAAGGATGATCCCGAGGTCCAG<br>TTCAGCTGGTTTGTAGATGATGTGGAGGTGCACACAGCTCAGACG<br>AAACCCCGGGAGGAGCAGATCAACAGCACTTTCCGTTCAGTCAGT<br>GAACTTCCCATCATGCACCAGGACTGGCTCAATGGCAAGGAGTTC<br>AAATGCAGGGTCAACAGTGCAGCTTTCCCTGCCCCCATCGAGAAA<br>ACCATCTCCAAAACCAAAGGCAGACCGAAGGCTCCACAGGTGTAC<br>ACCATTCCACCTCCCAAGGAGCAGATGGCCAAGGATAAAGTCAGT<br>CTGACCTGCATGATAACAAACTTCTTCCCTGAAGACATTACTGTG<br>GAGTGGCAGTGGAATGGGCAGCCAGCGGAGAACTACAAGAACACT<br>CAGCCCATCATGGACACAGATGGCTCTTACTTCGTCTACAGCAAG<br>CTCAATGTGCAGAAGAGCAACTGGGAGGCAGGAAATACTTTCACC<br>TGCTCTGTGTTACATGAGGGCCTGCACAACCACCATACTGAGAAG<br>AGCCTCTCCCACTCTCCTGGTAAATGA |

TABLE 6-continued

Summary of sequences

| SEQ ID | Description | Sequence |
|---|---|---|
| 77 | JAB0481 LC; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAAGTTATTACTGTCAACAA<br>CTTTACAGTACTCCGTGGACGTTCGGTGGAGGCACCAAGCTGGAA<br>ATCAAACGGGCTGATGCTGCACCAACTGTATCCATCTTCCCACCA<br>TCCAGTGAGCAGTTAACATCCGGAGGTGCCTCAGTCGTGTGCTTC<br>TTGAACAACTTCTACCCCAAAGACATCAATGTCAAGTGGAAGATT<br>GATGGCAGTGAACGACAAAATGGCGTCCTGAACAGTTGGACTGAT<br>CAGGACAGCAAAGACAGCACCTACAGCATGAGCAGCACCCTCACG<br>TTGACCAAGGACGAGTATGAACGACATAACAGCTATACCTGTGAG<br>GCCACTCACAAGACATCAACTTCACCCATTGTCAAGAGCTTCAAC<br>AGGAATGAGTGTTAA |
| 78 | JAB0501 VHCDR1; nucleic acid | GGCTTCAACATTAAAGACAGCCTTATGCAC |
| 79 | JAB0501 VHCDR2; nucleic acid | ATTGATCCTGAGGATGGTGAAACTAAATATGCCCCGAACTTCCAG<br>TCT |
| 80 | JAB0501 VHCDR3; nucleic acid | TATACTTCCCCGTACTATACTATGGACTAC |
| 81 | JAB0501 VLCDR1; nucleic acid | CTGGCAAGTCAGACCATTGGTACATGGTTAGCA |
| 82 | JAB0501 VLCDR2; nucleic acid | GCTGCAACCAGCTTGGCAGAT |
| 83 | JAB0501 VLCDR3; nucleic acid | CAACAAGTGTACAGTACTCCGTGGACGTT |
| 84 | JAB0501 VH; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAAATAT<br>GCCCCGAACTTCCAGTCTAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCCCGTACTATACT<br>ATGGACTACTGGGGTCAAGGAACCTCGGTCACCGTCTCCTCG |
| 85 | JAB0501 VL; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAAGTTATTACTGTCAACAA<br>GTGTACAGTACTCCGTGGACGTTCGGTGGAGGCACCAAGCTGGAA<br>ATCAAACG |
| 86 | JAB0501 HC; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAAATAT<br>GCCCCGAACTTCCAGTCTAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCCCGTACTATACT<br>ATGGACTACTGGGGTCAAGGAACCTCGGTCACCGTCTCCTCGGCT<br>AAAACGACACCCCCATCTGTCTATCCGTAGCCCCTGGATCTGCT<br>GCCCAAACTAACTCCATGGTGACGCTGGGATGCCTGGTCAAGGGC<br>TATTTCCCTGAGCCAGTGACAGTGACCTGGAACTCTGGATCCCTG<br>TCCAGCGGTGTGCACACCTTCCCAGCTGTCCTGCAGTCTGACCTC<br>TACACTCTGAGCAGCTCAGTGACTGTCCCCTCCAGCACCTGGCCC<br>AGCCAGACCGTCACCTGCAACGTTGCCCACCCGGCCAGCAGCACC<br>AAGGTGGACAAGAAAATTGTGCCCAGGGATTGTGGTTGTAAGCCT<br>TGCATATGTACAGTCCCAGAAGTATCATCTGTCTTCATCTTCCCC<br>CCAAAGCCCAAGGATGTGCTCACCATTACTCTGACTCCTAAGGTC<br>ACGTGTGTTGTGGTAGACATCAGCAAGGATGATCCCGAGGTCCAG<br>TTCAGCTGGTTTGTAGATGATGTGGAGGTGCACACAGCTCAGACG<br>AAACCCCGGGAGGAGCAGATCAACAGCACTTTCCGTTCAGTCAGT<br>GAACTTCCCATCATGCACCAGGACTGGCTCAATGGCAAGGAGTTC<br>AAATGCAGGGTCAACAGTGCAGCTTTCCCTGCCCCCATCGAGAAA<br>ACCATCTCCAAAACCAAAGGCAGACCGAAGGCTCCACAGGTGTAC |

TABLE 6-continued

Summary of sequences

| SEQ ID | Description | Sequence |
|---|---|---|
| | | ACCATTCCACCTCCCAAGGAGCAGATGGCCAAGGATAAAGTCAGT<br>CTGACCTGCATGATAACAAACTTCTTCCCTGAAGACATTACTGTG<br>GAGTGGCAGTGGAATGGGCAGCCAGCGGAGAACTACAAGAACACT<br>CAGCCCATCATGGACACAGATGGCTCTTACTTCGTCTACAGCAAG<br>CTCAATGTGCAGAAGAGCAACTGGGAGGCAGGAAATACTTTCACC<br>TGCTCTGTGTTACATGAGGGCCTGCACAACCACCATACTGAGAAG<br>AGCCTCTCCCACTCTCCTGGTAAATGA |
| 87 | JAB0501 LC; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAGTTATTACTGTCAACAA<br>GTGTACAGTACTCCGTGGACGTTCGGTGGAGGCACCAAGCTGGAA<br>ATCAAACGGGCTGATGCTGCACCAACTGTATCCATCTTCCCACCA<br>TCCAGTGAGCAGTTAACATCCGGAGGTGCCTCAGTCGTGTGCTTC<br>TTGAACAACTTCTACCCCAAAGACATCAATGTCAAGTGGAAGATT<br>GATGGCAGTGAACGACAAAATGGCGTCCTGAACAGTTGGACTGAT<br>CAGGACAGCAAAGACAGCACCTACAGCATGAGCAGCACCCTCACG<br>TTGACCAAGGACGAGTATGAACGACATAACAGCTATACCTGTGAG<br>GCCACTCACAAGACATCAACTTCACCCATTGTCAAGAGCTTCAAC<br>AGGAATGAGTGTTAA |
| 88 | JAB0505 VHCDR1; nucleic acid | GGCTTCAACATTAAAGACAGCCTTATGCAC |
| 89 | JAB0505 VHCDR2; nucleic acid | ATTGATCCTGAGGATGGTGAAACTAGGTATGCCCCGAACTTCCAG<br>GAC |
| 90 | JAB0505 VHCDR3; nucleic acid | TATACTTCCAGGTACTATACTATGGAGTAC |
| 91 | JAB0505 VLCDR1; nucleic acid | CTGGCAAGTCAGACCATTGGTACATGGTTAGCA |
| 92 | JAB0505 VLCDR2; nucleic acid | GCTGCAACCAGCTTGGCAGAT |
| 93 | JAB0505 VLCDR3; nucleic acid | CAACAACTTTACTGGACTCCGTGGAC |
| 94 | JAB0505 VH; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAGGTAT<br>GCCCCGAACTTCCAGGACAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCAGGTACTATACT<br>ATGGAGTACTGGGGTCAAGGAACCTCGGTCACCGTCTCCTCG |
| 95 | JAB0505 VL; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAGTTATTACTGTCAACAA<br>CTTTACTGGACTCCGTGGACGTTCGGTGGAGGCACCAAGCTGGAA<br>ATCAAACG |
| 96 | JAB0505 HC; nucleic acid | GAGGTCCAACTGCAACAGTCTGGGGCAGAGCTTGTGAGGCCAGGG<br>GCCTCAGTCAGGTTGTCCTGCACAGCTTCTGGCTTCAACATTAAA<br>GACAGCCTTATGCACTGGGTGAAGCAGAGGCCTGAACAGGGCCTG<br>GAGTGGATTGGATGGATTGATCCTGAGGATGGTGAAACTAGGTAT<br>GCCCCGAACTTCCAGGACAAGGCCACTATAACTGCAGTCACATCC<br>TCCAACACAGCCTACCTGCAGCTCAGCAGCCTGACATCTGAGGAC<br>TCTGCCATCTATTACTGTGCTAGGTATACTTCCAGGTACTATACT<br>ATGGAGTACTGGGGTCAAGGAACCTCGGTCACCGTCTCCTCGGCT<br>AAAACGACACCCCCATCTGTCTATCCGCTAGCCCCTGGATCTGCT<br>GCCCAAACTAACTCCATGGTGACCCTGGGATGCCTGGTCAAGGGC<br>TATTTCCCTGAGCCAGTGACAGTGACCTGGAACTCTGGATCCCTG<br>TCCAGCGGTGTGCACACCTTCCCAGCTGTCCTGCAGTCTGACCTC<br>TACACTCTGAGCAGCTCAGTGACTGTCCCCTCCAGCACCTGGCCC<br>AGCCAGACCGTCACCTGCAACGTTGCCCACCCGGCCAGCAGCACC<br>AAGGTGGACAAGAAAATTGTGCCCAGGGATTGTGGTTGTAAGCCT |

TABLE 6-continued

Summary of sequences

| SEQ ID | Description | Sequence |
|---|---|---|
| | | TGCATATGTACAGTCCCAGAAGTATCATCTGTCTTCATCTTCCCC<br>CCAAAGCCCAAGGATGTGCTCACCATTACTCTGACTCCTAAGGTC<br>ACGTGTGTTGTGGTAGACATCAGCAAGGATGATCCCGAGGTCCAG<br>TTCAGCTGGTTTGTAGATGATGTGGAGGTGCACACAGCTCAGACG<br>AAACCCCGGGAGGAGCAGATCAACAGCACTTTCCGTTCAGTCAGT<br>GAACTTCCCATCATGCACCAGGACTGGCTCAATGGCAAGGAGTTC<br>AAATGCAGGGTCAACAGTGCAGCTTTCCCTGCCCCCATCGAGAAA<br>ACCATCTCCAAAACCAAAGGCAGACCGAAGGCTCCACAGGTGTAC<br>ACCATTCCACCTCCCAAGGAGCAGATGGCCAAGGATAAAGTCAGT<br>CTGACCTGCATGATAACAAACTTCTTCCCTGAAGACATTACTGTG<br>GAGTGGCAGTGGAATGGGCAGCCAGCGGAGAACTACAAGAACACT<br>CAGCCCATCATGGACACAGATGGCTCTTACTTCGTCTACAGCAAG<br>CTCAATGTGCAGAAGAGCAACTGGGAGGCAGGAAATACTTTCACC<br>TGCTCTGTGTTACATGAGGGCCTGCACAACCACCATACTGAGAAG<br>AGCCTCTCCCACTCTCCTGGTAAATGA |
| 97 | JAB0505 LC; nucleic acid | GACATCCAGATGACCCAGTCTCCTGCCTCCCAGTCTGCATCTCTG<br>GGAGAAAGTGTCACCTTCACATGCCTGGCAAGTCAGACCATTGGT<br>ACATGGTTAGCATGGTATCAGCAGAAACCAGGGAAATCTCCTCAG<br>CTCCTGATTTATGCTGCAACCAGCTTGGCAGATGGGGTCCCATCA<br>AGGTTCAGTGGTAGTGGATCTGGCACAAAGTTTTCTTTCAAGATC<br>AGCAGCCTACAGGCTGAAGATTTTGCAAGTTATTACTGTCAACAA<br>CTTTACTGGACTCCGTGGACGTTCGGTGGAGGCACCAAGCTGGAA<br>ATCAAACGGGCTGATGCTGCACCAACTGTATCCATCTTCCCACCA<br>TCCAGTGAGCAGTTAACATCCGGAGGTGCCTCAGTCGTGTGCTTC<br>TTGAACAACTTCTACCCCAAAGACATCAATGTCAAGTGGAAGATT<br>GATGGCAGTGAACGACAAAATGGCGTCCTGAACAGTTGGACTGAT<br>CAGGACAGCAAAGACAGCACCTACAGCATGAGCAGCACCCTCACG<br>TTGACCAAGGACGAGTATGAACGACATAACAGCTATACCTGTGAG<br>GCCACTCACAAGACATCAACTTCACCCATTGTCAAGAGCTTCAAC<br>AGGAATGAGTGTTAA |
| 98 | pDMC074 | MEDEKPKVNPKLYMCVCEGLSCGNEDHCEGQQCFSSLSINDGFHV<br>YQKGCFQVYEQGKMTCKTPPSPGQAVECCQGDWCNRNITAQLPTK<br>GKSFPGTQNFHLE |
| 99 | pDMC094 | MVDGVMILPVLIMIALPSPSMEDEKPKVNPKLYMCVCEGLSCGNE<br>DHCEGQQCFSSLSINDGFHVYQKGCFQVYEQGKMTCKTPPSPGQA<br>VECCQGDWCNRNITAQLPTKGKSFPGTQNFHLE |
| 100 | pDMC075 | MVDGVMILPVLIMIALPSPSMEDEKPKVNPKLYMCVCEGLSCGNE<br>DHCEGQQCFSSLSINDGFHVYQKGCFQVYEQGKMTCKTPPSPGQA<br>VECCQGDWCNRNITAQLPTKGKSFPGTQNFHLE |
| 101 | pDMC076 | MEDEKPKVNPKLYMCVCEGLSCGNEDHCEGQQCFSSLSINDGFHV<br>YQKGCFQVYEQGKMTCKTPPSPGQAVECCQGDWCNRNITAQLPTK<br>GKSFPGTQNFHLE |
| 102 | pDMC099 | MVDGVMILPVLIMIALPSPSMSPILGYWKIKGLVQPTRLLLEYLE<br>EKYEEHLYERDEGDKWRNKKFELGLEFPNLPYYIDGDVKLTQSMA<br>IIRYIADKHNMLGGCPKERAEISMLEGAVLDIRYGVSRIAYSKDF<br>ETLKVDFLSKLPEMLKMFEDRLCHKTYLNGDHVTHPDFMLYDALD<br>VVLYMDPMCLDAFPKLVCFKKRIEAIPQIDKYLKSSKYIAWPLQG<br>WQATFGGGDHPPKSDGGSGMEDEKPKVNPKLYMCVCEGLSCGNED<br>HCEGQQCFSSLSINDGFHVYQKGCFQVYEQGKMTCKTPPSPGQAV<br>ECCQGDWCNRNITAQLPTKGKSFPGTQNFHLE |
| 103 | pDMC100 | MSPILGYWKIKGLVQPTRLLLEYLEEKYEEHLYERDEGDKWRNKK<br>FELGLEFPNLPYYIDGDVKLTQSMAIIRYIADKHNMLGGCPKERA<br>EISMLEGAVLDIRYGVSRIAYSKDFETLKVDFLSKLPEMLKMFED<br>RLCHKTYLNGDHVTHPDFMLYDALDVVLYMDPMCLDAFPKLVCFK<br>KRIEAIPQIDKYLKSSKYIAWPLQGWQATFGGGDHPPKSDGGSGM<br>EDEKPKVNPKLYMCVCEGLSCGNEDHCEGQQCFSSLSINDGFHVY<br>QKGCFQVYEQGKMTCKTPPSPGQAVECCQGDWCNRNITAQLPTKG<br>KSFPGTQNFHLE |

TABLE 6-continued

Summary of sequences

| SEQ ID | Description | Sequence |
|---|---|---|
| 104 | pDMC068 | MVDGVMILPVLIMIALPSPSMEDEKPKVNPKLYMCVCEGLSCGNE DHCEGQQCFSSLSINDGFHVYQKGCFQVYEQGKMTCKTPPSPGQA VECCQGDWCNRNITAQLPTKGKSFPGTQNFHLEVGLIILSVVFAV CLLACLLGVAL |

EQUIVALENTS

Those skilled in the art will recognize, or be able to ascertain using no more than routine experimentation, many equivalents of the specific embodiments disclosed herein. Such equivalents are intended to be encompassed by the following claims.

We claim:
1. An isolated antibody which binds to activin receptor-like kinase 2 (ALK2), comprising:
   (a) heavy chain CDR1, CDR2, and CDR3 sequences comprising SEQ ID NOs: 10, 11, and 12, respectively, and light chain CDR1, CDR2, and CDR3 sequences comprising SEQ ID NOs: 13, 14, and 15, respectively;
   (b) heavy chain CDR1, CDR2, and CDR3 sequences comprising SEQ ID NOs: 20, 21, and 22, respectively, and light chain CDR1, CDR2, and CDR3 sequences comprising SEQ ID NOs: 23, 24, and 25, respectively;
   (c) heavy chain CDR1, CDR2, and CDR3 sequences comprising SEQ ID NOs: 30, 31, and 32, respectively, and light chain CDR1, CDR2, and CDR3 sequences comprising SEQ ID NOs: 33, 34, and 35, respectively; or
   (d) heavy chain CDR1, CDR2, and CDR3 sequences comprising SEQ ID NOs: 40, 41, and 42, respectively, and light chain CDR1, CDR2, and CDR3 sequences comprising SEQ ID NOs: 43, 44, and 45, respectively.

2. The isolated antibody of claim 1, which binds to activin receptor-like kinase 2 (ALK2) and comprises heavy and light chain variable regions which are at least 90% identical to the amino acid sequences selected from the group consisting of:
   (a) SEQ ID NOs: 16 and 17, respectively;
   (b) SEQ ID NOs: 26 and 27, respectively;
   (c) SEQ ID NOs: 36 and 37, respectively; and
   (d) SEQ ID NOs: 46 and 47, respectively.

3. The isolated antibody of claim 1, which binds to activin receptor-like kinase 2 (ALK2) and comprises heavy and light chain variable region sequences which are at least 80% identical to the amino acid sequences selected from the group consisting of:
   (a) SEQ ID NOs: 16 and 17, respectively;
   (b) SEQ ID NOs: 26 and 27, respectively;
   (c) SEQ ID NOs: 36 and 37, respectively; and
   (d) SEQ ID NOs: 46 and 47, respectively.

4. The isolated monoclonal antibody of claim 1, or antigen binding portion thereof, which binds to activin receptor-like kinase 2 (ALK2) and comprises heavy chain and light chain sequences which are at least 80% identical to the amino acid sequences selected from the group consisting of:
   (a) SEQ ID NOs: 18 and 19, respectively;
   (b) SEQ ID NOs: 28 and 29, respectively;
   (c) SEQ ID NOs: 38 and 39, respectively; and
   (d) SEQ ID NOs: 48 and 49, respectively.

5. The antibody of claim 1, wherein the antibody:
   (a) is selected from the group consisting of an IgG1, an IgG2, an IgG3, an IgG4 and variants thereof;
   (b) comprises an effectorless Fc region;
   (c) comprises an effectorless Fc region, wherein the Fc region is an IgG2/IgG4 hybrid Fc region;
   (d) is a full length antibody;
   (e) is an antigen-binding fragment;
   (f) is a chimeric, human, or humanized antibody; or
   (g) has a second binding specificity.

6. An immunoconjugate comprising the antibody of claim 1 linked to an agent.

7. A composition comprising the antibody of claim 1 and a carrier.

8. A kit comprising the antibody of claim 1.

9. The isolated antibody of claim 1, which comprises heavy chain CDR1, CDR2, and CDR3 sequences comprising SEQ ID NOs: 10, 11, and 12, respectively, and light chain CDR1, CDR2, and CDR3 sequences comprising SEQ ID NOs: 13, 14, and 15, respectively.

10. The isolated antibody of claim 1, which comprises heavy chain CDR1, CDR2, and CDR3 sequences comprising SEQ ID NOs: 20, 21, and 22, respectively, and light chain CDR1, CDR2, and CDR3 sequences comprising SEQ ID NOs: 23, 24, and 25, respectively.

11. The isolated antibody of claim 1, which comprises heavy chain CDR1, CDR2, and CDR3 sequences comprising SEQ ID NOs: 30, 31, and 32, respectively, and light chain CDR1, CDR2, and CDR3 sequences comprising SEQ ID NOs: 33, 34, and 35, respectively.

12. The isolated antibody of claim 1, which comprises heavy chain CDR1, CDR2, and CDR3 sequences comprising SEQ ID NOs: 40, 41, and 42, respectively, and light chain CDR1, CDR2, and CDR3 sequences comprising SEQ ID NOs: 43, 44, and 45, respectively.

13. The isolated antibody of claim 1 or an antigen binding portion thereof, which binds to activin receptor-like kinase 2 (ALK2) and comprises heavy and light chain variable regions selected from the group consisting of:
   (a) SEQ ID NOs: 16 and 17, respectively;
   (b) SEQ ID NOs: 26 and 27, respectively;
   (c) SEQ ID NOs: 36 and 37, respectively; and
   (d) SEQ ID NOs: 46 and 47, respectively.

14. An immunoconjugate comprising the isolated antibody or antigen binding portion of claim 13 linked to an agent.

15. A composition comprising the isolated antibody or antigen binding portion of claim 13 and a carrier.

16. A kit comprising the isolated antibody or antigen binding portion of claim 13.

17. The isolated monoclonal antibody of claim 1, or antigen binding portion thereof, which binds to activin receptor-like kinase 2 (ALK2) and comprises heavy chain and light chain sequences which are at least 90% identical to the amino acid sequences selected from the group consisting of:
   (a) SEQ ID NOs: 18 and 19, respectively;
   (b) SEQ ID NOs: 28 and 29, respectively;
   (c) SEQ ID NOs: 38 and 39, respectively; and
   (d) SEQ ID NOs: 48 and 49, respectively.

18. The isolated antibody of claim 1 or an antigen binding portion thereof, which binds to activin receptor-like kinase 2 (ALK2) and comprises heavy and light chain variable regions selected from the group consisting of:
   (a) SEQ ID NOs: 18 and 19, respectively;
   (b) SEQ ID NOs: 28 and 29, respectively;
   (c) SEQ ID NOs: 38 and 39, respectively; and
   (d) SEQ ID NOs: 48 and 49, respectively.

* * * * *

SEQUENCE LISTING

<160> NUMBER OF SEQ ID NOS: 104

<210> SEQ ID NO 1
<211> LENGTH: 509
<212> TYPE: PRT
<213> ORGANISM: Mus musculus
<220> FEATURE:
<221> NAME/KEY: misc_feature
<222> LOCATION: (1)..(509)
<223> OTHER INFORMATION: Mouse ALK2, signal peptide

<400> SEQUENCE: 1

Met Val Asp Gly Val Met Ile Leu Pro Val Leu Met Met Met Ala Phe
1               5                   10                  15

Pro Ser Pro Ser Val Glu Asp Glu Lys Pro Lys Val Asn Gln Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Ile Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Glu Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

-continued

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Ser Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 2
<211> LENGTH: 509
<212> TYPE: PRT
<213> ORGANISM: Homo sapiens
<220> FEATURE:
<221> NAME/KEY: misc_feature
<222> LOCATION: (1)..(509)
<223> OTHER INFORMATION: Human ALK2; signal peptide

<400> SEQUENCE: 2

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

```
Val Tyr Gln Lys Gly Cys Phe Gln Val Tyr Glu Gln Gly Lys Met Thr
 65                  70                  75                  80

Cys Lys Thr Pro Pro Ser Pro Gly Gln Ala Val Glu Cys Cys Gln Gly
             85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
```

```
                    485                 490                 495
Lys Ile Asp Asn Ser Leu Asp Lys Leu Lys Thr Asp Cys
                500                 505

<210> SEQ ID NO 3
<211> LENGTH: 103
<212> TYPE: PRT
<213> ORGANISM: Homo sapiens
<220> FEATURE:
<221> NAME/KEY: misc_feature
<222> LOCATION: (1)..(103)
<223> OTHER INFORMATION: Human ALK2 extracellular domain

<400> SEQUENCE: 3

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu
            100

<210> SEQ ID NO 4
<211> LENGTH: 123
<212> TYPE: PRT
<213> ORGANISM: Homo sapiens
<220> FEATURE:
<221> NAME/KEY: misc_feature
<222> LOCATION: (1)..(123)
<223> OTHER INFORMATION: Human ALK2 ECD with signal peptide

<400> SEQUENCE: 4

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu
        115                 120

<210> SEQ ID NO 5
<211> LENGTH: 347
<212> TYPE: PRT
<213> ORGANISM: Homo sapiens
```

<220> FEATURE:
<221> NAME/KEY: misc_feature
<222> LOCATION: (1)..(347)
<223> OTHER INFORMATION: Human ALK2 ECD with signal peptide and N-term.
      GST tag

<400> SEQUENCE: 5

Met Val Asp Gly Val Met Ile Leu Pro Val Leu Ile Met Ile Ala Leu
1               5                   10                  15

Pro Ser Pro Ser Met Ser Pro Ile Leu Gly Tyr Trp Lys Ile Lys Gly
            20                  25                  30

Leu Val Gln Pro Thr Arg Leu Leu Leu Glu Tyr Leu Glu Glu Lys Tyr
        35                  40                  45

Glu Glu His Leu Tyr Glu Arg Asp Glu Gly Asp Lys Trp Arg Asn Lys
    50                  55                  60

Lys Phe Glu Leu Gly Leu Glu Phe Pro Asn Leu Pro Tyr Tyr Ile Asp
65                  70                  75                  80

Gly Asp Val Lys Leu Thr Gln Ser Met Ala Ile Ile Arg Tyr Ile Ala
                85                  90                  95

Asp Lys His Asn Met Leu Gly Gly Cys Pro Lys Glu Arg Ala Glu Ile
            100                 105                 110

Ser Met Leu Glu Gly Ala Val Leu Asp Ile Arg Tyr Gly Val Ser Arg
        115                 120                 125

Ile Ala Tyr Ser Lys Asp Phe Glu Thr Leu Lys Val Asp Phe Leu Ser
130                 135                 140

Lys Leu Pro Glu Met Leu Lys Met Phe Glu Asp Arg Leu Cys His Lys
145                 150                 155                 160

Thr Tyr Leu Asn Gly Asp His Val Thr His Pro Asp Phe Met Leu Tyr
                165                 170                 175

Asp Ala Leu Asp Val Val Leu Tyr Met Asp Pro Met Cys Leu Asp Ala
            180                 185                 190

Phe Pro Lys Leu Val Cys Phe Lys Lys Arg Ile Glu Ala Ile Pro Gln
        195                 200                 205

Ile Asp Lys Tyr Leu Lys Ser Ser Lys Tyr Ile Ala Trp Pro Leu Gln
210                 215                 220

Gly Trp Gln Ala Thr Phe Gly Gly Gly Asp His Pro Pro Lys Ser Asp
225                 230                 235                 240

Gly Gly Ser Gly Met Glu Asp Glu Lys Pro Lys Val Asn Pro Lys Leu
                245                 250                 255

Tyr Met Cys Val Cys Glu Gly Leu Ser Cys Gly Asn Glu Asp His Cys
            260                 265                 270

Glu Gly Gln Gln Cys Phe Ser Ser Leu Ser Ile Asn Asp Gly Phe His
        275                 280                 285

Val Tyr Gln Lys Gly Cys Phe Gln Val Tyr Glu Gln Gly Lys Met Thr
290                 295                 300

Cys Lys Thr Pro Pro Ser Pro Gly Gln Ala Val Glu Cys Cys Gln Gly
305                 310                 315                 320

Asp Trp Cys Asn Arg Asn Ile Thr Ala Gln Leu Pro Thr Lys Gly Lys
                325                 330                 335

Ser Phe Pro Gly Thr Gln Asn Phe His Leu Glu
            340                 345

<210> SEQ ID NO 6
<211> LENGTH: 329
<212> TYPE: PRT
<213> ORGANISM: Homo sapiens
<220> FEATURE:
<221> NAME/KEY: misc_feature
<222> LOCATION: (1)..(329)
<223> OTHER INFORMATION: Human ALK2 ECD with N-term. GST tag

<400> SEQUENCE: 6

Met Val Met Ser Pro Ile Leu Gly Tyr Trp Lys Ile Lys Gly Leu Val
1               5                   10                  15

Gln Pro Thr Arg Leu Leu Leu Glu Tyr Leu Glu Glu Lys Tyr Glu Glu
            20                  25                  30

His Leu Tyr Glu Arg Asp Glu Gly Asp Lys Trp Arg Asn Lys Lys Phe
        35                  40                  45

Glu Leu Gly Leu Glu Phe Pro Asn Leu Pro Tyr Tyr Ile Asp Gly Asp
    50                  55                  60

Val Lys Leu Thr Gln Ser Met Ala Ile Ile Arg Tyr Ile Ala Asp Lys
65                  70                  75                  80

His Asn Met Leu Gly Gly Cys Pro Lys Glu Arg Ala Glu Ile Ser Met
                85                  90                  95

Leu Glu Gly Ala Val Leu Asp Ile Arg Tyr Gly Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                165                 170                 175

Lys Leu Val Cys Phe Lys Lys Arg Ile Glu Ala Ile Pro Gln Ile Asp
            180                 185                 190

Lys Tyr Leu Lys Ser Ser Lys Tyr Ile Ala Trp Pro Leu Gln Gly Trp
        195                 200                 205

Gln Ala Thr Phe Gly Gly Gly Asp His Pro Pro Lys Ser Asp Gly Gly
    210                 215                 220

Ser Gly Met Glu Asp Glu Lys Pro Lys Val Asn Pro Lys Leu Tyr Met
225                 230                 235                 240

Cys Val Cys Glu Gly Leu Ser Cys Gly Asn Glu Asp His Cys Glu Gly
                245                 250                 255

Gln Gln Cys Phe Ser Ser Leu Ser Ile Asn Asp Gly Phe His Val Tyr
            260                 265                 270

Gln Lys Gly Cys Phe Gln Val Tyr Glu Gln Gly Lys Met Thr Cys Lys
        275                 280                 285

Thr Pro Pro Ser Pro Gly Gln Ala Val Glu Cys Cys Gln Gly Asp Trp
    290                 295                 300

Cys Asn Arg Asn Ile Thr Ala Gln Leu Pro Thr Lys Gly Lys Ser Phe
305                 310                 315                 320

Pro Gly Thr Gln Asn Phe His Leu Glu
            325

<210> SEQ ID NO 7
<211> LENGTH: 126
<212> TYPE: PRT
<213> ORGANISM: Homo sapiens
<220> FEATURE:
<221> NAME/KEY: misc_feature
<222> LOCATION: (1)..(126)
<223> OTHER INFORMATION: Human ALK2 ECD with C-terminal transmembrane domain

<400> SEQUENCE: 7

```
Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Val Gly Leu Ile Ile Leu Ser Val Val
            100                 105                 110

Phe Ala Val Cys Leu Leu Ala Cys Leu Leu Gly Val Ala Leu
        115                 120                 125
```

<210> SEQ ID NO 8
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 heavy chain constant region

<400> SEQUENCE: 8

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 326
<212> TYPE: PRT
<213> ORGANISM: Artificial Sequence
<220> FEATURE:
<223> OTHER INFORMATION: Synthetic: IgG2/4 hybrid Fc

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240
```

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 10
<211> LENGTH: 10
<212> TYPE: PRT
<213> ORGANISM: Artificial Sequence
<220> FEATURE:
<223> OTHER INFORMATION: Synthetic: JAB0399 VHCDR1

<400> SEQUENCE: 10

Gly Phe Asn Ile Lys Asp Ser Leu Met His
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic: JAB0399 VHCDR2

<400> SEQUENCE: 11

Ile Asp Pro Glu Asp Gly Glu Thr Lys Tyr Ala Pro Asn Phe Gln Asp
1               5                   10                  15

<210> SEQ ID NO 12
<211> LENGTH: 10
<212> TYPE: PRT
<213> ORGANISM: Artificial Sequence
<220> FEATURE:
<223> OTHER INFORMATION: Synthetic: JAB0399 VHCDR3

<400> SEQUENCE: 12

Tyr Thr Ser Asp Tyr Tyr Thr Met Asp Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic: JAB0399 VLCDR1

<400> SEQUENCE: 13

Leu Ala Ser Gln Thr Ile Gly Thr Trp Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic: JAB0399 VLCDR2

<400> SEQUENCE: 14
```

Ala Ala Thr Ser Leu Ala Asp
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic: JAB0399 VLCDR3

<400> SEQUENCE: 15

Gln Gln Leu Tyr Ser Thr Pro Trp Thr
1               5

<210> SEQ ID NO 16
<211> LENGTH: 119
<212> TYPE: PRT
<213> ORGANISM: Artificial Sequence
<220> FEATURE:
<223> OTHER INFORMATION: Synthetic: JAB0399 VH

<400> SEQUENCE: 16

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Lys Tyr Ala Pro Asn Phe
    50                  55                  60

Gln Asp Lys Ala Thr Ile Thr Ala Val Thr Ser Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Asp Tyr Tyr Thr Met Asp Tyr Trp Gly Gln Gly
            100                 105                 110

Thr Ser Val Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: Synthetic: JAB0399 VL

<400> SEQUENCE: 17

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Leu Tyr Ser Thr Pro Trp
                85                  90                  95

```
Thr Phe Gly Gly Gly Thr Lys Leu Glu Ile Lys
                100                 105
```

```
<210> SEQ ID NO 18
<211> LENGTH: 443
<212> TYPE: PRT
<213> ORGANISM: Artificial Sequence
<220> FEATURE:
<223> OTHER INFORMATION: Synthetic: JAB0399 HC Constant region

<400> SEQUENCE: 18

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Lys Tyr Ala Pro Asn Phe
    50                  55                  60

Gln Asp Lys Ala Thr Ile Thr Ala Val Thr Ser Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Asp Tyr Tyr Thr Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Phe Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Gln Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Lys Pro Arg
        275                 280                 285

Glu Glu Gln Ile Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350
```

Gln Met Ala Lys Asp Lys Val Ser Leu Thr Cys Met Ile Thr Asn Phe
                355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440

<210> SEQ ID NO 19
<211> LENGTH: 214
<212> TYPE: PRT
<213> ORGANISM: Artificial Sequence
<220> FEATURE:
<223> OTHER INFORMATION: Synthetic: JAB0399 LC Constant region

<400> SEQUENCE: 19

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
                20                  25                  30

Leu Ala Trp Tyr Gln Gln Lys Pro Gly Lys Ser Pro Gln Leu Leu Ile
                35                  40                  45

Tyr Ala Ala Thr Ser Leu Ala Asp Gly Val Pro Ser Arg Phe Ser Gly
        50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Leu Tyr Ser Thr Pro Trp
                85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
        210

<210> SEQ ID NO 20
<211> LENGTH: 10
<212> TYPE: PRT
<213> ORGANISM: Artificial Sequence
<220> FEATURE:
<223> OTHER INFORMATION: Synthetic: JAB0481 VHCDR1

<400> SEQUENCE: 20

```
Gly Phe Asn Ile Lys Asp Ser Leu Met His
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Synthetic: JAB0481VHCDR2

<400> SEQUENCE: 21

Ile Asp Pro Glu Asp Gly Glu Thr Lys Tyr Ala Pro Asn Phe Gln Asp
1               5                   10                  15

<210> SEQ ID NO 22
<211> LENGTH: 10
<212> TYPE: PRT
<213> ORGANISM: Artificial Sequence
<220> FEATURE:
<223> OTHER INFORMATION: Synthetic: JAB0481VHCDR3

<400> SEQUENCE: 22

Tyr Thr Ser Asp Tyr Tyr Thr Met Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic: JAB0481VLCDR1

<400> SEQUENCE: 23

Leu Ala Ser Gln Thr Ile Gly Thr Trp Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Synthetic: JAB0481VLCDR2

<400> SEQUENCE: 24

Ala Ala Thr Ser Leu Ala Asp
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic: JAB0481VLCDR3

<400> SEQUENCE: 25

Gln Gln Leu Tyr Ser Thr Pro Trp Thr
1               5

<210> SEQ ID NO 26
<211> LENGTH: 119
<212> TYPE: PRT
<213> ORGANISM: Artificial Sequence
<220> FEATURE:
<223> OTHER INFORMATION: Synthetic: JAB0481 VH

<400> SEQUENCE: 26
```

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Lys Tyr Ala Pro Asn Phe
    50                  55                  60

Gln Asp Lys Ala Thr Ile Thr Ala Val Thr Ser Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Asp Tyr Tyr Thr Met Asp Tyr Trp Gly Gln Gly
                100                 105                 110

Thr Ser Val Thr Val Ser Ser
            115

<210> SEQ ID NO 27
<211> LENGTH: 107
<212> TYPE: PRT
<213> ORGANISM: Artificial Sequence
<220> FEATURE:
<223> OTHER INFORMATION: Synthetic: JAB0481 VL

<400> SEQUENCE: 27

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Leu Tyr Ser Thr Pro Trp
                85                  90                  95

Thr Phe Gly Gly Gly Thr Lys Leu Glu Ile Lys
                100                 105

<210> SEQ ID NO 28
<211> LENGTH: 443
<212> TYPE: PRT
<213> ORGANISM: Artificial Sequence
<220> FEATURE:
<223> OTHER INFORMATION: Synthetic: JAB0481 HC Constant region

<400> SEQUENCE: 28

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Lys Tyr Ala Pro Asn Phe
    50                  55                  60

Gln Asp Lys Ala Thr Ile Thr Ala Val Thr Ser Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Asp Tyr Thr Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Gln Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Lys Pro Arg
        275                 280                 285

Glu Glu Gln Ile Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asn Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 29
<211> LENGTH: 214
<212> TYPE: PRT
<213> ORGANISM: Artificial Sequence
<220> FEATURE:
<223> OTHER INFORMATION: Synthetic: JAB0481 LC Constant region

<400> SEQUENCE: 29

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Ala Trp Tyr Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Leu Tyr Ser Thr Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 30
<211> LENGTH: 10
<212> TYPE: PRT
<213> ORGANISM: Artificial Sequence
<220> FEATURE:
<223> OTHER INFORMATION: Synthetic: JAB0501 VHCDR1

<400> SEQUENCE: 30

Gly Phe Asn Ile Lys Asp Ser Leu Met His
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Synthetic: JAB0501 VHCDR2

<400> SEQUENCE: 31

Ile Asp Pro Glu Asp Gly Glu Thr Lys Tyr Ala Pro Asn Phe Gln Ser
1               5                   10                  15

<210> SEQ ID NO 32
<211> LENGTH: 10
<212> TYPE: PRT
<213> ORGANISM: Artificial Sequence
<220> FEATURE:
<223> OTHER INFORMATION: Synthetic: JAB0501 VHCDR3

<400> SEQUENCE: 32

```
Tyr Thr Ser Pro Tyr Tyr Thr Met Asp Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic: JAB0501 VLCDR1

<400> SEQUENCE: 33

Leu Ala Ser Gln Thr Ile Gly Thr Trp Leu Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic: JAB0501 VLCDR2

<400> SEQUENCE: 34

Ala Ala Thr Ser Leu Ala Asp
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic: JAB0501 VLCDR3

<400> SEQUENCE: 35

Gln Gln Val Tyr Ser Thr Pro Trp Thr
1               5

<210> SEQ ID NO 36
<211> LENGTH: 119
<212> TYPE: PRT
<213> ORGANISM: Artificial Sequence
<220> FEATURE:
<223> OTHER INFORMATION: Synthetic: JAB0501 VH

<400> SEQUENCE: 36

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Lys Tyr Ala Pro Asn Phe
    50                  55                  60

Gln Ser Lys Ala Thr Ile Thr Ala Val Thr Ser Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Pro Tyr Tyr Thr Met Asp Tyr Trp Gly Gln Gly
            100                 105                 110

Thr Ser Val Thr Val Ser Ser
        115

<210> SEQ ID NO 37
<211> LENGTH: 107
```

```
<212> TYPE: PRT
<213> ORGANISM: Artificial Sequence
<220> FEATURE:
<223> OTHER INFORMATION: Synthetic: JAB0501 VL

<400> SEQUENCE: 37
```

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Val Tyr Ser Thr Pro Trp
                85                  90                  95

Thr Phe Gly Gly Gly Thr Lys Leu Glu Ile Lys
            100                 105

```
<210> SEQ ID NO 38
<211> LENGTH: 443
<212> TYPE: PRT
<213> ORGANISM: Artificial Sequence
<220> FEATURE:
<223> OTHER INFORMATION: Synthetic: JAB0501 HC Constant region

<400> SEQUENCE: 38
```

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Lys Tyr Ala Pro Asn Phe
50                  55                  60

Gln Ser Lys Ala Thr Ile Thr Ala Val Thr Ser Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Pro Tyr Tyr Thr Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Gln Thr Val Thr Cys Asn Val Ala His Pro Ala Ser
        195                 200                 205

Ser Thr Lys Val Asp Lys Lys Ile Val Pro Arg Asp Cys Gly Cys Lys
210                 215                 220

```
Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Asp Ile Ser Lys Asp Asp Pro Glu Val Gln Phe Ser
                260                 265                 270

Trp Phe Val Asp Asp Val Glu Val His Thr Ala Gln Thr Lys Pro Arg
                275                 280                 285

Glu Glu Gln Ile Asn Ser Thr Phe Arg Ser Val Ser Glu Leu Pro Ile
                290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asn Phe
                355                 360                 365

Phe Pro Glu Asp Ile Thr Val Glu Trp Gln Trp Asn Gly Gln Pro Ala
                370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440

<210> SEQ ID NO 39
<211> LENGTH: 214
<212> TYPE: PRT
<213> ORGANISM: Artificial Sequence
<220> FEATURE:
<223> OTHER INFORMATION: Synthetic: JAB0501 LC Constant region

<400> SEQUENCE: 39

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
                20                  25                  30

Leu Ala Trp Tyr Gln Gln Lys Pro Gly Lys Ser Pro Gln Leu Leu Ile
                35                  40                  45

Tyr Ala Ala Thr Ser Leu Ala Asp Gly Val Pro Ser Arg Phe Ser Gly
            50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Val Tyr Ser Thr Pro Trp
                85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
130                 135                 140
```

```
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 40
<211> LENGTH: 10
<212> TYPE: PRT
<213> ORGANISM: Artificial Sequence
<220> FEATURE:
<223> OTHER INFORMATION: Synthetic: JAB0505 VHCDR1

<400> SEQUENCE: 40

Gly Phe Asn Ile Lys Asp Ser Leu Met His
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Synthetic: JAB0505 VHCDR2

<400> SEQUENCE: 41

Ile Asp Pro Glu Asp Gly Glu Thr Arg Tyr Ala Pro Asn Phe Gln Asp
1               5                   10                  15

<210> SEQ ID NO 42
<211> LENGTH: 10
<212> TYPE: PRT
<213> ORGANISM: Artificial Sequence
<220> FEATURE:
<223> OTHER INFORMATION: Synthetic: JAB0505 VHCDR3

<400> SEQUENCE: 42

Tyr Thr Ser Arg Tyr Tyr Thr Met Glu Tyr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic: JAB0505 VLCDR1

<400> SEQUENCE: 43

Leu Ala Ser Gln Thr Ile Gly Thr Trp Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic: JAB0505 VLCDR2

<400> SEQUENCE: 44

Ala Ala Thr Ser Leu Ala Asp
```

<210> SEQ ID NO 45
<211> LENGTH: 9
<212> TYPE: PRT
<213> ORGANISM: Artificial Sequence
<220> FEATURE:
<223> OTHER INFORMATION: Synthetic: JAB0505 VLCDR3

<400> SEQUENCE: 45

Gln Gln Leu Tyr Trp Thr Pro Trp Thr
1               5

<210> SEQ ID NO 46
<211> LENGTH: 119
<212> TYPE: PRT
<213> ORGANISM: Artificial Sequence
<220> FEATURE:
<223> OTHER INFORMATION: Synthetic: JAB0505 VH

<400> SEQUENCE: 46

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Arg Tyr Ala Pro Asn Phe
    50                  55                  60

Gln Asp Lys Ala Thr Ile Thr Ala Val Thr Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Arg Tyr Tyr Thr Met Glu Tyr Trp Gly Gln Gly
            100                 105                 110

Thr Ser Val Thr Val Ser Ser
        115

<210> SEQ ID NO 47
<211> LENGTH: 107
<212> TYPE: PRT
<213> ORGANISM: Artificial Sequence
<220> FEATURE:
<223> OTHER INFORMATION: Synthetic: JAB0505 VL

<400> SEQUENCE: 47

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Leu Tyr Trp Thr Pro Trp
                85                  90                  95

Thr Phe Gly Gly Gly Thr Lys Leu Glu Ile Lys
            100                 105

<210> SEQ ID NO 48
<211> LENGTH: 443
<212> TYPE: PRT
<213> ORGANISM: Artificial Sequence
<220> FEATURE:
<223> OTHER INFORMATION: Synthetic: JAB0505 HC Constant region

<400> SEQUENCE: 48

```
Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Arg Tyr Ala Pro Asn Phe
    50                  55                  60

Gln Asp Lys Ala Thr Ile Thr Ala Val Thr Ser Ser Asn Thr Ala Tyr
65                  70                  75                  80

Leu Gln Leu Ser Ser Leu Thr Ser Glu Asp Ser Ala Ile Tyr Tyr Cys
                85                  90                  95

Ala Arg Tyr Thr Ser Arg Tyr Tyr Thr Met Glu Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Gln Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Lys Pro Arg
        275                 280                 285

Glu Glu Gln Ile Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asn Phe
        355                 360                 365
```

```
Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440
```

```
<210> SEQ ID NO 49
<211> LENGTH: 214
<212> TYPE: PRT
<213> ORGANISM: Artificial Sequence
<220> FEATURE:
<223> OTHER INFORMATION: Synthetic: JAB0505 LC Constant region

<400> SEQUENCE: 49

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
                20                  25                  30

Leu Ala Trp Tyr Gln Gly Lys Pro Gly Lys Ser Pro Gln Leu Leu Ile
            35                  40                  45

Tyr Ala Ala Thr Ser Leu Ala Asp Gly Val Pro Ser Arg Phe Ser Gly
        50                  55                  60

Ser Gly Ser Gly Thr Lys Phe Ser Phe Lys Ile Ser Ser Leu Gln Ala
65                  70                  75                  80

Glu Asp Phe Ala Ser Tyr Tyr Cys Gln Gln Leu Tyr Trp Thr Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

```
<210> SEQ ID NO 50
<211> LENGTH: 19
<212> TYPE: PRT
<213> ORGANISM: Artificial Sequence
<220> FEATURE:
<223> OTHER INFORMATION: Synthetic: Signal sequence

<400> SEQUENCE: 50

Met Gly Trp Ser Cys Ile Ile Leu Phe Leu Val Ala Thr Ala Thr Gly
```

1       5          10           15

Val His Ser

<210> SEQ ID NO 51
<211> LENGTH: 310
<212> TYPE: PRT
<213> ORGANISM: Homo sapiens
<220> FEATURE:
<221> NAME/KEY: misc_feature
<222> LOCATION: (1)..(310)
<223> OTHER INFORMATION: Human ALK2 extracellular domain; nucleic acid

<400> SEQUENCE: 51

Ala Thr Gly Gly Ala Gly Ala Cys Gly Ala Ala Ala Gly Cys
1               5                   10                  15

Cys Thr Ala Ala Ala Gly Thr Gly Ala Ala Thr Cys Cys Ala Ala
                20                  25                  30

Ala Thr Thr Gly Thr Ala Thr Ala Gly Thr Gly Cys Gly Thr Cys
                35                  40                  45

Thr Gly Cys Gly Ala Ala Gly Gly Ala Cys Thr Gly Thr Cys Ala Thr
    50                  55                  60

Gly Thr Gly Gly Thr Ala Ala Thr Gly Ala Ala Gly Ala Thr Cys Ala
65                  70                  75                  80

Thr Thr Gly Cys Gly Ala Ala Gly Gly Cys Ala Ala Cys Ala Ala
                85                  90                  95

Thr Gly Cys Thr Thr Cys Ala Gly Cys Ala Gly Cys Thr Thr Gly Thr
                100                 105                 110

Cys Ala Ala Thr Cys Ala Ala Cys Gly Ala Cys Gly Gly Ala Thr Thr
                115                 120                 125

Thr Cys Ala Cys Gly Thr Gly Thr Ala Thr Cys Ala Ala Ala Ala
                130                 135                 140

Gly Gly Ala Thr Gly Thr Thr Thr Cys Ala Ala Gly Thr Gly Thr
145                 150                 155                 160

Ala Cys Gly Ala Ala Cys Ala Ala Gly Gly Thr Ala Ala Ala Thr
                165                 170                 175

Gly Ala Cys Thr Thr Gly Cys Ala Ala Ala Cys Gly Cys Cys Ala
                180                 185                 190

Cys Cys Thr Thr Cys Cys Cys Gly Gly Ala Cys Ala Ala Gly
                195                 200                 205

Cys Gly Gly Thr Cys Gly Ala Ala Thr Gly Thr Gly Thr Cys Ala
                210                 215                 220

Gly Gly Gly Cys Gly Ala Thr Thr Gly Thr Gly Thr Ala Ala Thr
225                 230                 235                 240

Cys Gly Cys Ala Ala Thr Ala Thr Cys Ala Cys Thr Gly Cys Ala Cys
                245                 250                 255

Ala Gly Cys Thr Cys Cys Cys Gly Ala Cys Cys Ala Gly Gly Gly
                260                 265                 270

Ala Ala Ala Gly Thr Cys Gly Thr Thr Thr Cys Cys Gly Gly Cys Cys
                275                 280                 285

Ala Cys Cys Cys Ala Ala Ala Thr Thr Thr Thr Cys Ala Thr Cys
                290                 295                 300

Thr Cys Gly Ala Gly Thr
305                 310

<210> SEQ ID NO 52
<211> LENGTH: 370

<212> TYPE: PRT
<213> ORGANISM: Homo sapiens
<220> FEATURE:
<221> NAME/KEY: misc_feature
<222> LOCATION: (1)..(370)
<223> OTHER INFORMATION: Human ALK2 ECD with signal peptide; nucleic acid

<400> SEQUENCE: 52

| Ala | Thr | Gly | Gly | Thr | Cys | Gly | Ala | Cys | Gly | Gly | Cys | Gly | Thr | Thr | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Gly | Ala | Thr | Cys | Cys | Thr | Gly | Cys | Cys | Gly | Gly | Thr | Gly | Cys | Thr |
|     |     |     | 20  |     |     |     |     | 25  |     |     |     |     | 30  |     |     |

| Thr | Ala | Thr | Cys | Ala | Thr | Gly | Ala | Thr | Cys | Gly | Cys | Cys | Cys | Thr | Cys |
|     |     | 35  |     |     |     |     | 40  |     |     |     |     | 45  |     |     |     |

| Cys | Cys | Ala | Thr | Cys | Gly | Cys | Cys | Gly | Thr | Cys | Cys | Ala | Thr | Gly | Gly |
| 50  |     |     |     |     | 55  |     |     |     |     | 60  |     |     |     |     |     |

| Ala | Gly | Gly | Ala | Cys | Gly | Ala | Ala | Ala | Gly | Cys | Cys | Thr | Ala | Ala |
| 65  |     |     |     |     | 70  |     |     |     |     | 75  |     |     |     | 80  |

| Ala | Gly | Thr | Gly | Ala | Ala | Thr | Cys | Cys | Ala | Ala | Ala | Thr | Thr | Gly |
|     |     |     |     |     |     | 85  |     |     |     |     | 90  |     |     |     | 95  |

| Thr | Ala | Thr | Ala | Thr | Gly | Thr | Gly | Cys | Gly | Thr | Cys | Thr | Gly | Cys | Gly |
|     |     |     |     | 100 |     |     |     |     | 105 |     |     |     |     | 110 |     |

| Ala | Ala | Gly | Gly | Ala | Cys | Thr | Gly | Thr | Cys | Ala | Thr | Gly | Thr | Gly | Gly |
|     |     |     | 115 |     |     |     |     | 120 |     |     |     |     | 125 |     |     |

| Thr | Ala | Ala | Thr | Gly | Ala | Ala | Gly | Ala | Thr | Cys |

Gly Thr
    370

<210> SEQ ID NO 53
<211> LENGTH: 1041
<212> TYPE: PRT
<213> ORGANISM: Homo sapiens
<220> FEATURE:
<221> NAME/KEY: misc_feature
<222> LOCATION: (1)..(1041)
<223> OTHER INFORMATION: Human ALK2 ECD with signal peptide and N-term.
      GST tag; nucleic acid

<400> SEQUENCE: 53

Ala Thr Gly Gly Thr Cys Gly Ala Cys Gly Cys Gly Thr Thr Ala
1               5                   10                  15

Thr Gly Ala Thr Cys Cys Thr Gly Cys Cys Gly Gly Thr Gly Cys Thr
            20                  25                  30

Thr Ala Thr Cys Ala Thr Gly Ala Thr Cys Gly Cys Cys Thr Cys
            35                  40                  45

Cys Cys Ala Thr Cys Gly Cys Cys Gly Thr Cys Cys Ala Thr Gly Thr
    50                  55                  60

Cys Cys Cys Cys Thr Ala Thr Ala Cys Thr Ala Gly Gly Thr Thr Ala
65                  70                  75                  80

Thr Thr Gly Gly Ala Ala Ala Thr Thr Ala Ala Gly Gly Gly Cys
            85                  90                  95

Cys Thr Thr Gly Thr Gly Cys Ala Ala Cys Cys Ala Cys Thr Cys
            100                 105                 110

Gly Ala Cys Thr Thr Cys Thr Thr Thr Gly Gly Ala Ala Thr Ala
            115                 120                 125

Thr Cys Thr Thr Gly Ala Ala Gly Ala Ala Ala Ala Thr Ala Thr
    130                 135                 140

Gly Ala Ala Gly Ala Gly Cys Ala Thr Thr Thr Gly Thr Ala Thr
145                 150                 155                 160

Ala Gly Cys Gly Cys Gly Ala Thr Gly Ala Ala Gly Gly Thr Gly Ala
            165                 170                 175

Thr Ala Ala Ala Thr Gly Gly Cys Gly Ala Ala Cys Ala Ala Ala
            180                 185                 190

Ala Ala Gly Thr Thr Thr Gly Ala Ala Thr Thr Gly Gly Gly Thr Thr
            195                 200                 205

Thr Gly Gly Ala Gly Thr Thr Thr Cys Cys Cys Ala Ala Thr Cys Thr
    210                 215                 220

Thr Cys Cys Thr Thr Ala Thr Thr Ala Thr Thr Gly Ala Thr
225                 230                 235                 240

Gly Gly Thr Gly Ala Thr Gly Thr Thr Ala Ala Thr Thr Ala Ala
            245                 250                 255

Cys Ala Cys Ala Gly Thr Cys Thr Ala Thr Gly Gly Cys Cys Ala Thr
            260                 265                 270

Cys Ala Thr Ala Cys Gly Thr Thr Ala Thr Thr Ala Gly Cys Thr
            275                 280                 285

Gly Ala Cys Ala Ala Gly Cys Ala Cys Ala Ala Thr Gly Thr
    290                 295                 300

Thr Gly Gly Gly Thr Gly Gly Thr Gly Thr Cys Cys Ala Ala Ala
305                 310                 315                 320

Ala Gly Ala Gly Cys Gly Thr Gly Cys Ala Gly Ala Thr Thr
            325                 330                 335

-continued

```
Thr Cys Ala Ala Thr Gly Cys Thr Thr Gly Ala Ala Gly Gly Ala Gly
            340                 345                 350

Cys Gly Gly Thr Thr Thr Thr Gly Gly Ala Thr Ala Thr Thr Ala Gly
        355                 360                 365

Ala Thr Ala Cys Gly Gly Thr Gly Thr Thr Thr Cys Gly Ala Gly Ala
    370                 375                 380

Ala Thr Thr Gly Cys Ala Thr Ala Thr Ala Gly Thr Ala Ala Ala Gly
385                 390                 395                 400

Ala Cys Thr Thr Thr Gly Ala Ala Ala Cys Thr Cys Thr Cys Ala Ala
                405                 410                 415

Ala Gly Thr Thr Gly Ala Thr Thr Thr Thr Cys Thr Thr Ala Gly Cys
            420                 425                 430

Ala Ala Gly Cys Thr Ala Cys Cys Thr Gly Ala Ala Ala Thr Gly Cys
        435                 440                 445

Thr Gly Ala Ala Ala Ala Thr Gly Thr Thr Cys Gly Ala Ala Gly Ala
    450                 455                 460

Thr Cys Gly Thr Thr Thr Ala Thr Gly Thr Cys Ala Thr Ala Ala Ala
465                 470                 475                 480

Ala Cys Ala Thr Ala Thr Thr Thr Ala Ala Ala Thr Gly Gly Thr Gly
                485                 490                 495

Ala Thr Cys Ala Thr Gly Thr Ala Ala Cys Cys Cys Ala Thr Cys Cys
            500                 505                 510

Thr Gly Ala Cys Thr Thr Cys Ala Thr Gly Thr Thr Gly Thr Ala Thr
        515                 520                 525

Gly Ala Cys Gly Cys Thr Cys Thr Thr Gly Ala Thr Gly Thr Thr Gly
    530                 535                 540

Thr Thr Thr Thr Ala Thr Ala Cys Ala Thr Gly Gly Ala Cys Cys Cys
545                 550                 555                 560

Ala Ala Thr Gly Thr Gly Cys Cys Thr Gly Gly Ala Thr Gly Cys Gly
                565                 570                 575

Thr Thr Cys Cys Cys Ala Ala Ala Ala Thr Thr Ala Gly Thr Thr Thr
            580                 585                 590

Gly Thr Thr Thr Thr Ala Ala Ala Ala Ala Ala Cys Gly Thr Ala Thr
        595                 600                 605

Thr Gly Ala Ala Gly Cys Thr Ala Thr Cys Cys Cys Ala Cys Ala Ala
    610                 615                 620

Ala Thr Thr Gly Ala Thr Ala Ala Gly Thr Ala Cys Thr Thr Gly Ala
625                 630                 635                 640

Ala Ala Thr Cys Cys Ala Gly Cys Ala Ala Gly Thr Ala Thr Ala Thr
                645                 650                 655

Ala Gly Cys Ala Thr Gly Gly Cys Cys Thr Thr Thr Gly Cys Ala Gly
            660                 665                 670

Gly Gly Cys Thr Gly Gly Cys Ala Ala Gly Cys Cys Ala Cys Gly Thr
        675                 680                 685

Thr Thr Gly Gly Thr Gly Gly Thr Gly Gly Cys Gly Ala Cys Cys Ala
    690                 695                 700

Thr Cys Cys Thr Cys Cys Ala Ala Ala Ala Thr Cys Gly Gly Ala Thr
705                 710                 715                 720

Gly Gly Cys Gly Gly Thr Ala Gly Cys Gly Gly Gly Ala Thr Gly Gly
                725                 730                 735

Ala Gly Gly Ala Cys Gly Ala Ala Ala Ala Gly Cys Cys Thr Ala Ala
            740                 745                 750

Ala Gly Thr Gly Ala Ala Thr Cys Cys Cys Ala Ala Ala Thr Thr Gly
```

```
                  755              760              765
Thr Ala Thr Ala Thr Gly Thr Gly Cys Gly Thr Cys Thr Gly Cys Gly
        770              775              780

Ala Ala Gly Gly Ala Cys Thr Gly Thr Cys Ala Thr Gly Thr Gly Gly
785              790              795              800

Thr Ala Ala Thr Gly Ala Ala Gly Ala Thr Cys Ala Thr Thr Gly Cys
            805              810              815

Gly Ala Ala Gly Gly Cys Ala Ala Cys Ala Ala Thr Gly Cys Thr
        820              825              830

Thr Cys Ala Gly Cys Ala Gly Cys Thr Thr Gly Thr Cys Ala Ala Thr
            835              840              845

Cys Ala Ala Cys Gly Ala Cys Gly Gly Ala Thr Thr Cys Ala Cys
        850              855              860

Gly Thr Gly Thr Ala Thr Cys Ala Ala Ala Ala Gly Gly Ala Thr
865              870              875              880

Gly Thr Thr Thr Cys Cys Ala Ala Gly Thr Gly Thr Ala Cys Gly Ala
                885              890              895

Ala Cys Ala Ala Gly Gly Thr Ala Ala Ala Thr Gly Ala Cys Thr
            900              905              910

Thr Gly Cys Ala Ala Ala Cys Gly Cys Ala Cys Cys Thr Thr
        915              920              925

Cys Cys Cys Cys Gly Gly Gly Ala Cys Ala Ala Gly Cys Gly Thr
        930              935              940

Cys Gly Ala Ala Thr Gly Thr Thr Gly Thr Cys Ala Gly Gly Gly Cys
945              950              955              960

Gly Ala Thr Thr Gly Gly Thr Gly Thr Ala Ala Thr Cys Gly Cys Ala
            965              970              975

Ala Thr Ala Thr Cys Ala Cys Thr Gly Cys Ala Cys Ala Gly Cys Thr
            980              985              990

Cys Cys Cys Gly Ala Cys Cys Ala  Ala Gly Gly Gly Ala  Ala Ala Gly
        995              1000              1005

Thr Cys  Gly Thr Thr Thr Cys  Gly Gly Gly Cys  Ala Cys Cys
    1010              1015              1020

Cys Ala  Ala Ala Ala Thr Thr  Thr Thr Cys Ala Thr  Cys Thr Cys
    1025              1030              1035

Gly Ala  Gly
    1040

<210> SEQ ID NO 54
<211> LENGTH: 987
<212> TYPE: PRT
<213> ORGANISM: Homo sapiens
<220> FEATURE:
<221> NAME/KEY: misc_feature
<222> LOCATION: (1)..(987)
<223> OTHER INFORMATION: Human ALK2 ECD with N-term. GST tag; nucleic
      acid

<400> SEQUENCE: 54

Ala Thr Gly Gly Thr Cys Ala Thr Gly Thr Cys Cys Cys Cys Thr Ala
1               5                   10                  15

Thr Ala Cys Thr Ala Gly Gly Thr Thr Ala Thr Gly Gly Ala Ala
            20                  25                  30

Ala Ala Thr Thr Ala Ala Gly Gly Gly Cys Cys Thr Thr Gly Thr Gly
        35                  40                  45

Cys Ala Ala Cys Cys Cys Ala Cys Thr Cys Gly Ala Cys Thr Thr Cys
```

```
    50                  55                  60

Thr Thr Thr Thr Gly Gly Ala Ala Thr Ala Thr Cys Thr Thr Gly Ala
65                  70                  75                  80

Ala Gly Ala Ala Ala Ala Ala Thr Ala Thr Gly Ala Ala Gly Ala Gly
                85                  90                  95

Cys Ala Thr Thr Thr Gly Thr Ala Thr Gly Ala Gly Cys Gly Cys Gly
            100                 105                 110

Ala Thr Gly Ala Ala Gly Gly Thr Gly Ala Thr Ala Ala Ala Thr Gly
        115                 120                 125

Gly Cys Gly Ala Ala Ala Cys Ala Ala Ala Ala Ala Gly Thr Thr Thr
    130                 135                 140

Gly Ala Ala Thr Thr Gly Gly Gly Thr Thr Thr Gly Gly Ala Gly Thr
145                 150                 155                 160

Thr Thr Cys Cys Cys Ala Ala Thr Cys Thr Thr Cys Cys Thr Thr Ala
                165                 170                 175

Thr Thr Ala Thr Ala Thr Thr Gly Ala Thr Gly Gly Thr Gly Ala Thr
            180                 185                 190

Gly Thr Thr Ala Ala Ala Thr Thr Ala Ala Cys Ala Cys Ala Gly Thr
        195                 200                 205

Cys Thr Ala Thr Gly Gly Cys Cys Ala Thr Cys Ala Thr Ala Cys Gly
    210                 215                 220

Thr Thr Ala Thr Ala Thr Ala Gly Cys Thr Gly Ala Cys Ala Ala Gly
225                 230                 235                 240

Cys Ala Cys Ala Ala Cys Ala Thr Gly Thr Thr Gly Gly Gly Thr Gly
                245                 250                 255

Gly Thr Thr Gly Thr Cys Cys Ala Ala Ala Ala Gly Ala Gly Cys Gly
            260                 265                 270

Thr Gly Cys Ala Gly Ala Gly Ala Thr Thr Thr Cys Ala Ala Thr Gly
        275                 280                 285

Cys Thr Thr Gly Ala Ala Gly Gly Ala Gly Cys Gly Gly Thr Thr Thr
    290                 295                 300

Thr Gly Gly Ala Thr Ala Thr Thr Ala Gly Ala Thr Ala Cys Gly Gly
305                 310                 315                 320

Thr Gly Thr Thr Thr Cys Gly Ala Gly Ala Ala Thr Thr Gly Cys Ala
                325                 330                 335

Thr Ala Thr Ala Gly Thr Ala Ala Ala Gly Ala Cys Thr Thr Thr Gly
            340                 345                 350

Ala Ala Ala Cys Thr Cys Thr Cys Ala Ala Ala Gly Thr Thr Gly Ala
        355                 360                 365

Thr Thr Thr Thr Cys Thr Thr Ala Gly Cys Ala Ala Gly Cys Thr Ala
    370                 375                 380

Cys Cys Thr Gly Ala Ala Ala Thr Gly Cys Thr Gly Ala Ala Ala Ala
385                 390                 395                 400

Thr Gly Thr Thr Cys Gly Ala Ala Gly Ala Thr Cys Gly Thr Thr Thr
                405                 410                 415

Ala Thr Gly Thr Cys Ala Thr Ala Ala Ala Ala Cys Ala Thr Ala Thr
            420                 425                 430

Thr Thr Ala Ala Ala Thr Gly Gly Thr Gly Ala Thr Cys Ala Thr Gly
        435                 440                 445

Thr Ala Ala Cys Cys Cys Ala Thr Cys Cys Thr Gly Ala Cys Thr Thr
    450                 455                 460

Cys Ala Thr Gly Thr Thr Gly Thr Ala Thr Gly Ala Cys Gly Cys Thr
465                 470                 475                 480
```

```
Cys Thr Thr Gly Ala Thr Gly Thr Thr Gly Thr Thr Thr Thr Ala Thr
                485                 490                 495

Ala Cys Ala Thr Gly Gly Ala Cys Cys Cys Ala Ala Thr Gly Thr Gly
            500                 505                 510

Cys Cys Thr Gly Gly Ala Thr Gly Cys Gly Thr Thr Cys Cys Cys Ala
        515                 520                 525

Ala Ala Ala Thr Thr Ala Gly Thr Thr Thr Gly Thr Thr Thr Thr Ala
    530                 535                 540

Ala Ala Ala Ala Ala Cys Gly Thr Ala Thr Thr Gly Ala Ala Gly Cys
545                 550                 555                 560

Thr Ala Thr Cys Cys Cys Ala Cys Ala Ala Ala Thr Thr Gly Ala Thr
                565                 570                 575

Ala Ala Gly Thr Ala Cys Thr Thr Gly Ala Ala Ala Thr Cys Cys Ala
            580                 585                 590

Gly Cys Ala Ala Gly Thr Ala Thr Ala Thr Ala Gly Cys Ala Thr Gly
        595                 600                 605

Gly Cys Cys Thr Thr Thr Gly Cys Ala Gly Gly Gly Cys Thr Gly Gly
    610                 615                 620

Cys Ala Ala Gly Cys Cys Ala Cys Gly Thr Thr Thr Gly Gly Thr Gly
625                 630                 635                 640

Gly Thr Gly Gly Cys Gly Ala Cys Cys Ala Thr Cys Cys Thr Cys Cys
                645                 650                 655

Ala Ala Ala Ala Thr Cys Gly Gly Ala Thr Gly Gly Cys Gly Gly Thr
            660                 665                 670

Ala Gly Cys Gly Gly Gly Ala Thr Gly Gly Ala Gly Gly Ala Cys Gly
        675                 680                 685

Ala Ala Ala Ala Gly Cys Cys Thr Ala Ala Ala Gly Thr Gly Ala Ala
    690                 695                 700

Thr Cys Cys Cys Ala Ala Ala Thr Thr Gly Thr Ala Thr Ala Thr Gly
705                 710                 715                 720

Thr Gly Cys Gly Thr Cys Thr Gly Cys Gly Ala Ala Gly Gly Ala Cys
                725                 730                 735

Thr Gly Thr Cys Ala Thr Gly Thr Gly Gly Thr Ala Ala Thr Gly Ala
            740                 745                 750

Ala Gly Ala Thr Cys Ala Thr Thr Gly Cys Gly Ala Ala Gly Gly Gly
        755                 760                 765

Cys Ala Ala Cys Ala Ala Thr Gly Cys Thr Thr Cys Ala Gly Cys Ala
    770                 775                 780

Gly Cys Thr Thr Gly Thr Cys Ala Ala Thr Cys Ala Ala Cys Gly Ala
785                 790                 795                 800

Cys Gly Gly Ala Thr Thr Thr Cys Ala Cys Gly Thr Gly Thr Ala Thr
                805                 810                 815

Cys Ala Ala Ala Ala Ala Gly Gly Ala Thr Gly Thr Thr Thr Cys Cys
            820                 825                 830

Ala Ala Gly Thr Gly Thr Ala Cys Gly Ala Ala Cys Ala Ala Gly Gly
        835                 840                 845

Thr Ala Ala Ala Ala Thr Gly Ala Cys Thr Thr Gly Cys Ala Ala Ala
    850                 855                 860

Ala Cys Gly Cys Cys Ala Cys Cys Thr Thr Cys Cys Cys Cys Gly Gly
865                 870                 875                 880

Gly Ala Cys Ala Ala Gly Cys Gly Gly Thr Cys Gly Ala Ala Thr Gly
                885                 890                 895
```

```
Thr Thr Gly Thr Cys Ala Gly Gly Cys Gly Ala Thr Gly Gly
            900                 905                 910

Thr Gly Thr Ala Ala Thr Cys Gly Cys Ala Ala Thr Thr Cys Ala
        915                 920                 925

Cys Thr Gly Cys Ala Cys Ala Gly Cys Thr Cys Cys Gly Ala Cys
    930                 935                 940

Cys Ala Ala Gly Gly Ala Ala Gly Thr Cys Gly Thr Thr
945             950                 955                 960

Cys Cys Gly Gly Gly Cys Ala Cys Cys Ala Ala Ala Thr Thr
                965                 970                 975

Thr Thr Cys Ala Thr Cys Thr Cys Gly Ala Gly
            980                 985

<210> SEQ ID NO 55
<211> LENGTH: 438
<212> TYPE: PRT
<213> ORGANISM: Homo sapiens
<220> FEATURE:
<221> NAME/KEY: misc_feature
<222> LOCATION: (1)..(438)
<223> OTHER INFORMATION: Human ALK2 ECD with C-terminal transmembrane
      domain

<400> SEQUENCE: 55

Ala Thr Gly Gly Thr Cys Gly Ala Cys Gly Gly Cys Gly Thr Ala
1               5                   10                  15

Thr Gly Ala Thr Cys Cys Thr Gly Cys Cys Gly Gly Thr Gly Cys Thr
            20                  25                  30

Thr Ala Thr Cys Ala Thr Gly Ala Thr Cys Gly Cys Cys Thr Cys
        35                  40                  45

Cys Cys Ala Thr Cys Gly Cys Cys Gly Thr Cys Cys Ala Thr Gly Gly
    50                  55                  60

Ala Gly Gly Ala Cys Gly Ala Ala Ala Gly Cys Cys Thr Ala Ala
65              70                  75                  80

Ala Gly Thr Gly Ala Ala Thr Cys Cys Ala Ala Ala Thr Gly Gly
            85                  90                  95

Thr Ala Thr Ala Thr Gly Thr Cys Gly Thr Cys Thr Gly Cys Gly
            100                 105                 110

Ala Ala Gly Gly Ala Cys Thr Gly Thr Cys Ala Thr Gly Thr Gly Gly
            115                 120                 125

Thr Ala Ala Thr Gly Ala Ala Gly Ala Thr Cys Ala Thr Thr Gly Cys
            130                 135                 140

Gly Ala Ala Gly Gly Cys Ala Cys Ala Ala Thr Gly Cys Thr
145             150                 155                 160

Thr Cys Ala Gly Cys Ala Gly Cys Thr Thr Gly Thr Cys Ala Ala Thr
            165                 170                 175

Cys Ala Ala Cys Gly Ala Cys Gly Gly Ala Thr Thr Thr Cys Ala Cys
            180                 185                 190

Gly Thr Gly Thr Ala Thr Cys Ala Ala Ala Ala Gly Gly Ala Thr
            195                 200                 205

Gly Thr Thr Thr Cys Cys Ala Ala Gly Thr Gly Thr Ala Cys Gly Ala
            210                 215                 220

Ala Cys Ala Ala Gly Gly Thr Ala Ala Ala Thr Gly Ala Cys Thr
225             230                 235                 240

Thr Gly Cys Ala Ala Ala Ala Cys Gly Cys Cys Ala Cys Thr Thr
            245                 250                 255
```

Cys Cys Cys Cys Gly Gly Ala Cys Ala Ala Gly Cys Gly Gly Thr
                260                 265                 270

Cys Gly Ala Ala Thr Gly Thr Gly Thr Cys Ala Gly Gly Cys
            275                 280                 285

Gly Ala Thr Thr Gly Gly Thr Gly Thr Ala Ala Thr Cys Gly Cys Ala
            290                 295                 300

Ala Thr Ala Thr Cys Ala Cys Thr Gly Cys Ala Cys Ala Gly Cys Thr
305                 310                 315                 320

Cys Cys Cys Gly Ala Cys Cys Ala Ala Gly Gly Ala Ala Ala Gly
                325                 330                 335

Thr Cys Gly Thr Thr Thr Cys Gly Gly Cys Ala Cys Cys Cys
                340                 345                 350

Ala Ala Ala Ala Thr Thr Thr Thr Cys Ala Thr Cys Thr Cys Gly Ala
                355                 360                 365

Gly Gly Thr Gly Gly Ala Cys Thr Cys Ala Thr Cys Ala Thr Thr
                370                 375                 380

Cys Thr Gly Thr Cys Gly Gly Thr Gly Gly Thr Cys Gly
385                 390                 395                 400

Cys Cys Gly Thr Gly Thr Gly Cys Cys Thr Gly Cys Thr Gly Gly Cys
                405                 410                 415

Thr Thr Gly Cys Cys Thr Thr Cys Thr Gly Gly Gly Gly Thr Cys
                420                 425                 430

Gly Cys Cys Cys Thr Gly
            435

<210> SEQ ID NO 56
<211> LENGTH: 990
<212> TYPE: PRT
<213> ORGANISM: Homo sapiens
<220> FEATURE:
<221> NAME/KEY: misc_feature
<222> LOCATION: (1)..(990)
<223> OTHER INFORMATION: Human IgG1 constant region

<400> SEQUENCE: 56

Gly Cys Cys Thr Cys Cys Ala Cys Cys Ala Ala Gly Gly Gly Cys Cys
1               5                   10                  15

Cys Ala Thr Cys Gly Gly Thr Cys Thr Thr Cys Cys Cys Cys Thr
                20                  25                  30

Gly Gly Cys Ala Cys Cys Cys Thr Cys Cys Thr Cys Cys Ala Ala Gly
                35                  40                  45

Ala Gly Cys Ala Cys Cys Thr Cys Thr Gly Gly Cys Gly Gly Cys Ala
            50                  55                  60

Cys Ala Gly Cys Gly Gly Cys Cys Cys Thr Gly Gly Gly Cys Thr Gly
65                  70                  75                  80

Cys Cys Thr Gly Gly Thr Cys Ala Ala Gly Gly Ala Cys Thr Ala Cys
                85                  90                  95

Thr Thr Cys Cys Cys Cys Gly Ala Ala Cys Cys Gly Gly Thr Gly Ala
                100                 105                 110

Cys Gly Gly Thr Gly Thr Cys Gly Thr Gly Gly Ala Ala Cys Thr Cys
                115                 120                 125

Ala Gly Gly Cys Gly Cys Cys Cys Thr Gly Ala Cys Cys Ala Gly Cys
                130                 135                 140

Gly Gly Cys Gly Thr Gly Cys Ala Cys Ala Cys Cys Thr Thr Cys Cys
145                 150                 155                 160

Cys Gly Gly Cys Thr Gly Thr Cys Cys Thr Ala Cys Ala Gly Thr Cys

-continued

```
            165                 170                 175
Cys Thr Cys Ala Gly Ala Cys Thr Cys Thr Ala Cys Thr Cys Cys
            180                 185                 190
Cys Thr Cys Ala Gly Cys Ala Gly Cys Gly Thr Gly Thr Gly Ala
            195                 200                 205
Cys Cys Gly Thr Gly Cys Cys Thr Cys Cys Ala Gly Cys Ala Gly
    210                 215                 220
Cys Thr Thr Gly Gly Gly Cys Ala Cys Cys Ala Gly Ala Cys Cys
225                 230                 235                 240
Thr Ala Cys Ala Thr Cys Thr Gly Cys Ala Ala Cys Gly Thr Ala
                245                 250                 255
Ala Thr Cys Ala Cys Ala Ala Gly Cys Cys Ala Gly Cys Ala Ala
                260                 265                 270
Cys Ala Cys Cys Ala Ala Gly Gly Thr Gly Gly Ala Cys Ala Ala
            275                 280                 285
Ala Gly Ala Gly Thr Thr Gly Ala Gly Cys Cys Ala Ala Ala Thr
    290                 295                 300
Cys Thr Thr Gly Thr Gly Ala Cys Ala Ala Ala Cys Thr Cys Ala
305                 310                 315                 320
Cys Ala Cys Ala Thr Gly Cys Cys Cys Ala Cys Cys Gly Thr Gly Cys
                325                 330                 335
Cys Cys Ala Gly Cys Ala Cys Cys Thr Gly Ala Ala Cys Thr Cys
            340                 345                 350
Thr Gly Gly Gly Gly Gly Gly Ala Cys Cys Gly Thr Cys Ala Gly Thr
        355                 360                 365
Cys Thr Thr Cys Cys Thr Cys Thr Thr Cys Cys Cys Cys Cys Ala
    370                 375                 380
Ala Ala Ala Cys Cys Cys Ala Ala Gly Gly Ala Cys Ala Cys Cys Cys
385                 390                 395                 400
Thr Cys Ala Thr Gly Ala Thr Cys Thr Cys Cys Cys Gly Gly Ala Cys
                405                 410                 415
Cys Cys Cys Thr Gly Ala Gly Gly Thr Cys Ala Cys Ala Thr Gly Cys
                420                 425                 430
Gly Thr Gly Gly Thr Gly Gly Thr Gly Gly Ala Cys Gly Thr Gly Ala
        435                 440                 445
Gly Cys Cys Ala Cys Gly Ala Ala Gly Ala Cys Cys Cys Thr Gly Ala
    450                 455                 460
Gly Gly Thr Cys Ala Ala Gly Thr Thr Cys Ala Ala Cys Thr Gly Gly
465                 470                 475                 480
Thr Ala Cys Gly Thr Gly Gly Ala Cys Gly Gly Cys Gly Thr Gly Gly
                485                 490                 495
Ala Gly Gly Thr Gly Cys Ala Thr Ala Ala Thr Gly Cys Cys Ala Ala
                500                 505                 510
Gly Ala Cys Ala Ala Gly Cys Cys Gly Cys Gly Gly Gly Ala Gly Gly
            515                 520                 525
Gly Ala Gly Cys Ala Gly Thr Ala Cys Ala Ala Cys Ala Gly Cys Ala
        530                 535                 540
Cys Gly Thr Ala Cys Cys Gly Thr Gly Thr Gly Gly Thr Cys Ala Gly
545                 550                 555                 560
Cys Gly Thr Cys Cys Thr Cys Ala Cys Cys Gly Thr Cys Cys Thr Gly
                565                 570                 575
Cys Ala Cys Cys Ala Gly Gly Ala Cys Thr Gly Gly Cys Thr Gly Ala
            580                 585                 590
```

-continued

```
Ala Thr Gly Gly Cys Ala Ala Gly Gly Ala Gly Thr Ala Cys Ala Ala
            595                 600                 605
Gly Thr Gly Cys Ala Ala Gly Gly Thr Cys Thr Cys Cys Ala Ala Cys
        610                 615                 620
Ala Ala Ala Gly Cys Cys Cys Thr Cys Cys Ala Gly Cys Cys Cys
625                 630                 635                 640
Cys Cys Ala Thr Cys Gly Ala Gly Ala Ala Ala Cys Cys Ala Thr
            645                 650                 655
Cys Thr Cys Cys Ala Ala Ala Gly Cys Cys Ala Ala Gly Gly Gly
        660                 665                 670
Cys Ala Gly Cys Cys Cys Gly Ala Gly Ala Cys Cys Ala Cys
    675                 680                 685
Ala Gly Gly Thr Gly Thr Ala Cys Ala Cys Cys Thr Gly Cys Cys
    690                 695                 700
Cys Cys Cys Ala Thr Cys Cys Gly Gly Ala Gly Gly Ala Gly
705                 710                 715                 720
Ala Thr Gly Ala Cys Cys Ala Ala Gly Ala Cys Cys Ala Gly Gly
            725                 730                 735
Thr Cys Ala Gly Cys Cys Thr Gly Ala Cys Cys Thr Gly Cys Thr
        740                 745                 750
Gly Gly Thr Cys Ala Ala Ala Gly Gly Cys Thr Thr Cys Thr Ala Thr
            755                 760                 765
Cys Cys Cys Ala Gly Cys Gly Ala Cys Ala Thr Cys Gly Cys Cys Gly
770                 775                 780
Thr Gly Gly Ala Gly Thr Gly Gly Gly Ala Gly Ala Gly Cys Ala Ala
785                 790                 795                 800
Thr Gly Gly Gly Cys Ala Gly Cys Cys Gly Gly Ala Gly Ala Ala Cys
            805                 810                 815
Ala Ala Cys Thr Ala Cys Ala Ala Gly Ala Cys Cys Ala Cys Gly Cys
            820                 825                 830
Cys Thr Cys Cys Cys Gly Thr Gly Cys Thr Gly Gly Ala Cys Thr Cys
        835                 840                 845
Cys Gly Ala Cys Gly Gly Cys Thr Cys Cys Thr Thr Cys Thr Thr Cys
    850                 855                 860
Cys Thr Cys Thr Ala Thr Ala Gly Cys Ala Ala Gly Cys Thr Cys Ala
865                 870                 875                 880
Cys Cys Gly Thr Gly Gly Ala Cys Ala Ala Gly Ala Gly Cys Ala Gly
            885                 890                 895
Gly Thr Gly Gly Cys Ala Gly Cys Ala Gly Gly Gly Gly Ala Ala Cys
            900                 905                 910
Gly Thr Cys Thr Thr Cys Thr Cys Ala Thr Gly Cys Thr Cys Cys Gly
        915                 920                 925
Thr Gly Ala Thr Gly Cys Ala Thr Gly Ala Gly Gly Cys Thr Cys Thr
    930                 935                 940
Gly Cys Ala Cys Ala Ala Cys Cys Ala Cys Thr Ala Cys Ala Cys Gly
945                 950                 955                 960
Cys Ala Gly Ala Ala Gly Ala Gly Cys Cys Thr Cys Thr Cys Cys Cys
            965                 970                 975
Thr Gly Thr Cys Cys Cys Cys Gly Gly Gly Thr Ala Ala Ala
            980                 985                 990
```

<210> SEQ ID NO 57
<211> LENGTH: 978

<212> TYPE: DNA
<213> ORGANISM: Artificial Sequence
<220> FEATURE:
<223> OTHER INFORMATION: Synthetic: IgG2/4 hybrid Fc; nucleic acid

<400> SEQUENCE: 57

```
gcctccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca ggaagacccc gaggtccagt tcaactggta cgtggatggc     480
gtggaggtgc ataatgccaa gacaaagccg cgggaggagc agttcaacag cacgtaccgt     540
gtggtcagcg tcctcaccgt cctgcaccag gactggctga acggcaagga gtacaagtgc     600
aaggtctcca acaaaggcct cccgtcctcc atcgagaaaa ccatctccaa agccaaaggg     660
cagccccgag agccacaggt gtacaccctg cccccatccc aggaggagat gaccaagaac     720
caggtcagcc tgacctgcct ggtcaaaggc ttctacccca gcgacatcgc cgtggagtgg     780
gagagcaatg ggcagccgga gaacaactac aagaccacgc ctcccgtgct ggactccgac     840
ggctccttct tcctctacag caggctaacc gtggacaaga gcaggtggca ggaggggaat     900
gtcttctcat gctccgtgat gcatgaggct ctgcacaacc actacacaca gaagagcctc     960
tccctgtctc tgggtaaa                                                   978
```

<210> SEQ ID NO 58
<211> LENGTH: 30
<212> TYPE: DNA
<213> ORGANISM: Artificial Sequence
<220> FEATURE:
<223> OTHER INFORMATION: Synthetic: JAB0399 VHCDR1; Nucleic acid

<400> SEQUENCE: 58

```
ggcttcaaca ttaaagacag ccttatgcac                                       30
```

<210> SEQ ID NO 59
<211> LENGTH: 48
<212> TYPE: DNA
<213> ORGANISM: Artificial Sequence
<220> FEATURE:
<223> OTHER INFORMATION: Synthetic: JAB0399 VHCDR2; nucleic acid

<400> SEQUENCE: 59

```
attgatcctg aggatggtga aactaaatat gccccgaact tccaggac                   48
```

<210> SEQ ID NO 60
<211> LENGTH: 30
<212> TYPE: DNA
<213> ORGANISM: Artificial Sequence
<220> FEATURE:
<223> OTHER INFORMATION: Synthetic: JAB0399 VHCDR3; nucleic acid

<400> SEQUENCE: 60

```
tatacttccg attactatac tatggactac                                       30
```

<210> SEQ ID NO 61

```
<211> LENGTH: 33
<212> TYPE: DNA
<213> ORGANISM: Artificial Sequence
<220> FEATURE:
<223> OTHER INFORMATION: Synthetic: JAB0399 VLCDR1; nucleic acid

<400> SEQUENCE: 61
ctggcaagtc agaccattgg tacatggtta gca                                 33

<210> SEQ ID NO 62
<211> LENGTH: 21
<212> TYPE: DNA
<213> ORGANISM: Artificial Sequence
<220> FEATURE:
<223> OTHER INFORMATION: Synthetic: JAB0399 VLCDR2; nucleic acid

<400> SEQUENCE: 62
gctgcaacca gcttggcaga t                                              21

<210> SEQ ID NO 63
<211> LENGTH: 27
<212> TYPE: DNA
<213> ORGANISM: Artificial Sequence
<220> FEATURE:
<223> OTHER INFORMATION: Synthetic: JAB0399 VLCDR3; nucleic acid

<400> SEQUENCE: 63
caacaacttt acagtactcc gtggacg                                        27

<210> SEQ ID NO 64
<211> LENGTH: 356
<212> TYPE: DNA
<213> ORGANISM: Artificial Sequence
<220> FEATURE:
<223> OTHER INFORMATION: Synthetic: JAB0399 VH; nucleic acid

<400> SEQUENCE: 64
gaggtccaac tgcaacagtc tggggcagag cttgtgaggc caggggcctc agtcaggttg     60
tcctgcacag cttctggctt caacattaaa gacagcctta tgcactgggt gaagcagagg    120
cctgaacagg gcctggagtg gattggatgg attgatcctg aggatggtga aactaaatat    180
gccccgaact tccaggacaa ggccactata actgcagtca catcctccaa cacagcctac    240
ctgcagctca gcagcctgac atctgaggac tctgccatct attactgtgc taggtatact    300
tccgattact atactatgga ctactggggt caaggaacct cggtcaccgt ctcctc        356

<210> SEQ ID NO 65
<211> LENGTH: 323
<212> TYPE: DNA
<213> ORGANISM: Artificial Sequence
<220> FEATURE:
<223> OTHER INFORMATION: Synthetic: JAB0399 VL; nucleic acid

<400> SEQUENCE: 65
gacatccaga tgacccagtc tcctgcctcc cagtctgcat ctctgggaga agtgtcacc      60 ttcacatgcc tggcaagtca gaccattggt acatggttag catggtatca gcagaaacca   120
gggaaatctc ctcagctcct gatttatgct gcaaccagct ggcagatggg gtcccatca    180 aggttcagtg gtagtggatc tggcacaaag ttttctttca agatcagcag cctacaggct   240
gaagattttg caagttatta ctgtcaacaa ctttacagta ctccgtggac gttcggtgga   300
ggcaccaagc tggaaatcaa acg                                            323
```

<210> SEQ ID NO 66
<211> LENGTH: 1332
<212> TYPE: DNA
<213> ORGANISM: Artificial Sequence
<220> FEATURE:
<223> OTHER INFORMATION: Synthetic: JAB0399 HC; nucleic acid
<220> FEATURE:
<221> NAME/KEY: misc_feature
<222> LOCATION: (480)..(480)
<223> OTHER INFORMATION: n is a, c, g, or t

<400> SEQUENCE: 66

```
gaggtccaac tgcaacagtc tggggcagag cttgtgaggc caggggcctc agtcaggttg      60
tcctgcacag cttctggctt caacattaaa gacagcctta tgcactgggt gaagcagagg     120
cctgaacagg gcctggagtg gattggatgg attgatcctg aggatggtga actaaatat      180 gccccgaact tccaggacaa ggccactata actgcagtca catcctccaa cacagcctac     240
ctgcagctca gcagcctgac atctgaggac tctgccatct attactgtgc taggtatact     300
tccgattact atactatgga ctactgggggt caaggaacct cggtcaccgt ctcctcggct     360
aaaacgacac cccccatctgt ctatccgcta gcccctggat tgctgccca aactaactcc     420 atggtgacgc tgggatgcct ggtcaagggc tatttccctg agccagtgac agtgacctgn     480
aactctggat ccctgtccag cggtgtgcac accttcccag ctgtcctgca gtctgacctc     540
tacactctga gcagctcagt gactgtcccc tccagcacct ggcccagcca gaccgtcacc     600
tgcaacgttg cccacccggc cagcagcacc aaggtggaca gaaaattgt gcccagggat     660 tgtggttgta agccttgcat atgtacagtc ccagaagtat catctgtctt catcttcccc     720
ccaaagccca aggatgtgct caccattact ctgactccta aggtcacgtg tgttgtggta     780
gacatcagca aggatgatcc cgaggtccag ttcagctggt ttgtagatga tgtggaggtg     840
cacacagctc agacgaaacc ccgggaggag cagatcaaca gcactttccg ttcagtcagt     900
gaacttccca tcatgcacca ggactggctc aatggcaagg agttcaaatg cagggtcaac     960
agtgcagctt tccctgcccc catcgagaaa accatctcca aaaccaaagg cagaccgaag    1020
gctccacagg tgtacaccat tccacctccc aaggagcaga tggccaagga taaagtcagt    1080
ctgacctgca tgataacaaa cttcttccct gaagacatta ctgtggagtg cagtggaat    1140 gggcagccag cggagaacta caagaacact cagcccatca tggacacaga tggctcttac    1200
ttcgtctaca gcaagctcaa tgtgcagaag agcaactggg aggcaggaaa tactttcacc    1260
tgctctgtgt acatgagggg cctgcacaac caccatactg agaagagcct ctcccactct    1320
cctggtaaat ga                                                        1332
```

<210> SEQ ID NO 67
<211> LENGTH: 645
<212> TYPE: DNA
<213> ORGANISM: Artificial Sequence
<220> FEATURE:
<223> OTHER INFORMATION: Synthetic: JAB0399 LC; nucleic acid

<400> SEQUENCE: 67

```
gacatccaga tgacccagtc tcctgcctcc cagtctgcat ctctgggaga aagtgtcacc      60
ttcacatgcc tggcaagtca gaccattggt acatggttag catggtatca gcagaaacca     120
gggaaatctc ctcagctcct gatttatgct gcaaccagct ggcagatgg ggtcccatca     180 aggttcagtg gtagtggatc tggcacaaag ttttctttca agatcagcag cctacaggct     240
gaagattttg caagttatta ctgtcaacaa ctttacagta ctccgtggac gttcggtgga     300
```

```
ggcaccaagc tggaaatcaa acgggctgat gctgcaccaa ctgtatccat cttcccacca    360
tccagtgagc agttaacatc cggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttaa                    645

<210> SEQ ID NO 68
<211> LENGTH: 29
<212> TYPE: DNA
<213> ORGANISM: Artificial Sequence
<220> FEATURE:
<223> OTHER INFORMATION: Synthetic: JAB0481 VHCDR1; Nucleic acid

<400> SEQUENCE: 68
ggcttcaaca ttaaagacag ccttatgca                                       29

<210> SEQ ID NO 69
<211> LENGTH: 48
<212> TYPE: DNA
<213> ORGANISM: Artificial Sequence
<220> FEATURE:
<223> OTHER INFORMATION: Synthetic: JAB0481 VHCDR2; nucleic acid

<400> SEQUENCE: 69
attgatcctg aggatggtga aactaaatat gccccgaact tccaggac                  48

<210> SEQ ID NO 70
<211> LENGTH: 30
<212> TYPE: DNA
<213> ORGANISM: Artificial Sequence
<220> FEATURE:
<223> OTHER INFORMATION: Synthetic: JAB0481 VHCDR3; nucleic acid

<400> SEQUENCE: 70
tatacttccg attactatac tatggactac                                      30

<210> SEQ ID NO 71
<211> LENGTH: 33
<212> TYPE: DNA
<213> ORGANISM: Artificial Sequence
<220> FEATURE:
<223> OTHER INFORMATION: Synthetic: JAB0481 VLCDR1; nucleic acid

<400> SEQUENCE: 71
ctggcaagtc agaccattgg tacatggtta gca                                  33

<210> SEQ ID NO 72
<211> LENGTH: 21
<212> TYPE: DNA
<213> ORGANISM: Artificial Sequence
<220> FEATURE:
<223> OTHER INFORMATION: Synthetic: JAB0481 VLCDR2; nucleic acid

<400> SEQUENCE: 72
gctgcaacca gcttggcaga t                                               21

<210> SEQ ID NO 73
<211> LENGTH: 27
<212> TYPE: DNA
<213> ORGANISM: Artificial Sequence
<220> FEATURE:
<223> OTHER INFORMATION: Synthetic: JAB0481 VLCDR3; nucleic acid
```

<400> SEQUENCE: 73 caacaactttt acagtactcc gtggacg						27

<210> SEQ ID NO 74
<211> LENGTH: 357
<212> TYPE: DNA
<213> ORGANISM: Artificial Sequence
<220> FEATURE:
<223> OTHER INFORMATION: Synthetic: JAB0481 VH; nucleic acid

<400> SEQUENCE: 74
gaggtccaac tgcaacagtc tggggcagag cttgtgaggc caggggcctc agtcaggttg		60 tcctgcacag cttctggctt caacattaaa gacagcctta tgcactgggt gaagcagagg		120 cctgaacagg gcctggagtg gattggatgg attgatcctg aggatggtga aactaaatat		180 gccccgaact tccaggacaa ggccactata actgcagtca catcctccaa cacagcctac		240 ctgcagctca gcagcctgac atctgaggac tctgccatct attactgtgc taggtatact		300 tccgattact atactatgga ctactggggt caaggaacct cggtcaccgt ctcctcg		357

<210> SEQ ID NO 75
<211> LENGTH: 323
<212> TYPE: DNA
<213> ORGANISM: Artificial Sequence
<220> FEATURE:
<223> OTHER INFORMATION: Synthetic: JAB0481 VL; nucleic acid

<400> SEQUENCE: 75
gacatccaga tgacccagtc tcctgcctcc cagtctgcat ctctgggaga aagtgtcacc		60 ttcacatgcc tggcaagtca gaccattggt acatggttag catggtatca gcagaaacca		120 gggaaatctc tcagctcct gatttatgct gcaaccagct ggcagatgg ggtcccatca		180 aggttcagtg gtagtggatc tggcacaaag ttttctttca agatcagcag cctacaggct		240 gaagattttg caagttatta ctgtcaacaa ctttacagta ctccgtggac gttcggtgga		300 ggcaccaagc tggaaatcaa acg		323

<210> SEQ ID NO 76
<211> LENGTH: 1332
<212> TYPE: DNA
<213> ORGANISM: Artificial Sequence
<220> FEATURE:
<223> OTHER INFORMATION: Synthetic: JAB0481 HC; nucleic acid

<400> SEQUENCE: 76
gaggtccaac tgcaacagtc tggggcagag cttgtgaggc caggggcctc agtcaggttg		60 tcctgcacag cttctggctt caacattaaa gacagcctta tgcactgggt gaagcagagg		120 cctgaacagg gcctggagtg gattggatgg attgatcctg aggatggtga aactaaatat		180 gccccgaact tccaggacaa ggccactata actgcagtca catcctccaa cacagcctac		240 ctgcagctca gcagcctgac atctgaggac tctgccatct attactgtgc taggtatact		300 tccgattact atactatgga ctactggggt caaggaacct cggtcaccgt ctcctcggct		360 aaaacgacac cccatctgt ctatccgcta gcccctggat ctgctgccca aactaactcc		420 atggtgacgc tgggatgcct ggtcaagggc tatttccctg agccagtgac agtgacctgg		480 aactctggat ccctgtccag cggtgtgcac accttcccag ctgtcctgca gtctgacctc		540 tacactctga gcagctcagt gactgtcccc tccagcacct ggcccagcca gaccgtcacc		600

```
tgcaacgttg cccacccggc cagcagcacc aaggtggaca agaaaattgt gcccagggat    660
tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgaaacc ccgggaggag cagatcaaca gcactttccg ttcagtcagt    900
gaacttccca tcatgcacca ggactggctc aatggcaagg agttcaaatg cagggtcaac    960
agtgcagctt tccctgcccc catcgagaaa accatctcca aaaccaaagg cagaccgaag    1020
gctccacagg tgtacaccat tccacctccc aaggagcaga tggccaagga taaagtcagt    1080
ctgacctgca tgataacaaa cttcttccct gaagacatta ctgtggagtg cagtggaat    1140 gggcagccag cggagaacta caagaacact cagcccatca tggacacaga tggctcttac    1200
ttcgtctaca gcaagctcaa tgtgcagaag agcaactggg aggcaggaaa tactttcacc    1260
tgctctgtgt tacatgaggg cctgcacaac caccatactg agaagagcct ctcccactct    1320
cctggtaaat ga                                                        1332
```

<210> SEQ ID NO 77
<211> LENGTH: 645
<212> TYPE: DNA
<213> ORGANISM: Artificial Sequence
<220> FEATURE:
<223> OTHER INFORMATION: Synthetic: JAB0481 LC; nucleic acid

<400> SEQUENCE: 77

```
gacatccaga tgacccagtc tcctgcctcc cagtctgcat ctctgggaga aagtgtcacc     60
ttcacatgcc tggcaagtca gaccattggt acatggttag catggtatca gcagaaacca    120
gggaaatctc ctcagctcct gatttatgct gcaaccagct ggcagatgg ggtcccatca    180 aggttcagtg gtagtggatc tggcacaaag ttttctttca agatcagcag cctacaggct    240
gaagattttg caagttatta ctgtcaacaa ctttacagta ctccgtggac gttcggtgga    300
ggcaccaagc tggaaatcaa acgggctgat gctgcaccaa ctgtatccat cttcccacca    360
tccagtgagc agttaacatc cggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag cacccctcacg    540 ttgaccaagg acgagtatga acgacataac agctatacct gtgaggccac tcacaagaca    600
tcaacttcac ccattgtcaa gagcttcaac aggaatgagt gttaa                     645
```

<210> SEQ ID NO 78
<211> LENGTH: 30
<212> TYPE: DNA
<213> ORGANISM: Artificial Sequence
<220> FEATURE:
<223> OTHER INFORMATION: Synthetic: JAB0501 VHCDR1; nucleic acid

<400> SEQUENCE: 78

```
ggcttcaaca ttaaagacag ccttatgcac                                       30
```

<210> SEQ ID NO 79
<211> LENGTH: 48
<212> TYPE: DNA
<213> ORGANISM: Artificial Sequence
<220> FEATURE:
<223> OTHER INFORMATION: Synthetic: JAB0501 VHCDR2; nucleic acid

<400> SEQUENCE: 79

-continued attgatcctg aggatggtga aactaaatat gccccgaact tccagtct 48

<210> SEQ ID NO 80
<211> LENGTH: 30
<212> TYPE: DNA
<213> ORGANISM: Artificial Sequence
<220> FEATURE:
<223> OTHER INFORMATION: Synthetic: JAB0501 VHCDR3; nucleic acid

<400> SEQUENCE: 80
tatacttccc cgtactatac tatggactac 30

<210> SEQ ID NO 81
<211> LENGTH: 33
<212> TYPE: DNA
<213> ORGANISM: Artificial Sequence
<220> FEATURE:
<223> OTHER INFORMATION: Synthetic: JAB0501 VLCDR1; nucleic acid

<400> SEQUENCE: 81
ctggcaagtc agaccattgg tacatggtta gca 33

<210> SEQ ID NO 82
<211> LENGTH: 21
<212> TYPE: DNA
<213> ORGANISM: Artificial Sequence
<220> FEATURE:
<223> OTHER INFORMATION: Synthetic: JAB0501 VLCDR2; nucleic acid

<400> SEQUENCE: 82
gctgcaacca gcttggcaga t 21

<210> SEQ ID NO 83
<211> LENGTH: 29
<212> TYPE: DNA
<213> ORGANISM: Artificial Sequence
<220> FEATURE:
<223> OTHER INFORMATION: Synthetic: JAB0501 VLCDR3; nucleic acid

<400> SEQUENCE: 83
caacaagtgt acagtactcc gtggacgtt 29

<210> SEQ ID NO 84
<211> LENGTH: 357
<212> TYPE: DNA
<213> ORGANISM: Artificial Sequence
<220> FEATURE:
<223> OTHER INFORMATION: Synthetic: JAB0501 VH; nucleic acid

<400> SEQUENCE: 84
gaggtccaac tgcaacagtc tggggcagag cttgtgaggc caggggcctc agtcaggttg 60
tcctgcacag cttctggctt caacattaaa gacagcctta tgcactgggt gaagcagagg 120
cctgaacagg gcctggagtg gattggatgg attgatcctg aggatggtga aactaaatat 180
gccccgaact tccagtctaa ggccactata actgcagtca catcctccaa cacagcctac 240
ctgcagctca gcagcctgac atctgaggac tctgccatct attactgtgc taggtatact 300
tccccgtact atactatgga ctactggggt caaggaacct cggtcaccgt ctcctcg 357

<210> SEQ ID NO 85
<211> LENGTH: 323
<212> TYPE: DNA
<213> ORGANISM: Artificial Sequence
<220> FEATURE:

<223> OTHER INFORMATION: Synthetic: JAB0501 VL; nucleic acid

<400> SEQUENCE: 85

| gacatccaga tgacccagtc tcctgcctcc cagtctgcat ctctgggaga aagtgtcacc | 60 |
| ttcacatgcc tggcaagtca gaccattggt acatggttag catggtatca gcagaaacca | 120 |
| gggaaatctc ctcagctcct gatttatgct gcaaccagct tggcagatgg ggtcccatca | 180 |
| aggttcagtg gtagtggatc tggcacaaag ttttctttca agatcagcag cctacaggct | 240 |
| gaagattttg caagttatta ctgtcaacaa gtgtacagta ctccgtggac gttcggtgga | 300 |
| ggcaccaagc tggaaatcaa acg | 323 |

<210> SEQ ID NO 86
<211> LENGTH: 1332
<212> TYPE: DNA
<213> ORGANISM: Artificial Sequence
<220> FEATURE:
<223> OTHER INFORMATION: Synthetic: JAB0501 HC; nucleic acid

<400> SEQUENCE: 86

| gaggtccaac tgcaacagtc tggggcagag cttgtgaggc caggggcctc agtcaggttg | 60 |
| tcctgcacag cttctggctt caacattaaa gacagcctta tgcactgggt gaagcagagg | 120 |
| cctgaacagg gcctggagtg gattggatgg attgatcctg aggatggtga aactaaatat | 180 |
| gccccgaact tccagtctaa ggccactata actgcagtca catcctccaa cacagcctac | 240 |
| ctgcagctca gcagcctgac atctgaggac tctgccatct attactgtgc taggtatact | 300 |
| tccccgtact atactatgga ctactggggt caaggaacct cggtcaccgt ctcctcggct | 360 |
| aaaacgacac cccccatctgt ctatccgcta gcccctggat ctgctgccca aactaactcc | 420 |
| atggtgacgc tgggatgcct ggtcaagggc tatttccctg agccagtgac agtgacctgg | 480 |
| aactctggat ccctgtccag cggtgtgcac accttcccag ctgtcctgca gtctgacctc | 540 |
| tacactctga gcagctcagt gactgtcccc tccagcacct ggcccagcca gaccgtcacc | 600 |
| tgcaacgttg cccacccggc cagcagcacc aaggtggaca gaaaaattgt gcccagggat | 660 |
| tgtggttgta agccttgcat atgtacagtc ccagaagtat catctgtctt catcttcccc | 720 |
| ccaaagccca aggatgtgct caccattact ctgactccta aggtcacgtg tgttgtggta | 780 |
| gacatcagca aggatgatcc cgaggtccag ttcagctggt ttgtagatga tgtggaggtg | 840 |
| cacacagctc agacgaaacc ccgggaggag cagatcaaca gcactttccg ttcagtcagt | 900 |
| gaacttccca tcatgcacca ggactggctc aatggcaagg agttcaaatg cagggtcaac | 960 |
| agtgcagctt tccctgcccc catcgagaaa accatctcca aaaccaaagg cagaccgaag | 1020 |
| gctccacagg tgtacaccat tccacctccc aaggagcaga tggccaagga taaagtcagt | 1080 |
| ctgacctgca tgataacaaa cttcttccct gaagacatta ctgtggagtg gcagtggaat | 1140 |
| gggcagccag cggagaacta caagaacact cagcccatca tggacacaga tggctcttac | 1200 |
| ttcgtctaca gcaagctcaa tgtgcagaag agcaactggg aggcaggaaa tactttcacc | 1260 |
| tgctctgtgt tacatgaggg cctgcacaac caccatactg agaagagcct ctcccactct | 1320 |
| cctggtaaat ga | 1332 |

<210> SEQ ID NO 87
<211> LENGTH: 645
<212> TYPE: DNA
<213> ORGANISM: Artificial Sequence
<220> FEATURE:
<223> OTHER INFORMATION: Synthetic: JAB0501 LC; nucleic acid

<400> SEQUENCE: 87

```
gacatccaga tgacccagtc tcctgcctcc cagtctgcat ctctgggaga aagtgtcacc      60
ttcacatgcc tggcaagtca gaccattggt acatggttag catggtatca gcagaaacca    120
gggaaatctc ctcagctcct gatttatgct gcaaccagct ggcagatggg gtcccatca     180 aggttcagtg gtagtggatc tggcacaaag ttttctttca agatcagcag cctacaggct    240
gaagattttg caagttatta ctgtcaacaa gtgtacagta ctccgtggac gttcggtgga    300
ggcaccaagc tggaaatcaa acgggctgat gctgcaccaa ctgtatccat cttcccacca    360
tccagtgagc agttaacatc cggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttaa                    645
```

<210> SEQ ID NO 88
<211> LENGTH: 30
<212> TYPE: DNA
<213> ORGANISM: Artificial Sequence
<220> FEATURE:
<223> OTHER INFORMATION: Synthetic: JAB0505 VHCDR1; nucleic acid

<400> SEQUENCE: 88

```
ggcttcaaca ttaaagacag ccttatgcac                                       30
```

<210> SEQ ID NO 89
<211> LENGTH: 48
<212> TYPE: DNA
<213> ORGANISM: Artificial Sequence
<220> FEATURE:
<223> OTHER INFORMATION: Synthetic: JAB0505 VHCDR2; nucleic acid

<400> SEQUENCE: 89

```
attgatcctg aggatggtga aactaggtat gccccgaact tccaggac                   48
```

<210> SEQ ID NO 90
<211> LENGTH: 30
<212> TYPE: DNA
<213> ORGANISM: Artificial Sequence
<220> FEATURE:
<223> OTHER INFORMATION: Synthetic: JAB0505 VHCDR3; nucleic acid

<400> SEQUENCE: 90

```
tatacttcca ggtactatac tatggagtac                                       30
```

<210> SEQ ID NO 91
<211> LENGTH: 33
<212> TYPE: DNA
<213> ORGANISM: Artificial Sequence
<220> FEATURE:
<223> OTHER INFORMATION: Synthetic: JAB0505 VLCDR1; nucleic acid

<400> SEQUENCE: 91

```
ctggcaagtc agaccattgg tacatggtta gca                                   33
```

<210> SEQ ID NO 92
<211> LENGTH: 21
<212> TYPE: DNA
<213> ORGANISM: Artificial Sequence
<220> FEATURE:

<223> OTHER INFORMATION: Synthetic: JAB0505 VLCDR2; nucleic acid

<400> SEQUENCE: 92
gctgcaacca gcttggcaga t        21

<210> SEQ ID NO 93
<211> LENGTH: 26
<212> TYPE: DNA
<213> ORGANISM: Artificial Sequence
<220> FEATURE:
<223> OTHER INFORMATION: Synthetic: JAB0505 VLCDR3; nucleic acid

<400> SEQUENCE: 93
caacaacttt actggactcc gtggac        26

<210> SEQ ID NO 94
<211> LENGTH: 357
<212> TYPE: DNA
<213> ORGANISM: Artificial Sequence
<220> FEATURE:
<223> OTHER INFORMATION: Synthetic: JAB0505 VH; nucleic acid

<400> SEQUENCE: 94
gaggtccaac tgcaacagtc tggggcagag cttgtgaggc caggggcctc agtcaggttg        60
tcctgcacag cttctggctt caacattaaa gacagcctta tgcactgggt gaagcagagg       120
cctgaacagg gcctggagtg gattggatgg attgatcctg aggatggtga aactaggtat       180
gccccgaact ccaggacaa ggccactata actgcagtca catcctccaa cacagcctac        240
ctgcagctca gcagcctgac atctgaggac tctgccatct attactgtgc taggtatact       300
tccaggtact atactatgga gtactggggt caaggaacct cggtcaccgt ctcctcg          357

<210> SEQ ID NO 95
<211> LENGTH: 323
<212> TYPE: DNA
<213> ORGANISM: Artificial Sequence
<220> FEATURE:
<223> OTHER INFORMATION: Synthetic: JAB0505 VL; nucleic acid

<400> SEQUENCE: 95
gacatccaga tgacccagtc tcctgcctcc cagtctgcat ctctgggaga aagtgtcacc        60
ttcacatgcc tggcaagtca gaccattggt acatggttag catggtatca gcagaaacca       120
gggaaatctc ctcagctcct gatttatgct gcaaccagct ggcagatggg gtcccatca        180
aggttcagtg gtagtggatc tggcacaaag ttttctttca agatcagcag cctacaggct       240
gaagattttg caagttatta ctgtcaacaa ctttactgga ctccgtggac gttcggtgga       300
ggcaccaagc tggaaatcaa acg                                                323

<210> SEQ ID NO 96
<211> LENGTH: 1332
<212> TYPE: DNA
<213> ORGANISM: Artificial Sequence
<220> FEATURE:
<223> OTHER INFORMATION: Synthetic: JAB0505 HC; nucleic acid

<400> SEQUENCE: 96
gaggtccaac tgcaacagtc tggggcagag cttgtgaggc caggggcctc agtcaggttg        60
tcctgcacag cttctggctt caacattaaa gacagcctta tgcactgggt gaagcagagg       120
cctgaacagg gcctggagtg gattggatgg attgatcctg aggatggtga aactaggtat       180
gccccgaact ccaggacaa ggccactata actgcagtca catcctccaa cacagcctac        240

```
ctgcagctca gcagcctgac atctgaggac tctgccatct attactgtgc taggtatact    300
tccaggtact atactatgga gtactggggt caaggaacct cggtcaccgt ctcctcggct    360
aaaacgacac ccccatctgt ctatccgcta gcccctggat ctgctgccca aactaactcc    420
atggtgacgc tgggatgcct ggtcaagggc tatttccctg agccagtgac agtgacctgg    480
aactctggat ccctgtccag cggtgtgcac accttccag ctgtcctgca gtctgacctc     540
tacactctga gcagctcagt gactgtcccc tccagcacct ggcccagcca gaccgtcacc    600
tgcaacgttg cccacccggc cagcagcacc aaggtggaca gaaaattgt gcccagggat     660 tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgaaacc ccgggaggag cagatcaaca gcactttccg ttcagtcagt    900
gaacttccca tcatgcacca ggactggctc aatggcaagg agttcaaatg cagggtcaac    960
agtgcagctt ccctgcccc catcgagaaa accatctcca aaaccaaagg cagaccgaag    1020
gctccacagg tgtacaccat tccacctccc aaggagcaga tggccaagga taaagtcagt    1080
ctgacctgca tgataacaaa cttcttccct gaagacatta ctgtggagtg cagtggaat    1140 gggcagccag cggagaacta caagaacact cagcccatca tggacacaga tggctcttac    1200
ttcgtctaca gcaagctcaa tgtgcagaag agcaactggg aggcaggaaa tactttcacc    1260
tgctctgtgt tacatgaggg cctgcacaac caccatactg agaagagcct ctcccactct    1320
cctggtaaat ga                                                       1332
```

<210> SEQ ID NO 97
<211> LENGTH: 645
<212> TYPE: DNA
<213> ORGANISM: Artificial Sequence
<220> FEATURE:
<223> OTHER INFORMATION: Synthetic: JAB0505 LC; nucleic acid

<400> SEQUENCE: 97

```
gacatccaga tgacccagtc tcctgcctcc cagtctgcat ctctgggaga aagtgtcacc     60
ttcacatgcc tggcaagtca gaccattggt acatggttag catggtatca gcagaaacca    120
gggaaatctc ctcagctcct gatttatgct gcaaccagct ggcagatgg ggtcccatca     180 aggttcagtg gtagtggatc tggcacaaag ttttctttca agatcagcag cctacaggct    240
gaagattttg caagttatta ctgtcaacaa ctttactgga ctccgtggac gttcggtgga    300
ggcaccaagc tggaaatcaa acgggctgat gctgcaccaa ctgtatccat cttcccacca    360
tccagtgagc agttaacatc cggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttaa                    645
```

<210> SEQ ID NO 98
<211> LENGTH: 103
<212> TYPE: PRT
<213> ORGANISM: Artificial Sequence
<220> FEATURE:
<223> OTHER INFORMATION: Synthetic: pDMC074

```
<400> SEQUENCE: 98

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu
            100

<210> SEQ ID NO 99
<211> LENGTH: 123
<212> TYPE: PRT
<213> ORGANISM: Artificial Sequence
<220> FEATURE:
<223> OTHER INFORMATION: Synthetic: pDMC094

<400> SEQUENCE: 99

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu
            115                 120

<210> SEQ ID NO 100
<211> LENGTH: 123
<212> TYPE: PRT
<213> ORGANISM: Artificial Sequence
<220> FEATURE:
<223> OTHER INFORMATION: Synthetic: pDMC075

<400> SEQUENCE: 100

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60
```

```
Val Tyr Gln Lys Gly Cys Phe Gln Val Tyr Glu Gln Gly Lys Met Thr
 65                  70                  75                  80

Cys Lys Thr Pro Pro Ser Pro Gly Gln Ala Val Glu Cys Cys Gln Gly
                 85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu
            115                 120

<210> SEQ ID NO 101
<211> LENGTH: 103
<212> TYPE: PRT
<213> ORGANISM: Artificial Sequence
<220> FEATURE:
<223> OTHER INFORMATION: Synthetic: pDMC076

<400> SEQUENCE: 101

Met Glu Asp Glu Lys Pro Lys Val Asn Pro Lys Leu Tyr Met Cys Val
  1               5                  10                  15

Cys Glu Gly Leu Ser Cys Gly Asn Glu Asp His Cys Glu Gly Gln Gln
                 20                  25                  30

Cys Phe Ser Ser Leu Ser Ile Asn Asp Gly Phe His Val Tyr Gln Lys
             35                  40                  45

Gly Cys Phe Gln Val Tyr Glu Gln Gly Lys Met Thr Cys Lys Thr Pro
 50                  55                  60

Pro Ser Pro Gly Gln Ala Val Glu Cys Cys Gln Gly Asp Trp Cys Asn
 65                  70                  75                  80

Arg Asn Ile Thr Ala Gln Leu Pro Thr Lys Gly Lys Ser Phe Pro Gly
                 85                  90                  95

Thr Gln Asn Phe His Leu Glu
            100

<210> SEQ ID NO 102
<211> LENGTH: 347
<212> TYPE: PRT
<213> ORGANISM: Artificial Sequence
<220> FEATURE:
<223> OTHER INFORMATION: Synthetic: pDMC099

<400> SEQUENCE: 102

Met Val Asp Gly Val Met Ile Leu Pro Val Leu Ile Met Ile Ala Leu
  1               5                  10                  15

Pro Ser Pro Ser Met Ser Pro Ile Leu Gly Tyr Trp Lys Ile Lys Gly
                 20                  25                  30

Leu Val Gln Pro Thr Arg Leu Leu Leu Glu Tyr Leu Glu Glu Lys Tyr
             35                  40                  45

Glu Glu His Leu Tyr Glu Arg Asp Glu Gly Asp Lys Trp Arg Asn Lys
 50                  55                  60

Lys Phe Glu Leu Gly Leu Glu Phe Pro Asn Leu Pro Tyr Tyr Ile Asp
 65                  70                  75                  80

Gly Asp Val Lys Leu Thr Gln Ser Met Ala Ile Ile Arg Tyr Ile Ala
                 85                  90                  95

Asp Lys His Asn Met Leu Gly Gly Cys Pro Lys Glu Arg Ala Glu Ile
            100                 105                 110

Ser Met Leu Glu Gly Ala Val Leu Asp Ile Arg Tyr Gly Val Ser Arg
            115                 120                 125

Ile Ala Tyr Ser Lys Asp Phe Glu Thr Leu Lys Val Asp Phe Leu Ser
            130                 135                 140
```

```
Lys Leu Pro Glu Met Leu Lys Met Phe Glu Asp Arg Leu Cys His Lys
145                 150                 155                 160

Thr Tyr Leu Asn Gly Asp His Val Thr His Pro Asp Phe Met Leu Tyr
            165                 170                 175

Asp Ala Leu Asp Val Val Leu Tyr Met Asp Pro Met Cys Leu Asp Ala
        180                 185                 190

Phe Pro Lys Leu Val Cys Phe Lys Lys Arg Ile Glu Ala Ile Pro Gln
    195                 200                 205

Ile Asp Lys Tyr Leu Lys Ser Ser Lys Tyr Ile Ala Trp Pro Leu Gln
210                 215                 220

Gly Trp Gln Ala Thr Phe Gly Gly Asp His Pro Pro Lys Ser Asp
225                 230                 235                 240

Gly Gly Ser Gly Met Glu Asp Glu Lys Pro Lys Val Asn Pro Lys Leu
                245                 250                 255

Tyr Met Cys Val Cys Glu Gly Leu Ser Cys Gly Asn Glu Asp His Cys
            260                 265                 270

Glu Gly Gln Gln Cys Phe Ser Ser Leu Ser Ile Asn Asp Gly Phe His
        275                 280                 285

Val Tyr Gln Lys Gly Cys Phe Gln Val Tyr Gln Gly Lys Met Thr
    290                 295                 300

Cys Lys Thr Pro Pro Ser Pro Gly Gln Ala Val Glu Cys Cys Gln Gly
305                 310                 315                 320

Asp Trp Cys Asn Arg Asn Ile Thr Ala Gln Leu Pro Thr Lys Gly Lys
                325                 330                 335

Ser Phe Pro Gly Thr Gln Asn Phe His Leu Glu
                340                 345

<210> SEQ ID NO 103
<211> LENGTH: 327
<212> TYPE: PRT
<213> ORGANISM: Artificial Sequence
<220> FEATURE:
<223> OTHER INFORMATION: Synthetic: pDMC100

<400> SEQUENCE: 103

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160
```

```
Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Gly Ser Gly
    210                 215                 220

Met Glu Asp Glu Lys Pro Lys Val Asn Pro Lys Leu Tyr Met Cys Val
225                 230                 235                 240

Cys Glu Gly Leu Ser Cys Gly Asn Glu Asp His Cys Glu Gly Gln Gln
                245                 250                 255

Cys Phe Ser Ser Leu Ser Ile Asn Asp Gly Phe His Val Tyr Gln Lys
                260                 265                 270

Gly Cys Phe Gln Val Tyr Glu Gln Gly Lys Met Thr Cys Lys Thr Pro
            275                 280                 285

Pro Ser Pro Gly Gln Ala Val Glu Cys Cys Gln Gly Asp Trp Cys Asn
        290                 295                 300

Arg Asn Ile Thr Ala Gln Leu Pro Thr Lys Gly Lys Ser Phe Pro Gly
305                 310                 315                 320

Thr Gln Asn Phe His Leu Glu
                325

<210> SEQ ID NO 104
<211> LENGTH: 146
<212> TYPE: PRT
<213> ORGANISM: Artificial Sequence
<220> FEATURE:
<223> OTHER INFORMATION: Synthetic: pDMC068

<400> SEQUENCE: 104

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu
145
```